(12) United States Patent
Höök et al.

(10) Patent No.: US 6,953,839 B2
(45) Date of Patent: Oct. 11, 2005

(54) PROKARYOTIC COLLAGEN-LIKE PROTEINS AND USES THEREOF

(75) Inventors: Magnus Höök, Houston, TX (US); Slawomir Lukomski, Morgantown, WV (US); Yi Xu, Houston, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/830,792

(22) Filed: Apr. 23, 2004

(65) Prior Publication Data

US 2004/0214282 A1 Oct. 28, 2004

Related U.S. Application Data

(60) Provisional application No. 60/464,816, filed on Apr. 23, 2003.

(51) Int. Cl.[7] ................................................. C07K 14/00
(52) U.S. Cl. ...................................... 530/356; 530/350
(58) Field of Search ................................. 530/356, 350

(56) References Cited

PUBLICATIONS

Xu et al., "Streptococcal Scl1 and Scl2 proteins from collagen–like triple helices", 2002, The Journal of Biological Chemistry, 277(30), 27312–18.*

Apte et al., "Cloning of the human and mouse type X collagen genes and mapping of the mouse type X collagen gen to chromosome 10", 1992, Eupopean Journal of Biochemistry, 206, 217–224.*

Wells, "Additivity of Mutational Effects in Proteins", 1990, Biochemistry, 29(37), 8509–8517.*

GenBank sequence for AF296333, Nov. 06, 2000.*

Bowie et al., "Deciphering the message in protein sequences: Tolerance to amino acid substitutions", 1990, Science, 247, 1306–1310.*

* cited by examiner

*Primary Examiner*—Robert A. Wax
*Assistant Examiner*—Suzanne M. Mayer
(74) *Attorney, Agent, or Firm*—Benjamin Aaron Adler

(57) ABSTRACT

The present invention provides recombinant triple helical proteins or collagen-like proteins comprising a prokaryotic protein or one or more domains of a prokaryotic protein comprising a collagen-like peptide sequence of repeated Gly-Xaa-Yaa triplets and, optionally, one or more domains from a mammalian collagen. Also provided are expression vectors and host cells containing the expression vectors to produce these recombinant proteins and methods of production for the same. Additionally, antibodies are provided that are directed against a recombinant collagen-like protein that, preferably, binds an integrin. Furthermore, a method of screening for potential therapeutic compounds that inhibit the integrin-binding or -interacting activities of recombinant collagen-like proteins.

9 Claims, 22 Drawing Sheets

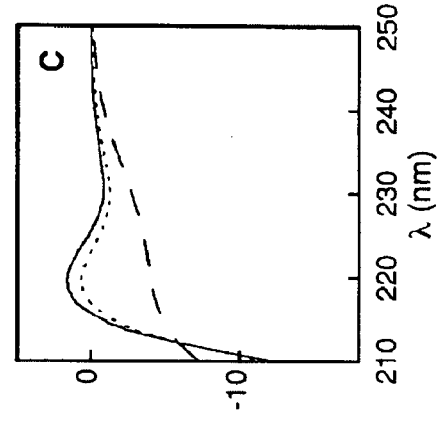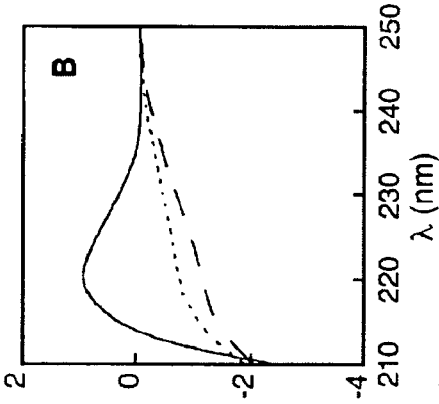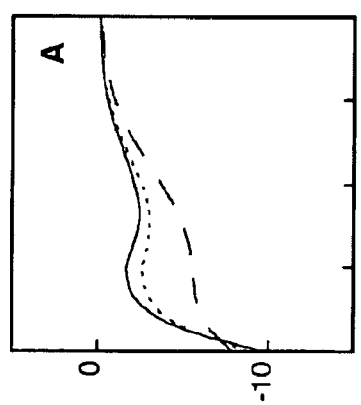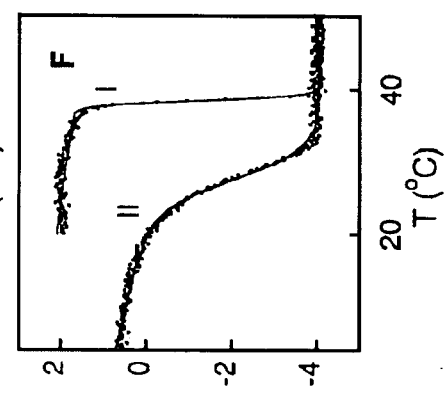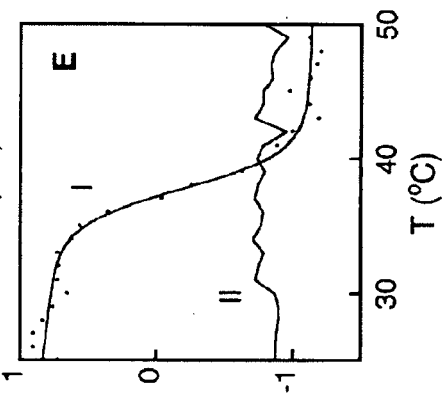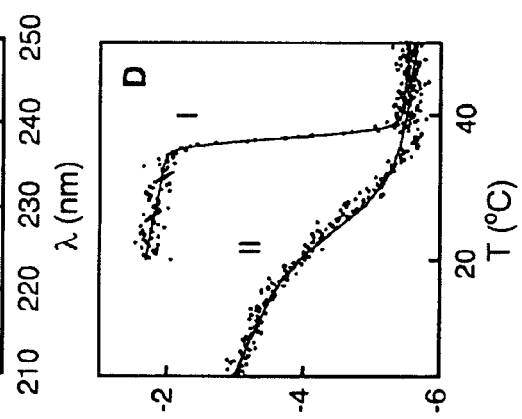
Fig. 3A  Fig. 3B  Fig. 3C
Fig. 3D  Fig. 3E  Fig. 3F

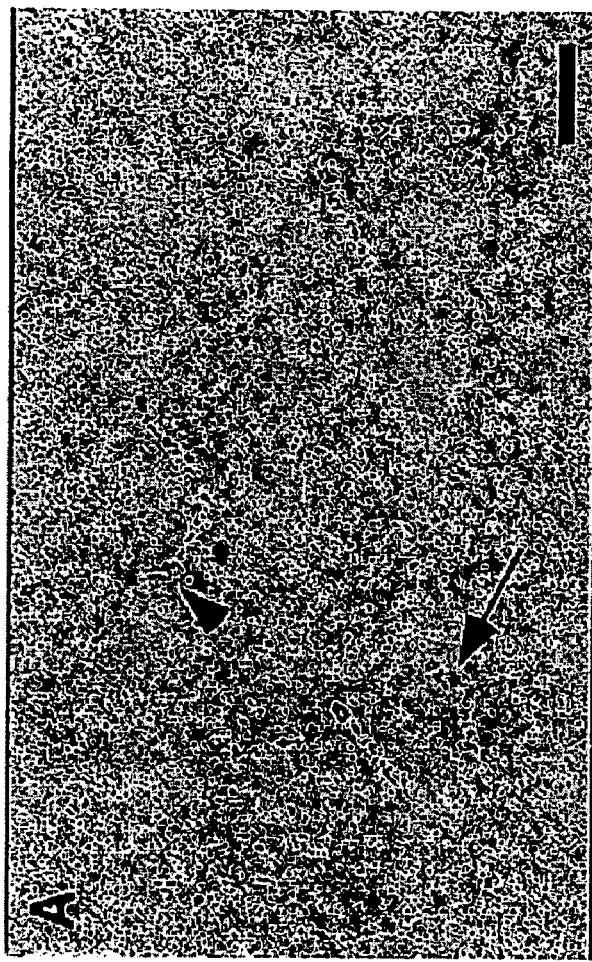
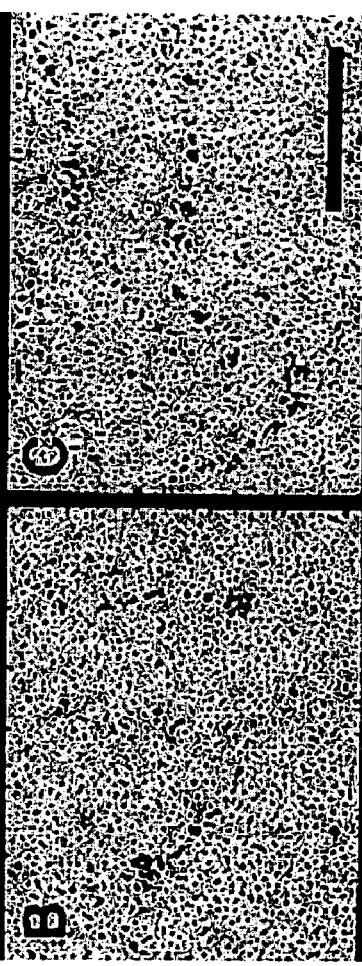
Fig. 4A
Fig. 4B
Fig. 4C

Fig. 5A

EDSETATARTKLLEKLTELRSQSQDRVPQTSDITQAYTLWGTSYDSVELYKYLQQ
IEEYLQKQKYHEEQWKKEITDGLKSGALRGEKGEAGPQGEKGLPGLTGLPGLPG
ERGPRGPKGDRGETGAQGPVGPQGEKGEAGTPGKDGLRGPQGDPGAPGKDG
APGEKGDRGETGAQGPVGPQGEKGEAGTPGKDGAPGEKGEKGDRGETGATG
AQGPQGEAGKDGAQGPVGPQGEKGETGAQGPAGPQGEKGETGAQGPAGPQG
EAGQPGEKAPEKSPEVTPTPEMPEQPGEQAPEKSKEVTPAPEKPwshpqfek

SEQ ID NO: 44

Black
V; variable region

Red
CL; collagen-like region

Blue
L; linker region

Green
WM; cell wall/membrane region (only 1 residue=P)

Lower case
stag; *strep*-tagII

Fig. 5B

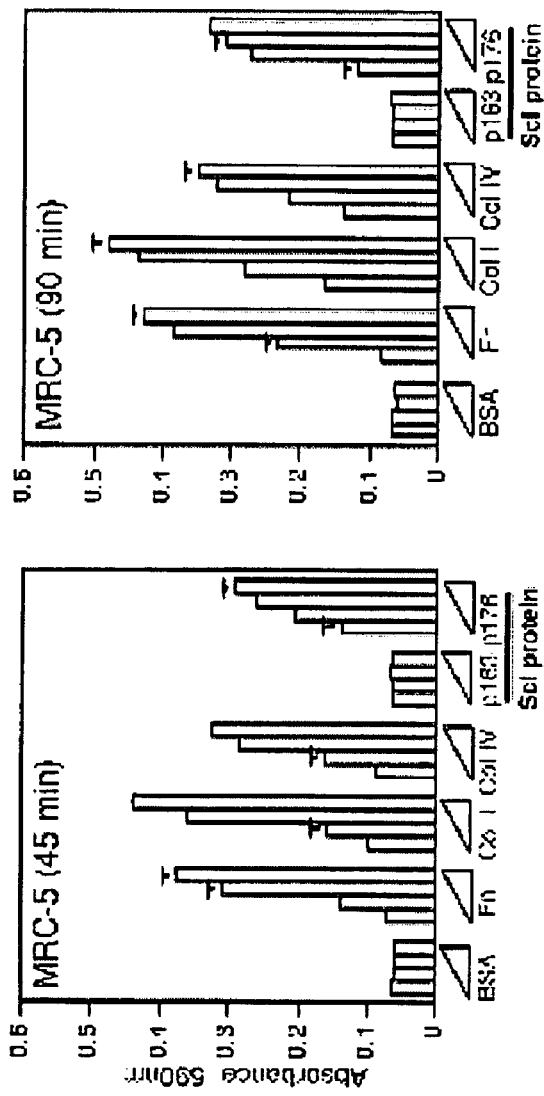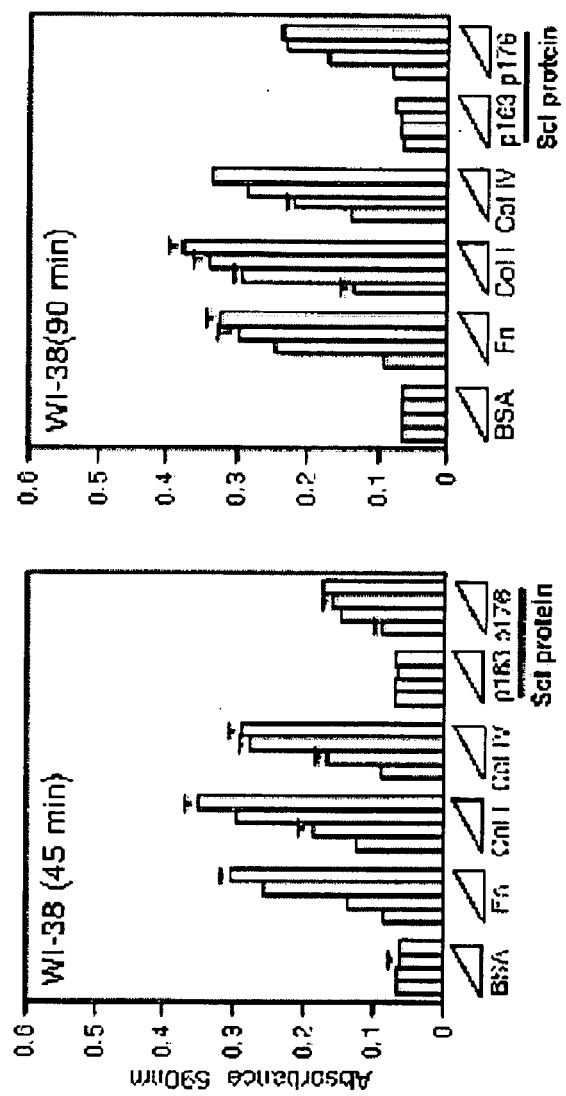

45 minutes

90 minutes

WI-38

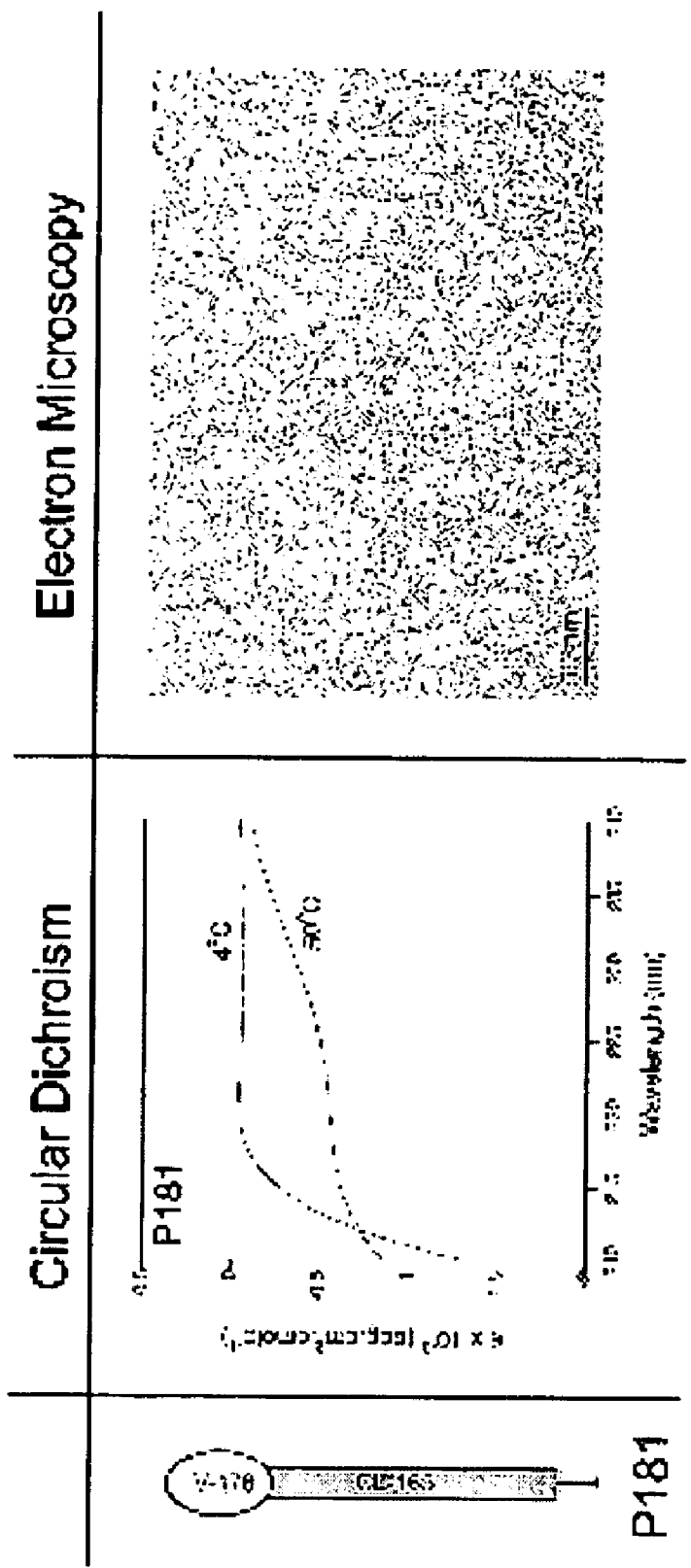

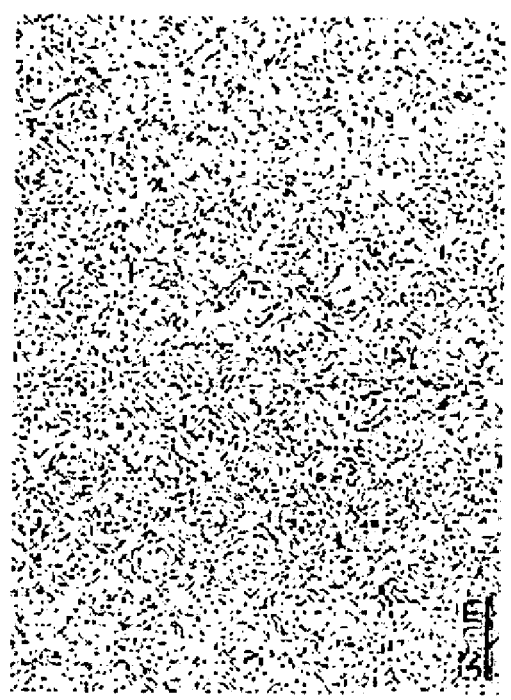
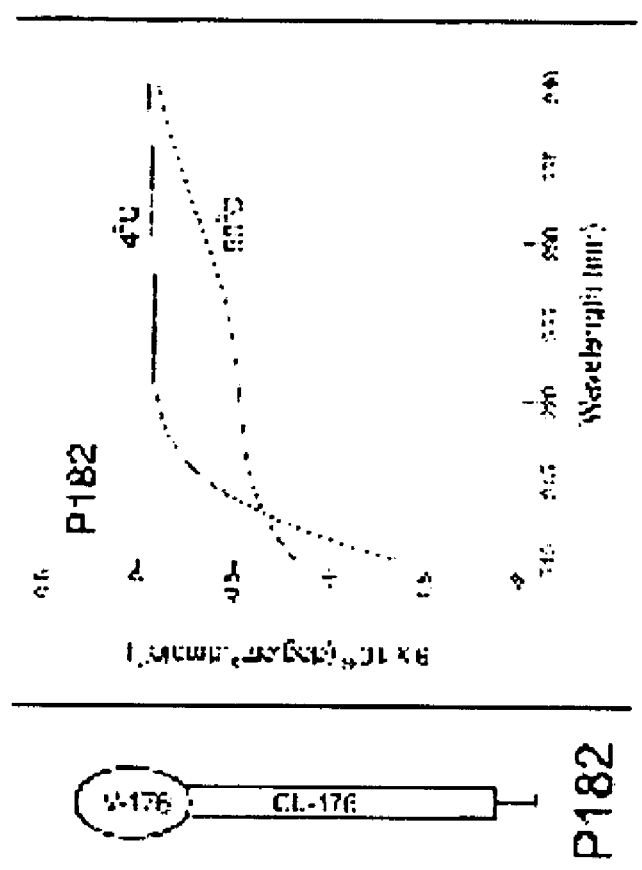
Fig. 8F
Fig. 8E
Fig. 8D

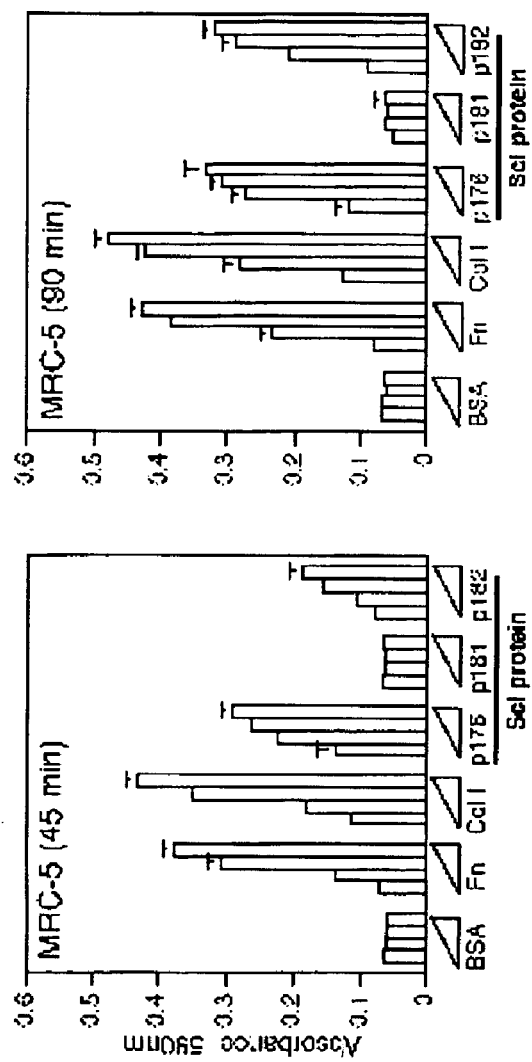
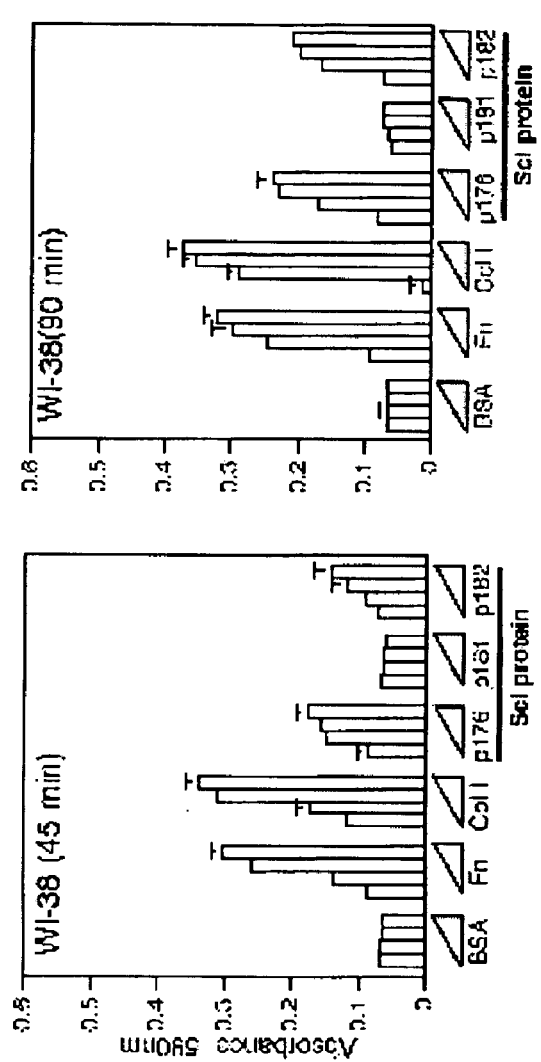
Fig. 8G
Fig. 8H

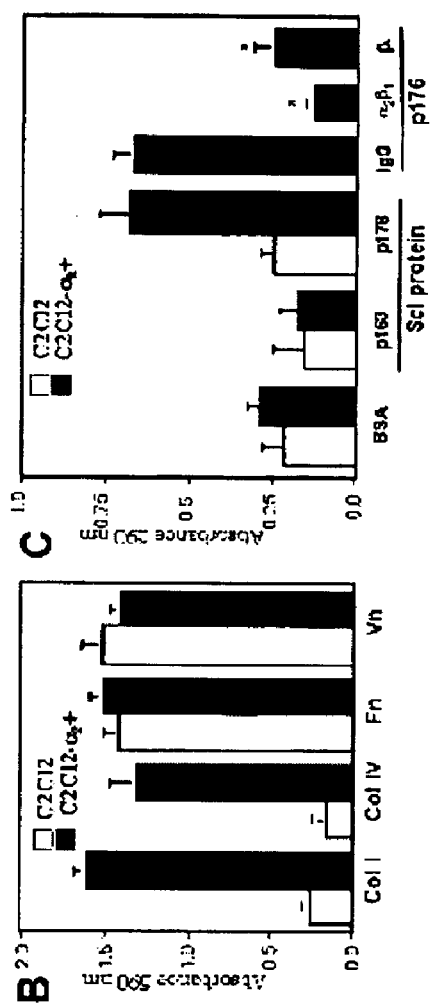
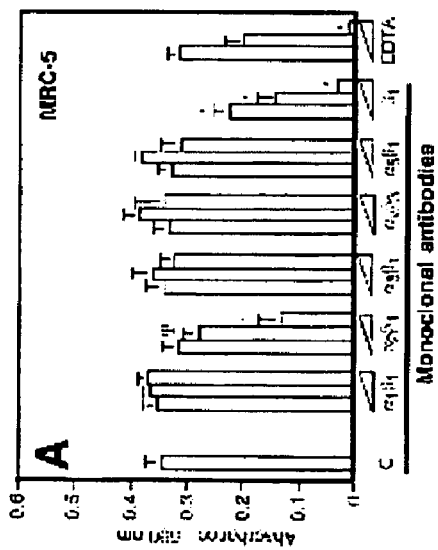
Fig. 9A
Fig. 9B
Fig. 9C

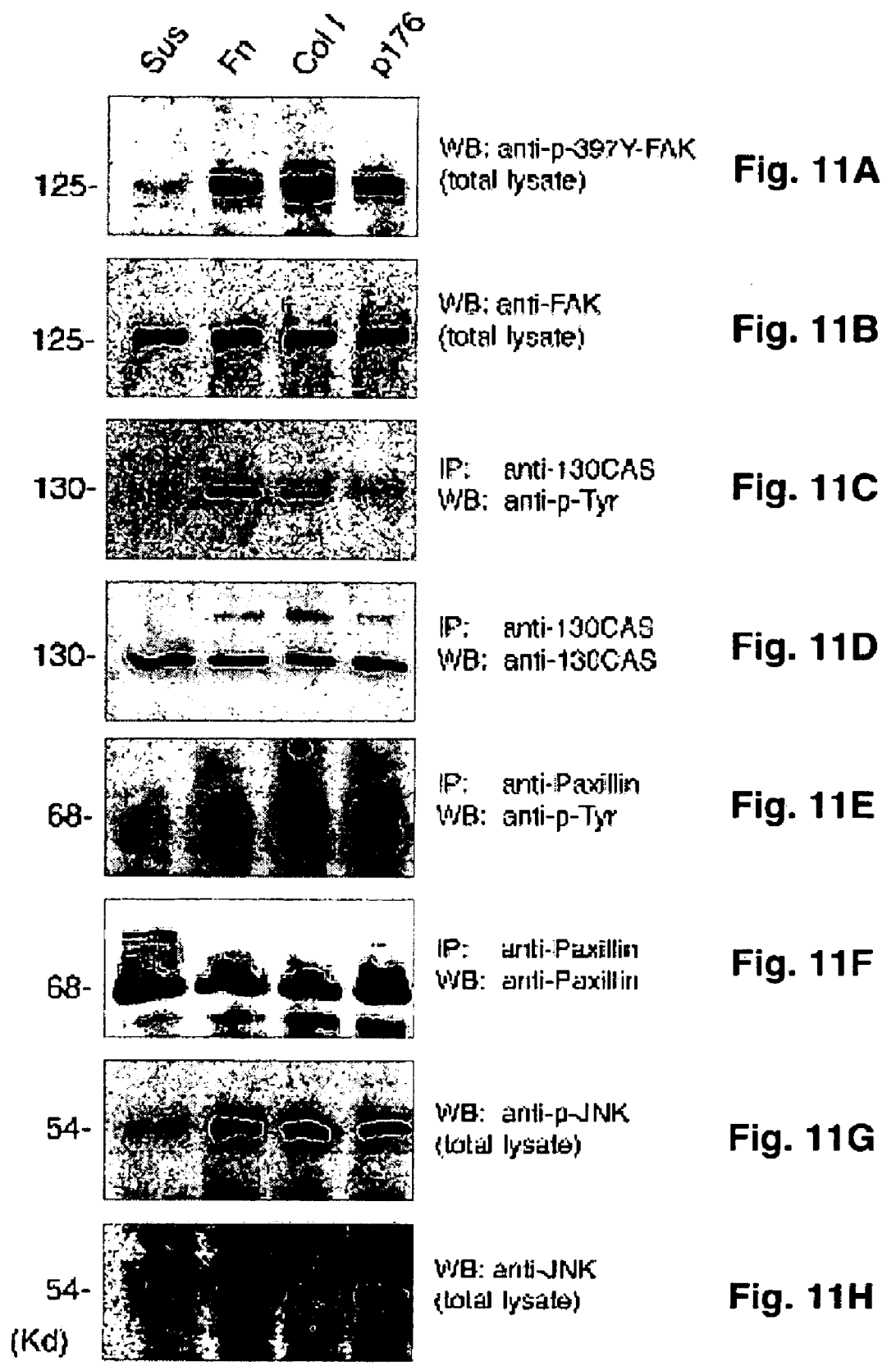

SEQUENCE LISTING

<160> NUMBER OF SEQ ID NOS: 46

<210> SEQ ID NO 1
<211> LENGTH: 150
<212> TYPE: PRT
<213> ORGANISM: artificial sequence
<220> FEATURE:
<223> OTHER INFORMATION: recombinant Scl1 protein

<400> SEQUENCE: 1

```
Gly Lys Ser Gly Ile Lys Gly Asp Arg Gly Glu Thr Gly Pro Ala
                 5                  10                  15

Gly Pro Ala Gly Pro Gln Gly Lys Thr Gly Glu Arg Gly Ala Gln
                20                  25                  30

Gly Pro Lys Gly Asp Arg Gly Glu Gln Gly Ile Gln Gly Lys Ala
                35                  40                  45

Gly Glu Lys Gly Glu Arg Gly Glu Lys Gly Asp Lys Gly Glu Thr
                50                  55                  60

Gly Glu Arg Gly Glu Lys Gly Glu Ala Gly Ile Gln Gly Pro Gln
                65                  70                  75

Gly Glu Ala Gly Lys Asp Gly Ala Pro Gly Lys Asp Gly Ala Pro
                80                  85                  90

Gly Glu Lys Gly Glu Lys Gly Asp Arg Gly Glu Thr Gly Ala Gln
                95                  100                 105

Gly Pro Val Gly Pro Gln Gly Glu Lys Gly Glu Thr Gly Ala Gln
                110                 115                 120

Gly Pro Ala Gly Pro Gln Gly Glu Ala Gly Lys Pro Gly Glu Gln
                125                 130                 135

Gly Pro Ala Gly Pro Gln Gly Glu Ala Gly Gln Pro Gly Glu Lys
                140                 145                 150
```

<210> SEQ ID NO 2
<211> LENGTH: 138
<212> TYPE: PRT
<213> ORGANISM: artificial sequence
<220> FEATURE:
<223> OTHER INFORMATION: recombinant Scl1 protein

<400> SEQUENCE: 2

```
Gly Glu Lys Gly Glu Ala Gly Ile Gln Gly Pro Gln Gly Lys Ala
                 5                  10                  15

Gly Lys Asp Gly Ala Pro Gly Lys Asp Gly Ala Val Gly Ala Gln
                20                  25                  30

Gly Pro Lys Gly Asp Lys Gly Asp Thr Gly Glu Lys Gly Glu Thr
                35                  40                  45

Gly Ala Thr Gly Ala Gln Gly Pro Gln Gly Glu Ala Gly Lys Asp
                50                  55                  60

Gly Ala Pro Gly Glu Lys Gly Glu Lys Gly Asp Arg Gly Glu Thr
                65                  70                  75

Gly Ala Gln Gly Pro Val Gly Pro Gln Gly Lys Gly Glu Thr
                80                  85                  90

Gly Ala Gln Gly Pro Ala Gly Pro Gln Gly Glu Lys Gly Glu Thr
                95                  100                 105

Gly Ala Gln Gly Pro Ala Gly Pro Gln Gly Glu Ala Gly Lys Pro
                110                 115                 120
```

```
Gly Glu Gln Gly Pro Ala Gly Pro Gln Gly Glu Ala Gly Lys Pro
            125                 130                 135

Gly Glu Lys

<210> SEQ ID NO 3
<211> LENGTH: 31
<212> TYPE: PRT
<213> ORGANISM: artificial sequence
<220> FEATURE:
<223> OTHER INFORMATION: recombinant Scl1 protein

<400> SEQUENCE: 3

Gly Asp Lys Gly Glu Thr Gly Leu Ala Gly Pro Val Gly Pro Ala
                  5                  10                  15

Gly Lys Ala Gly Ala Arg Gly Ala Gln Gly Pro Ala Gly Pro Arg
             20                  25                  30

Gly

<210> SEQ ID NO 4
<211> LENGTH: 126
<212> TYPE: PRT
<213> ORGANISM: artificial sequence
<220> FEATURE:
<223> OTHER INFORMATION: recombinant Scl1 protein

<400> SEQUENCE: 4

Gly Glu Lys Gly Asp Ala Gly Pro Arg Gly Glu Arg Gly Pro Gln
                  5                  10                  15

Gly Pro Val Gly Pro Ala Gly Lys Ala Gly Glu Lys Gly Glu Ala
             20                  25                  30

Gly Ile Gln Gly Pro Gln Gly Glu Ala Gly Lys Asp Gly Ala Pro
             35                  40                  45

Gly Lys Asp Gly Ala Pro Gly Glu Lys Gly Glu Lys Gly Asp Arg
             50                  55                  60

Gly Glu Thr Gly Ala Gln Gly Pro Val Gly Pro Gln Gly Glu Lys
             65                  70                  75

Gly Glu Thr Gly Ala Gln Gly Pro Ala Gly Pro Gln Gly Glu Ala
             80                  85                  90

Gly Lys Pro Gly Glu Gln Gly Pro Ala Gly Pro Gln Gly Glu Ala
             95                 100                 105

Gly Lys Pro Gly Glu Gln Gly Pro Ala Gly Pro Gln Gly Glu Ala
            110                 115                 120

Gly Lys Pro Gly Glu Lys
            125

<210> SEQ ID NO 5
<211> LENGTH: 42
<212> TYPE: PRT
<213> ORGANISM: artificial sequence
<220> FEATURE:
<223> OTHER INFORMATION: recombinant Scl1 protein

<400> SEQUENCE: 5

Gly Glu Lys Gly Asp Pro Gly Ala Gln Gly Pro Lys Gly Glu Lys
                  5                  10                  15

Gly Glu Lys Gly Asp Arg Gly Asp Thr Gly Ala Gln Gly Pro Val
             20                  25                  30

Gly Pro Gln Gly Glu Ala Gly Gln Pro Gly Glu Lys
             35                  40
```

```
<210> SEQ ID NO 6
<211> LENGTH: 123
<212> TYPE: PRT
<213> ORGANISM: artificial sequence
<220> FEATURE:
<223> OTHER INFORMATION: recombinant Scl1 protein

<400> SEQUENCE: 6

Gly Glu Lys Gly Asp Ala Gly Pro Val Gly Pro Ala Gly Pro Arg
                 5                  10                  15

Gly Glu Arg Gly Pro Gln Gly Glu Lys Gly Ala Gln Gly Leu Lys
             20                  25                  30

Gly Glu Lys Gly Asp Thr Gly Ala Val Gly Ala Gln Gly Pro Lys
             35                  40                  45

Gly Asp Lys Gly Asp Thr Gly Glu Arg Gly Glu Lys Gly Asp Thr
             50                  55                  60

Gly Ala Thr Gly Ala Gln Gly Pro Gln Gly Glu Ala Gly Lys Asp
             65                  70                  75

Gly Ala Pro Gly Lys Asp Gly Ala Pro Gly Glu Lys Gly Glu Lys
             80                  85                  90

Gly Asp Arg Gly Glu Thr Gly Ala Gln Gly Pro Val Gly Gln Gln
             95                 100                 105

Gly Glu Ala Gly Lys Pro Gly Glu Gln Gly Glu Ala Gly Lys Pro
            110                 115                 120

Gly Glu Gln

<210> SEQ ID NO 7
<211> LENGTH: 114
<212> TYPE: PRT
<213> ORGANISM: artificial sequence
<220> FEATURE:
<223> OTHER INFORMATION: recombinant Scl1 protein

<400> SEQUENCE: 7

Gly Pro Ala Gly Pro Lys Gly Glu Thr Gly Pro Ala Gly Pro Ala
                 5                  10                  15

Gly Pro Glu Gly Lys Pro Gly Lys Ala Gly Glu Lys Gly Asp Arg
             20                  25                  30

Gly Glu Lys Gly Glu Ala Gly Ile Gln Gly Pro Gln Gly Glu Lys
             35                  40                  45

Gly Asp Thr Gly Ala Gln Gly Pro Gln Gly Glu Ala Gly Ala Pro
             50                  55                  60

Gly Glu Lys Gly Glu Lys Gly Asp Arg Gly Glu Thr Gly Ala Gln
             65                  70                  75

Gly Pro Val Gly Pro Gln Gly Glu Lys Gly Glu Thr Gly Ala Gln
             80                  85                  90

Gly Pro Gln Gly Glu Ala Gly Lys Pro Gly Glu Gln Gly Pro Gln
             95                 100                 105

Gly Glu Ala Gly Lys Pro Gly Glu Lys
            110

<210> SEQ ID NO 8
<211> LENGTH: 102
<212> TYPE: PRT
<213> ORGANISM: artificial sequence
<220> FEATURE:
<223> OTHER INFORMATION: recombinant Scl1 protein
```

-continued

```
<400> SEQUENCE: 8

Gly Pro Ala Gly Pro Lys Gly Glu Thr Gly Pro Ala Gly Pro Ala
                  5                  10                  15

Gly Pro Glu Gly Lys Pro Gly Lys Ala Gly Glu Lys Gly Asp Arg
                 20                  25                  30

Gly Glu Lys Gly Glu Ala Gly Ile Gln Gly Pro Gln Gly Glu Lys
                 35                  40                  45

Gly Asp Thr Gly Ala Gln Gly Pro Gln Gly Glu Ala Gly Ala Pro
                 50                  55                  60

Gly Glu Lys Gly Glu Lys Gly Asp Arg Gly Glu Thr Gly Ala Gln
                 65                  70                  75

Gly Pro Val Gly Pro Gln Gly Glu Lys Gly Glu Thr Gly Ala Gln
                 80                  85                  90

Gly Pro Gln Gly Glu Ala Gly Lys Pro Gly Glu Lys
                 95                 100

<210> SEQ ID NO 9
<211> LENGTH: 79
<212> TYPE: PRT
<213> ORGANISM: artificial sequence
<220> FEATURE:
<223> OTHER INFORMATION: recombinant Scl1 protein

<400> SEQUENCE: 9

Gly Pro Ala Gly Pro Lys Gly Glu Thr Gly Pro Ala Gly Pro Ala
                  5                  10                  15

Gly Pro Glu Gly Lys Pro Gly Lys Ala Gly Glu Lys Gly Asp Arg
                 20                  25                  30

Gly Glu Lys Gly Glu Ala Gly Ile Gln Gly Pro Gln Gly Glu Lys
                 35                  40                  45

Gly Asp Thr Gly Ala Gln Gly Pro Gln Gly Glu Ala Gly Lys Pro
                 50                  55                  60

Gly Glu Lys Ala Pro Glu Lys Ser Pro Glu Gly Glu Ala Gly Gln
                 65                  70                  75

Pro Gly Glu Lys

<210> SEQ ID NO 10
<211> LENGTH: 150
<212> TYPE: PRT
<213> ORGANISM: artificial sequence
<220> FEATURE:
<223> OTHER INFORMATION: recombinant Scl1 protein

<400> SEQUENCE: 10

Gly Lys Ser Gly Ile Lys Gly Asp Arg Gly Glu Thr Gly Pro Ala
                  5                  10                  15

Gly Pro Ala Gly Pro Gln Gly Lys Thr Gly Glu Arg Gly Ala Gln
                 20                  25                  30

Gly Pro Lys Gly Asp Arg Gly Glu Gln Gly Ile Gln Gly Lys Ala
                 35                  40                  45

Gly Glu Lys Gly Glu Arg Gly Glu Lys Gly Asp Lys Gly Glu Thr
                 50                  55                  60

Gly Glu Arg Gly Glu Lys Gly Glu Ala Gly Ile Gln Gly Pro Gln
                 65                  70                  75

Gly Glu Ala Gly Lys Asp Gly Ala Pro Gly Lys Asp Gly Ala Pro
                 80                  85                  90
```

Gly Glu Lys Gly Glu Lys Gly Asp Arg Gly Glu Thr Gly Ala Gln
                95                 100                 105

Gly Pro Val Gly Pro Gln Gly Glu Lys Gly Glu Thr Gly Ala Gln
              110                 115                 120

Gly Pro Ala Gly Pro Gln Gly Glu Ala Gly Lys Pro Gly Glu Gln
              125                 130                 135

Gly Pro Ala Gly Pro Gln Gly Glu Ala Gly Gln Pro Gly Glu Lys
              140                 145                 150

<210> SEQ ID NO 11
<211> LENGTH: 135
<212> TYPE: PRT
<213> ORGANISM: artificial sequence
<220> FEATURE:
<223> OTHER INFORMATION: recombinant Scl1 protein

<400> SEQUENCE: 11

Gly Pro Ala Gly Pro Glu Gly Lys Pro Gly Pro Lys Gly Asp Lys
              5                   10                  15

Gly Glu Thr Gly Ala Arg Gly Pro Arg Gly Glu Arg Gly Glu Thr
              20                  25                  30

Gly Leu Gln Gly Pro Lys Gly Glu Ala Gly Lys Asp Gly Ala Gln
              35                  40                  45

Gly Glu Lys Gly Glu Lys Gly Asp Arg Gly Glu Lys Gly Glu Ala
              50                  55                  60

Gly Ile Gln Gly Pro Lys Gly Glu Ala Gly Lys Asp Gly Ala Pro
              65                  70                  75

Gly Glu Lys Gly Glu Lys Gly Asp Arg Gly Glu Thr Gly Ala Gln
              80                  85                  90

Gly Pro Val Gly Pro Gln Gly Glu Lys Gly Glu Thr Gly Ala Gln
              95                  100                 105

Gly Pro Ala Gly Pro Gln Gly Glu Ala Gly Lys Pro Gly Glu Gln
              110                 115                 120

Gly Pro Ala Gly Pro Gln Gly Glu Ala Gly Lys Pro Gly Glu Lys
              125                 130                 135

<210> SEQ ID NO 12
<211> LENGTH: 118
<212> TYPE: PRT
<213> ORGANISM: artificial sequence
<220> FEATURE:
<223> OTHER INFORMATION: recombinant Scl1 protein

<400> SEQUENCE: 12

Gly Asp Lys Gly Asp Ala Gly Pro Lys Gly Glu Arg Gly Pro Ala
              5                   10                  15

Gly Pro Gln Gly Pro Val Gly Pro Lys Gly Glu Ala Gly Lys Val
              20                  25                  30

Gly Ala Gln Gly Pro Lys Gly Asp Pro Gly Ala Pro Gly Lys Asp
              35                  40                  45

Gly Ala Lys Gly Glu Lys Gly Asp Lys Gly Asp Thr Gly Glu Arg
              50                  55                  60

Gly Glu Lys Gly Asp Ile Gly Ala Thr Gly Ala Gln Gly Pro Ala
              65                  70                  75

Gly Pro Gln Gly Glu Ala Gly Lys Pro Gly Glu Gln Gly Pro Ala
              80                  85                  90

```
Gly Pro Gln Gly Glu Ala Gly Lys Pro Gly Glu Lys Ala Pro Glu
                95                 100                 105

Lys Ser Pro Glu Gly Glu Ala Gly Gln Pro Gly Glu Lys
                110                 115

<210> SEQ ID NO 13
<211> LENGTH: 144
<212> TYPE: PRT
<213> ORGANISM: artificial sequence
<220> FEATURE:
<223> OTHER INFORMATION: recombinant Scl1 protein

<400> SEQUENCE: 13

Gly Asp Lys Gly Asp Ala Gly Pro Lys Gly Glu Arg Gly Pro Ala
                 5                  10                  15

Gly Pro Gln Gly Pro Val Gly Pro Lys Gly Glu Ala Gly Lys Val
                20                  25                  30

Gly Ala Gln Gly Pro Lys Gly Asp Pro Gly Ala Pro Gly Lys Asp
                35                  40                  45

Gly Ala Lys Gly Glu Lys Gly Asp Lys Gly Asp Thr Gly Glu Arg
                50                  55                  60

Gly Glu Lys Gly Asp Ile Gly Ala Thr Gly Ala Gln Gly Pro Gln
                65                  70                  75

Gly Glu Ala Gly Lys Asp Gly Ala Pro Gly Glu Lys Gly Asp Lys
                80                  85                  90

Gly Asp Arg Gly Glu Thr Gly Ala Gln Gly Pro Val Gly Pro Gln
                95                 100                 105

Gly Glu Lys Gly Glu Thr Gly Ala Gln Gly Pro Ala Gly Pro Gln
                110                 115                 120

Gly Glu Ala Gly Lys Pro Gly Glu Gln Gly Pro Ala Gly Pro Gln
                125                 130                 135

Gly Glu Ala Gly Lys Pro Gly Glu Lys
                140

<210> SEQ ID NO 14
<211> LENGTH: 114
<212> TYPE: PRT
<213> ORGANISM: artificial sequence
<220> FEATURE:
<223> OTHER INFORMATION: recombinant Scl1 protein

<400> SEQUENCE: 14

Gly Asp Lys Gly Asp Ala Gly Pro Lys Gly Glu Arg Gly Pro Ala
                 5                  10                  15

Gly Pro Gln Gly Pro Val Gly Pro Lys Gly Glu Ala Gly Lys Val
                20                  25                  30

Gly Ala Gln Gly Pro Lys Gly Asp Pro Gly Ala Pro Gly Lys Asp
                35                  40                  45

Gly Ala Lys Gly Glu Lys Gly Asp Lys Gly Asp Thr Gly Glu Arg
                50                  55                  60

Gly Glu Lys Gly Asp Ile Gly Ala Thr Gly Ala Gln Gly Pro Gln
                65                  70                  75

Gly Glu Lys Gly Glu Thr Gly Ala Gln Gly Pro Ala Gly Pro Gln
                80                  85                  90

Gly Glu Ala Gly Lys Pro Gly Glu Gln Gly Pro Ala Gly Pro Gln
                95                 100                 105

Gly Glu Ala Gly Lys Pro Gly Glu Lys
                110
```

```
<210> SEQ ID NO 15
<211> LENGTH: 186
<212> TYPE: PRT
<213> ORGANISM: artificial sequence
<220> FEATURE:
<223> OTHER INFORMATION: recombinant Scl1 protein

<400> SEQUENCE: 15

Gly Glu Lys Gly Glu Ala Gly Pro Gln Gly Glu Lys Gly Leu Pro
                 5                  10                  15

Gly Leu Thr Gly Leu Pro Gly Leu Pro Gly Glu Arg Gly Pro Arg
                20                  25                  30

Gly Pro Lys Gly Asp Arg Gly Glu Thr Gly Ala Gln Gly Pro Val
                35                  40                  45

Gly Pro Gln Gly Glu Lys Gly Glu Ala Gly Thr Pro Gly Lys Asp
                50                  55                  60

Gly Leu Arg Gly Pro Gln Gly Asp Pro Gly Ala Pro Gly Lys Asp
                65                  70                  75

Gly Ala Pro Gly Glu Lys Gly Asp Arg Gly Glu Thr Gly Ala Gln
                80                  85                  90

Gly Pro Val Gly Pro Gln Gly Glu Lys Gly Glu Ala Gly Thr Pro
                95                 100                 105

Gly Lys Asp Gly Ala Pro Gly Glu Lys Gly Glu Lys Gly Asp Arg
               110                 115                 120

Gly Glu Thr Gly Ala Thr Gly Ala Gln Gly Pro Gln Gly Glu Ala
               125                 130                 135

Gly Lys Asp Gly Ala Gln Gly Pro Val Gly Pro Gln Gly Glu Lys
               140                 145                 150

Gly Glu Thr Gly Ala Gln Gly Pro Ala Gly Pro Gln Gly Glu Lys
               155                 160                 165

Gly Glu Thr Gly Ala Gln Gly Pro Ala Gly Pro Gln Gly Glu Ala
               170                 175                 180

Gly Gln Pro Gly Glu Lys
               185

<210> SEQ ID NO 16
<211> LENGTH: 138
<212> TYPE: PRT
<213> ORGANISM: artificial sequence
<220> FEATURE:
<223> OTHER INFORMATION: recombinant Scl1 protein

<400> SEQUENCE: 16

Gly Pro Lys Gly Asp Pro Gly Pro Val Gly Pro Arg Gly Pro Glu
                 5                  10                  15

Gly Lys Pro Gly Lys Asp Gly Ala Lys Gly Asp Thr Gly Pro Arg
                20                  25                  30

Gly Glu Arg Gly Glu Gln Gly Ile Gln Gly Gln Lys Lys Ala
                35                  40                  45

Gly Glu Lys Gly Glu Lys Gly Asp Lys Gly Asp Thr Gly Glu Arg
                50                  55                  60

Gly Glu Lys Gly Asp Thr Gly Ala Thr Gly Ala Gln Gly Pro Gln
                65                  70                  75

Gly Glu Ala Gly Lys Asp Gly Ala Pro Gly Glu Lys Gly Glu Lys
                80                  85                  90

Gly Asp Thr Gly Ala Gln Gly Pro Val Gly Pro Gln Gly Glu Lys
                95                 100                 105
```

Gly Glu Thr Gly Ala Gln Gly Pro Gln Gly Glu Ala Gly Lys Pro
                110                 115                 120

Gly Glu Gln Gly Pro Ala Gly Pro Gln Gly Glu Ala Gly Lys Pro
                125                 130                 135

Gly Glu Lys

<210> SEQ ID NO 17
<211> LENGTH: 177
<212> TYPE: PRT
<213> ORGANISM: artificial sequence
<220> FEATURE:
<223> OTHER INFORMATION: recombinant Scl1 protein

<400> SEQUENCE: 17

Gly Pro Lys Gly Asp Pro Gly Pro Ala Gly Pro Arg Gly Pro Val
                  5                  10                  15

Gly Pro Glu Gly Pro Ala Gly Lys Pro Gly Lys Asp Gly Ala Gln
                 20                  25                  30

Gly Glu Arg Gly Lys Gln Gly Asn Pro Gly Pro Lys Gly Asp Lys
                 35                  40                  45

Gly Glu Asp Gly Lys Val Gly Pro Arg Gly Pro Lys Gly Asp Arg
                 50                  55                  60

Gly Glu Thr Gly Ala Gln Gly Pro Val Gly Pro Gln Gly Glu Thr
                 65                  70                  75

Gly Lys Asp Gly Ala Pro Gly Glu Lys Gly Glu Lys Gly Asp Arg
                 80                  85                  90

Gly Glu Thr Gly Ala Gln Gly Pro Val Gly Pro Gln Gly Glu Thr
                 95                 100                 105

Gly Lys Asp Gly Ala Pro Gly Glu Lys Gly Glu Lys Gly Asp Arg
                110                 115                 120

Gly Glu Thr Gly Ala Gln Gly Pro Val Gly Pro Gln Gly Glu Thr
                125                 130                 135

Gly Lys Asp Gly Ala Pro Gly Glu Lys Gly Glu Lys Gly Asp Arg
                140                 145                 150

Gly Glu Thr Gly Ala Gln Gly Pro Val Gly Pro Gln Gly Glu Lys
                155                 160                 165

Gly Glu Thr Gly Ala Gln Gly Pro Ala Gly Glu Lys
                170                 175

<210> SEQ ID NO 18
<211> LENGTH: 180
<212> TYPE: PRT
<213> ORGANISM: artificial sequence
<220> FEATURE:
<223> OTHER INFORMATION: recombinant Scl1 protein

<400> SEQUENCE: 18

Gly Pro Lys Gly Asp Pro Gly Pro Ala Gly Pro Arg Gly Pro Val
                  5                  10                  15

Gly Pro Val Gly Pro Val Gly Pro Ala Gly Lys Pro Gly Lys Asp
                 20                  25                  30

Gly Ala Gln Gly Glu Arg Gly Lys Gln Gly Asn Pro Gly Pro Lys
                 35                  40                  45

Gly Asp Lys Gly Glu Asp Gly Lys Val Gly Pro Arg Gly Pro Lys
                 50                  55                  60

Gly Asp Arg Gly Glu Thr Gly Ala Gln Gly Pro Val Gly Pro Gln
                 65                  70                  75

```
Gly Glu Thr Gly Lys Asp Gly Ala Pro Gly Glu Lys Gly Glu Lys
                80                  85                  90

Gly Asp Arg Gly Glu Thr Gly Ala Gln Gly Pro Val Gly Pro Gln
                95                 100                 105

Gly Glu Thr Gly Lys Asp Gly Ala Pro Gly Glu Lys Gly Glu Lys
               110                 115                 120

Gly Asp Arg Gly Glu Thr Gly Ala Gln Gly Pro Val Gly Pro Gln
               125                 130                 135

Gly Glu Thr Gly Lys Asp Gly Ala Pro Gly Glu Lys Gly Glu Lys
               140                 145                 150

Gly Asp Arg Gly Glu Thr Gly Ala Gln Gly Pro Val Gly Pro Gln
               155                 160                 165

Gly Glu Lys Gly Glu Thr Gly Ala Gln Gly Pro Ala Gly Glu Lys
               170                 175                 180

<210> SEQ ID NO 19
<211> LENGTH: 75
<212> TYPE: PRT
<213> ORGANISM: artificial sequence
<220> FEATURE:
<223> OTHER INFORMATION: recombinant Scl1 protein

<400> SEQUENCE: 19

Gly Glu Lys Gly Asp Pro Gly Ala Pro Gly Lys Asp Gly Ala Val
                 5                  10                  15

Gly Ala Gln Gly Pro Lys Gly Glu Lys Gly Glu Lys Gly Asp Arg
                20                  25                  30

Gly Asp Thr Gly Ala Gln Gly Pro Val Gly Pro Gln Gly Glu Lys
                35                  40                  45

Gly Glu Lys Gly Glu Lys Gly Glu Lys Gly Glu Thr Gly Glu Gln
                50                  55                  60

Gly Pro Ala Gly Pro Gln Gly Glu Ala Gly Lys Pro Gly Glu Lys
                65                  70                  75

<210> SEQ ID NO 20
<211> LENGTH: 165
<212> TYPE: PRT
<213> ORGANISM: artificial sequence
<220> FEATURE:
<223> OTHER INFORMATION: recombinant Scl1 protein

<400> SEQUENCE: 20

Gly Ile Lys Gly Asp Arg Gly Glu Thr Gly Pro Ala Gly Pro Ala
                 5                  10                  15

Gly Pro Val Gly Pro Val Gly Pro Arg Gly Pro Glu Gly Pro Glu
                20                  25                  30

Gly Lys Gln Gly Lys Pro Gly Lys Arg Gly Ala Gln Gly Ile Gln
                35                  40                  45

Gly Pro Lys Gly Asp Lys Gly Glu Thr Gly Glu Arg Gly Glu Gln
                50                  55                  60

Gly Leu Gln Gly Glu Lys Gly Asp Thr Gly Ala Ala Gly Ala Pro
                65                  70                  75

Gly Lys Asp Gly Val Gln Gly Pro Lys Gly Asp Lys Gly Glu Thr
                80                  85                  90

Gly Glu Arg Gly Glu Lys Gly Glu Ala Gly Ile Gln Gly Pro Gln
                95                 100                 105

Gly Glu Lys Gly Asp Thr Gly Ala Thr Gly Ala Gln Gly Pro Gln
               110                 115                 120
```

Gly Glu Ala Gly Lys Asp Gly Ala Pro Gly Glu Lys Gly Lys
              125                 130                 135

Gly Asp Arg Gly Glu Thr Gly Ala Gln Gly Pro Val Gly Pro Gln
              140                 145                 150

Gly Glu Lys Gly Glu Thr Gly Ala Gln Gly Pro Ala Gly Glu Lys
              155                 160                 165

<210> SEQ ID NO 21
<211> LENGTH: 114
<212> TYPE: PRT
<213> ORGANISM: artificial sequence
<220> FEATURE:
<223> OTHER INFORMATION: recombinant Scl1 protein

<400> SEQUENCE: 21

Gly Ile Lys Gly Asp Arg Gly Glu Thr Gly Pro Ala Gly Pro Ala
                5                  10                  15

Gly Pro Val Gly Pro Val Gly Pro Arg Gly Pro Glu Gly Pro Glu
               20                  25                  30

Gly Lys Gln Gly Lys Pro Gly Lys Arg Gly Ala Gln Gly Ile Gln
               35                  40                  45

Gly Pro Lys Gly Asp Lys Gly Glu Thr Gly Glu Arg Gly Glu Gln
               50                  55                  60

Gly Leu Gln Gly Glu Lys Gly Asp Thr Gly Ala Ala Gly Ala Pro
               65                  70                  75

Gly Lys Asp Gly Val Gln Gly Pro Lys Gly Asp Lys Gly Glu Thr
               80                  85                  90

Gly Ala Gln Gly Pro Val Gly Pro Gln Gly Glu Lys Gly Glu Thr
               95                 100                 105

Gly Ala Gln Gly Pro Ala Gly Glu Lys
              110

<210> SEQ ID NO 22
<211> LENGTH: 90
<212> TYPE: PRT
<213> ORGANISM: artificial sequence
<220> FEATURE:
<223> OTHER INFORMATION: recombinant Scl1 protein

<400> SEQUENCE: 22

Gly Asp Lys Gly Asp Ala Gly Pro Lys Gly Glu Arg Gly Pro Ala
                5                  10                  15

Gly Pro Gln Gly Pro Val Gly Pro Lys Gly Glu Ala Gly Lys Phe
               20                  25                  30

Gly Ala Gln Gly Pro Lys Gly Asp Lys Gly Glu Thr Gly Glu Arg
               35                  40                  45

Gly Glu Thr Gly Ala Gln Gly Pro Val Gly Pro Gln Gly Glu Lys
               50                  55                  60

Gly Glu Thr Gly Glu Gln Gly Pro Ala Gly Pro Gln Gly Glu Ala
               65                  70                  75

Gly Lys Pro Gly Glu Gln Gly Pro Ala Gly Gln Pro Gly Glu Lys
               80                  85                  90

<210> SEQ ID NO 23
<211> LENGTH: 132
<212> TYPE: PRT
<213> ORGANISM: artificial sequence
<220> FEATURE:
<223> OTHER INFORMATION: recombinant Scl1 protein -continued

<400> SEQUENCE: 23

Gly Asp Lys Gly Asp Thr Gly Pro Ala Gly Pro Gln Gly Lys Thr
                 5                  10                  15
Gly Glu Arg Gly Ala Gln Gly Pro Lys Gly Asp Arg Gly Glu Gln
             20                  25                  30
Gly Ile Gln Gly Lys Ala Gly Glu Lys Gly Glu Arg Gly Glu Lys
             35                  40                  45
Gly Asp Lys Gly Glu Thr Gly Glu Arg Gly Glu Lys Gly Glu Ala
             50                  55                  60
Gly Ile Gln Gly Pro Gln Gly Glu Lys Gly Asp Thr Gly Ala Gln
             65                  70                  75
Gly Pro Gln Gly Glu Ala Gly Lys Asp Gly Ala Pro Gly Glu Lys
             80                  85                  90
Gly Glu Lys Gly Asp Arg Gly Asp Thr Gly Ala Gln Gly Pro Val
             95                 100                 105
Gly Pro Gln Gly Glu Lys Gly Glu Thr Gly Ala Gln Gly Pro Ala
            110                 115                 120
Gly Pro Gln Gly Glu Ala Gly Gln Pro Gly Glu Lys
            125                 130

<210> SEQ ID NO 24
<211> LENGTH: 156
<212> TYPE: PRT
<213> ORGANISM: artificial sequence
<220> FEATURE:
<223> OTHER INFORMATION: recombinant Scl1 protein

<400> SEQUENCE: 24

Gly Lys Ser Gly Ile Lys Gly Asp Arg Gly Glu Thr Gly Pro Ala
                 5                  10                  15
Gly Pro Ala Gly Pro Arg Gly Pro Val Gly Pro Ala Gly Glu Ala
             20                  25                  30
Gly Lys Gln Gly Asp Arg Gly Glu Gln Gly Ile Gln Gly Pro Lys
             35                  40                  45
Gly Glu Ala Gly Ala Pro Gly Lys Asp Gly Ala Lys Gly Glu Lys
             50                  55                  60
Gly Asp Lys Gly Asp Thr Gly Glu Arg Gly Glu Lys Gly Asp Thr
             65                  70                  75
Gly Ala Gln Gly Pro Gln Gly Glu Ala Gly Lys Asp Gly Ala Pro
             80                  85                  90
Gly Lys Asp Gly Ala Pro Gly Glu Lys Gly Glu Lys Gly Asp Arg
             95                 100                 105
Gly Glu Thr Gly Ala Gln Gly Pro Val Gly Pro Gln Gly Glu Lys
            110                 115                 120
Gly Glu Thr Gly Ala Gln Gly Pro Ala Gly Pro Gln Gly Glu Ala
            125                 130                 135
Gly Lys Pro Gly Glu Gln Gly Pro Ala Gly Pro Gln Gly Glu Ala
            140                 145                 150
Gly Lys Pro Gly Glu Lys
            155

<210> SEQ ID NO 25
<211> LENGTH: 141
<212> TYPE: PRT
<213> ORGANISM: artificial sequence
<220> FEATURE:
<223> OTHER INFORMATION: recombinant Scl1 protein

```
<400> SEQUENCE: 25

Gly Pro Ala Gly Pro Ala Gly Pro Arg Gly Pro Lys Gly Glu Asp
                 5                  10                  15
Gly Lys Ala Gly Ala Pro Gly Lys Asp Gly Ala Pro Gly Lys Asp
                20                  25                  30
Gly Ala Pro Gly Lys Asp Gly Ala Pro Gly Lys Asp Gly Ala Gln
                35                  40                  45
Gly Pro Lys Gly Asp Lys Gly Glu Thr Gly Glu Arg Gly Glu Lys
                50                  55                  60
Gly Glu Thr Gly Ala Thr Gly Ala Gln Gly Pro Gln Gly Glu Ala
                65                  70                  75
Gly Lys Asp Gly Ala Pro Gly Glu Lys Gly Glu Lys Gly Asp Arg
                80                  85                  90
Gly Glu Thr Gly Ala Gln Gly Pro Val Gly Pro Gln Gly Glu Lys
                95                 100                 105
Gly Glu Thr Gly Ala Gln Gly Pro Ala Gly Pro Gln Gly Glu Ala
               110                 115                 120
Gly Gln Pro Gly Glu Gln Gly Pro Ala Gly Pro Gln Gly Glu Ala
               125                 130                 135
Gly Gln Pro Gly Glu Lys
               140

<210> SEQ ID NO 26
<211> LENGTH: 165
<212> TYPE: PRT
<213> ORGANISM: artificial sequence
<220> FEATURE:
<223> OTHER INFORMATION: recombinant Scl1 protein

<400> SEQUENCE: 26

Gly Pro Ala Gly Pro Ala Gly Pro Arg Gly Pro Lys Gly Glu Asp
                 5                  10                  15
Gly Lys Ala Gly Ala Pro Gly Lys Asp Gly Ala Pro Gly Lys Asp
                20                  25                  30
Gly Ala Pro Gly Lys Asp Gly Ala Gln Gly Pro Lys Gly Asp Lys
                35                  40                  45
Gly Glu Thr Gly Glu Arg Gly Glu Lys Gly Glu Thr Gly Ala Thr
                50                  55                  60
Gly Ala Gln Gly Pro Gln Gly Glu Ala Gly Lys Asp Gly Ala Pro
                65                  70                  75
Gly Lys Asp Gly Ala Pro Gly Lys Asp Gly Ala Gln Gly Pro Lys
                80                  85                  90
Gly Asp Lys Gly Glu Thr Gly Glu Arg Gly Glu Lys Gly Glu Thr
                95                 100                 105
Gly Ala Thr Gly Ala Gln Gly Pro Gln Gly Glu Ala Gly Lys Asp
               110                 115                 120
Gly Ala Pro Gly Glu Lys Gly Glu Lys Gly Glu Thr Gly Ala Gln
               125                 130                 135
Gly Pro Ala Gly Pro Gln Gly Glu Ala Gly Gln Pro Gly Glu Gln
               140                 145                 150
Gly Pro Ala Gly Pro Gln Gly Glu Ala Gly Gln Pro Gly Glu Lys
               155                 160                 165
```

```
<210> SEQ ID NO 27
<211> LENGTH: 129
<212> TYPE: PRT
<213> ORGANISM: artificial sequence
<220> FEATURE:
<223> OTHER INFORMATION: recombinant Scl1 protein

<400> SEQUENCE: 27

Gly Glu Lys Gly Glu Ala Gly Ile Gln Gly Pro Gln Gly Lys Ala
                  5                  10                  15

Gly Lys Asp Gly Ala Pro Gly Lys Asp Gly Ala Pro Gly Lys Asp
                 20                  25                  30

Gly Ala Val Gly Ala Gln Gly Pro Lys Gly Asp Lys Gly Asp Thr
                 35                  40                  45

Gly Glu Lys Gly Glu Thr Gly Ala Thr Gly Ala Gln Gly Pro Gln
                 50                  55                  60

Gly Glu Ala Gly Lys Asp Gly Ala Pro Gly Glu Lys Gly Glu Lys
                 65                  70                  75

Gly Asp Arg Gly Glu Thr Gly Ala Gln Gly Pro Val Gly Pro Gln
                 80                  85                  90

Gly Glu Lys Gly Glu Thr Gly Ala Gln Gly Pro Ala Gly Pro Gln
                 95                 100                 105

Gly Glu Ala Gly Lys Pro Gly Glu Gln Gly Pro Ala Gly Pro Gln
                110                 115                 120

Gly Glu Ala Gly Lys Pro Gly Glu Lys
                125

<210> SEQ ID NO 28
<211> LENGTH: 135
<212> TYPE: PRT
<213> ORGANISM: artificial sequence
<220> FEATURE:
<223> OTHER INFORMATION: recombinant Scl1 protein

<400> SEQUENCE: 28

Gly Lys Ser Gly Ile Lys Gly Asp Arg Gly Glu Ala Gly Pro Ala
                  5                  10                  15

Gly Pro Ala Gly Pro Arg Gly Glu Arg Gly Pro Ala Gly Glu Ala
                 20                  25                  30

Gly Lys Gln Gly Glu Arg Gly Glu Gln Gly Ile Gln Gly Pro Lys
                 35                  40                  45

Gly Glu Thr Gly Ala Val Gly Ala Gln Gly Pro Lys Gly Asp Lys
                 50                  55                  60

Gly Asp Thr Gly Glu Arg Gly Glu Lys Gly Asp Thr Gly Ala Thr
                 65                  70                  75

Gly Ala Gln Gly Pro Gln Gly Glu Ala Gly Lys Asp Gly Ala Pro
                 80                  85                  90

Gly Glu Lys Gly Glu Lys Gly Asp Arg Gly Glu Thr Gly Leu Gln
                 95                 100                 105

Gly Pro Val Gly Pro Gln Gly Glu Lys Gly Glu Ile Gly Ala Gln
                110                 115                 120

Gly Pro Ala Gly Pro Gln Gly Glu Ala Gly Ile Pro Gly Glu Lys
                125                 130                 135

<210> SEQ ID NO 29
<211> LENGTH: 80
<212> TYPE: PRT
<213> ORGANISM: artificial sequence
```

```
<220> FEATURE:
<223> OTHER INFORMATION: recombinant Scl2 protein

<400> SEQUENCE: 29

Gly Pro Lys Gly Pro Ala Gly Glu Lys Gly Glu Gln Gly Pro Thr
                5                   10                  15

Gly Lys Gln Gly Glu Arg Gly Glu Thr Gly Pro Ala Gly Pro Arg
                20                  25                  30

Gly Asp Lys Gly Glu Thr Gly Asp Lys Gly Ala Gln Gly Pro Val
                35                  40                  45

Gly Pro Ala Gly Lys Asp Gly Gln Asn Gly Lys Asp Gly Leu Pro
                50                  55                  60

Gly Lys Asp Gly Lys Asp Gly Gln Asn Gly Lys Asp Gly Leu Pro
                65                  70                  75

Gly Lys Asp Gly Lys
                80

<210> SEQ ID NO 30
<211> LENGTH: 159
<212> TYPE: PRT
<213> ORGANISM: artificial sequence
<220> FEATURE:
<223> OTHER INFORMATION: recombinant Scl2 protein

<400> SEQUENCE: 30

Gly Asp Gln Gly Glu Arg Gly Glu Ala Gly Pro Gln Gly Pro Ala
                5                   10                  15

Gly Gln Asp Gly Lys Ala Gly Asp Arg Gly Glu Thr Gly Pro Ala
                20                  25                  30

Gly Pro Val Gly Pro Ala Gly Pro Gln Gly Pro Arg Gly Asp Lys
                35                  40                  45

Gly Glu Thr Gly Glu Arg Gly Glu Gln Gly Pro Ala Gly Gln Asp
                50                  55                  60

Gly Lys Ala Gly Asp Arg Gly Glu Thr Gly Pro Ala Gly Pro Val
                65                  70                  75

Gly Pro Ala Gly Pro Gln Gly Pro Arg Gly Asp Lys Gly Glu Thr
                80                  85                  90

Gly Glu Arg Gly Glu Gln Gly Pro Ala Gly Gln Asp Gly Lys Asp
                95                  100                 105

Gly Asp Arg Gly Glu Thr Gly Pro Ala Gly Pro Val Gly Pro Ala
                110                 115                 120

Gly Lys Asp Gly Gln Asp Gly Lys Asp Gly Leu Pro Gly Lys Asp
                125                 130                 135

Gly Lys Asp Gly Gln Asp Gly Lys Asp Gly Leu Pro Gly Lys Asp
                140                 145                 150

Gly Lys Asp Gly Gln Pro Gly Lys Pro
                155

<210> SEQ ID NO 31
<211> LENGTH: 348
<212> TYPE: PRT
<213> ORGANISM: artificial sequence
<220> FEATURE:
<223> OTHER INFORMATION: recombinant Scl2 protein
```

-continued

```
<400> SEQUENCE: 31

Gly Gln Asp Gly Asp Arg Gly Glu Ala Gly Pro Ala Gly Pro Arg
                 5                  10                  15
Gly Glu Ala Gly Pro Ala Gly Pro Arg Gly Glu Ala Gly Lys Asp
                20                  25                  30
Gly Ala Lys Gly Asp Arg Gly Glu Ala Gly Pro Ala Gly Pro Arg
                35                  40                  45
Gly Glu Ala Gly Lys Asp Gly Ala Lys Gly Asp Arg Gly Glu Ala
                50                  55                  60
Gly Pro Ala Gly Pro Arg Gly Glu Ala Gly Lys Asp Gly Ala Lys
                65                  70                  75
Gly Asp Arg Gly Glu Ala Gly Pro Ala Gly Pro Arg Gly Glu Ala
                80                  85                  90
Gly Lys Asp Gly Ala Lys Gly Asp Arg Gly Glu Ala Gly Pro Ala
                95                 100                 105
Gly Pro Arg Gly Glu Ala Gly Pro Ala Gly Pro Arg Gly Glu Ala
               110                 115                 120
Gly Pro Ala Gly Pro Arg Gly Glu Ala Gly Pro Ala Gly Pro Arg
               125                 130                 135
Gly Glu Ala Gly Lys Asp Gly Ala Lys Gly Asp Arg Gly Glu Ala
               140                 145                 150
Gly Pro Ala Gly Pro Arg Gly Glu Ala Gly Lys Asp Gly Ala Lys
               155                 160                 165
Gly Asp Arg Gly Glu Ala Gly Pro Ala Gly Pro Arg Gly Glu Ala
               170                 175                 180
Gly Lys Asp Gly Ala Lys Gly Asp Arg Gly Glu Ala Gly Pro Ala
               185                 190                 195
Gly Pro Arg Gly Glu Ala Gly Pro Ala Gly Pro Arg Gly Glu Ala
               200                 205                 210
Gly Lys Asp Gly Ala Lys Gly Asp Arg Gly Glu Ala Gly Pro Ala
               215                 220                 225
Gly Pro Arg Gly Glu Ala Gly Lys Asp Gly Ala Lys Gly Asp Arg
               230                 235                 240
Gly Glu Ala Gly Pro Ala Gly Pro Arg Gly Glu Ala Gly Lys Asp
               245                 250                 255
Gly Ala Lys Gly Asp Arg Gly Glu Ala Gly Pro Ala Gly Pro Arg
               260                 265                 270
Gly Glu Ala Gly Lys Asp Gly Ala Lys Gly Asp Arg Gly Glu Ala
               275                 280                 285
Gly Pro Ala Gly Pro Arg Gly Glu Ala Gly Lys Asp Gly Ala Lys
               290                 295                 300
Gly Asp Arg Gly Glu Ala Gly Pro Ala Gly Pro Arg Gly Glu Ala
               305                 310                 315
Gly Lys Asp Gly Ala Lys Gly Asp Arg Gly Glu Ala Gly Pro Ala
               320                 325                 330
Gly Pro Arg Gly Glu Ala Gly Pro Ala Gly Lys Asp Gly Gln Pro
               335                 340                 345
Gly Lys Pro

<210> SEQ ID NO 32
<211> LENGTH: 117
<212> TYPE: PRT
<213> ORGANISM: artificial sequence
```

-continued

```
<220> FEATURE:
<223> OTHER INFORMATION: recombinant Scl2 protein

<400> SEQUENCE: 32

Gly Asp Lys Gly Glu Pro Gly Ala Gln Gly Pro Ala Gly Pro Arg
                 5                  10                  15

Gly Glu Thr Gly Pro Ala Gly Glu Arg Gly Glu Lys Gly Glu Pro
             20                  25                  30

Gly Thr Gln Gly Ala Lys Gly Asp Arg Gly Glu Thr Gly Pro Ala
         35                  40                  45

Gly Pro Arg Gly Asp Lys Gly Glu Lys Gly Glu Gln Gly Pro Ala
     50                  55                  60

Gly Lys Asp Gly Glu Arg Gly Pro Ile Gly Pro Ala Gly Lys Asp
 65                  70                  75

Gly Gln Asn Gly Lys Asp Gly Leu Pro Gly Lys Asp Gly Lys Asp
             80                  85                  90

Gly Gln Asn Gly Lys Asp Gly Leu Pro Gly Lys Asp Gly Lys Asp
         95                 100                 105

Gly Gln Asp Gly Lys Asp Gly Leu Pro Gly Lys Pro
    110                 115

<210> SEQ ID NO 33
<211> LENGTH: 174
<212> TYPE: PRT
<213> ORGANISM: artificial sequence
<220> FEATURE:
<223> OTHER INFORMATION: recombinant Scl2 protein

<400> SEQUENCE: 33

Gly Asp Gln Gly Asn Pro Gly Glu Arg Gly Glu Thr Gly Pro Ala
                 5                  10                  15

Gly Pro Ala Gly Pro Val Gly Pro Val Gly Pro Arg Gly Glu Arg
             20                  25                  30

Gly Glu Ala Gly Pro Ala Gly Gln Asp Gly Lys Ala Gly Asp Arg
         35                  40                  45

Gly Glu Thr Gly Pro Ala Gly Pro Val Gly Pro Arg Gly Asp Lys
     50                  55                  60

Gly Glu Lys Gly Glu Gln Gly Pro Ala Gly Lys Asp Gly Leu Pro
 65                  70                  75

Gly Lys Asp Gly Lys Asp Gly Gln Asn Gly Lys Asp Gly Leu Pro
             80                  85                  90

Gly Lys Asp Gly Lys Asp Gly Gln Asp Gly Lys Asp Gly Leu Pro
         95                 100                 105

Gly Lys Asp Gly Lys Asp Gly Gln Asp Gly Lys Asp Gly Leu Pro
    110                 115                 120

Gly Lys Asp Gly Lys Asp Gly Gln Asn Gly Lys Asp Gly Leu Pro
    125                 130                 135

Gly Lys Asp Gly Lys Asp Gly Gln Asn Gly Lys Asp Gly Leu Pro
        140                 145                 150

Gly Lys Asp Gly Lys Asp Gly Gln Asn Gly Lys Asp Gly Leu Pro
    155                 160                 165

Gly Lys Asp Gly Gln Pro Gly Lys Pro
    170
```

<210> SEQ ID NO 34
<211> LENGTH: 183
<212> TYPE: PRT
<213> ORGANISM: artificial sequence
<220> FEATURE:
<223> OTHER INFORMATION: recombinant Scl2 protein

<400> SEQUENCE: 34

Gly Glu Lys Gly Glu Arg Gly Pro Val Gly Pro Ala Gly Pro Gln
                 5                  10                  15

Gly Leu Gln Gly Thr Lys Gly Asp Arg Gly Glu Thr Gly Glu Gln
                20                  25                  30

Gly Gln Arg Gly Glu Thr Gly Pro Ala Gly Pro Gln Gly Pro Ala
                35                  40                  45

Gly Pro Val Gly Pro Ala Gly Lys Asp Gly Glu Ala Gly Ala Gln
                50                  55                  60

Gly Pro Val Gly Pro Ala Gly Lys Asp Gly Gln Asp Gly Lys Asp
                65                  70                  75

Gly Leu Pro Gly Lys Asp Gly Gln Asn Gly Lys Asp Gly Leu Pro
                80                  85                  90

Gly Lys Asp Gly Lys Asp Gly Gln Asp Gly Lys Asp Gly Leu Pro
                95                  100                 105

Gly Lys Asp Gly Lys Asp Gly Leu Pro Gly Lys Asp Gly Lys Asp
                110                 115                 120

Gly Gln Asn Gly Lys Asp Gly Gln Asn Gly Lys Asp Gly Leu Pro
                125                 130                 135

Gly Lys Asp Gly Gln Asn Gly Lys Asp Gly Leu Pro Gly Lys Asp
                140                 145                 150

Gly Gln Asn Gly Lys Asp Gly Lys Asp Gly Leu Pro Gly Lys Asp
                155                 160                 165

Gly Lys Asp Gly Leu Pro Gly Lys Asp Gly Lys Asp Gly Gln Pro
                170                 175                 180

Gly Lys Pro

<210> SEQ ID NO 35
<211> LENGTH: 216
<212> TYPE: PRT
<213> ORGANISM: artificial sequence
<220> FEATURE:
<223> OTHER INFORMATION: recombinant Scl2 protein

<400> SEQUENCE: 35

Gly Glu Lys Gly Glu Arg Gly Pro Val Gly Pro Ala Gly Pro Gln
                 5                  10                  15

Gly Leu Gln Gly Thr Lys Gly Asp Arg Gly Glu Thr Gly Glu Gln
                20                  25                  30

Gly Gln Arg Gly Glu Thr Gly Pro Ala Gly Pro Gln Gly Pro Ala
                35                  40                  45

Gly Pro Val Gly Pro Ala Gly Lys Asp Gly Gln Asp Gly Lys Asp
                50                  55                  60

Gly Leu Pro Gly Lys Asp Gly Gln Asn Gly Lys Asp Gly Leu Pro
                65                  70                  75

Gly Lys Asp Gly Gln Asn Gly Lys Asp Gly Leu Pro Gly Lys Asp
                80                  85                  90

Gly Lys Asp Gly Gln Asp Gly Lys Asp Gly Leu Pro Gly Lys Asp
                95                  100                 105

```
Gly Lys Asp Gly Leu Pro Gly Lys Asp Gly Pro Asn Gly Lys Asp
            110                 115                 120

Gly Leu Pro Gly Lys Asp Gly Lys Asp Gly Gln Asp Gly Lys Asp
            125                 130                 135

Gly Leu Pro Gly Lys Asp Gly Lys Asp Gly Leu Pro Gly Lys Asp
            140                 145                 150

Gly Lys Asp Gly Gln Asn Gly Lys Asp Gly Gln Asn Gly Lys Asp
            155                 160                 165

Gly Leu Pro Gly Lys Asp Gly Gln Asn Gly Lys Asp Gly Leu Pro
            170                 175                 180

Gly Lys Asp Gly Lys Asp Gly Gln Asp Gly Lys Asp Gly Leu Pro
            185                 190                 195

Gly Lys Asp Gly Lys Asp Gly Leu Pro Gly Lys Asp Gly Lys Asp
            200                 205                 210

Gly Gln Pro Gly Lys Pro
            215

<210> SEQ ID NO 36
<211> LENGTH: 234
<212> TYPE: PRT
<213> ORGANISM: artificial sequence
<220> FEATURE:
<223> OTHER INFORMATION: recombinant Scl2 protein

<400> SEQUENCE: 36

Gly Gln Asp Gly Arg Asn Gly Glu Arg Gly Glu Gln Gly Pro Thr
            5                   10                  15

Gly Pro Thr Gly Pro Ala Gly Pro Arg Gly Leu Gln Gly Leu Gln
            20                  25                  30

Gly Glu Arg Gly Glu Gln Gly Pro Thr Gly Pro Ala Gly Pro Arg
            35                  40                  45

Gly Leu Gln Gly Glu Arg Gly Glu Gln Gly Pro Thr Gly Leu Ala
            50                  55                  60

Gly Lys Ala Gly Glu Ala Gly Ala Lys Gly Glu Thr Gly Pro Ala
            65                  70                  75

Gly Pro Gln Gly Pro Arg Gly Glu Gln Gly Pro Gln Gly Leu Pro
            80                  85                  90

Gly Lys Asp Gly Glu Ala Gly Ala Gln Gly Pro Ala Gly Pro Met
            95                  100                 105

Gly Pro Ala Gly Glu Arg Gly Glu Lys Gly Glu Pro Gly Thr Gln
            110                 115                 120

Gly Ala Lys Gly Asp Arg Gly Glu Thr Gly Pro Val Gly Pro Arg
            125                 130                 135

Gly Glu Arg Gly Glu Ala Gly Pro Ala Gly Lys Asp Gly Glu Arg
            140                 145                 150

Gly Pro Val Gly Pro Ala Gly Lys Asp Gly Gln Asn Gly Gln Asp
            155                 160                 165

Gly Leu Pro Gly Lys Asp Gly Lys Asp Gly Gln Asn Gly Lys Asp
            170                 175                 180

Gly Leu Pro Gly Lys Asp Gly Lys Asp Gly Gln Asn Gly Lys Asp
            185                 190                 195

Gly Leu Pro Gly Lys Asp Gly Lys Asp Gly Gln Asp Gly Lys Asp
            200                 205                 210
```

Gly Leu Pro Gly Lys Asp Gly Lys Asp Gly Leu Pro Gly Lys Asp
            215                 220                 225

Gly Lys Asp Gly Gln Pro Gly Lys Pro
            230

<210> SEQ ID NO 37
<211> LENGTH: 237
<212> TYPE: PRT
<213> ORGANISM: artificial sequence
<220> FEATURE:
<223> OTHER INFORMATION: recombinant Scl2 protein

<400> SEQUENCE: 37

Gly Gln Asp Gly Arg Asn Gly Glu Arg Gly Glu Gln Gly Pro Thr
              5                  10                  15

Gly Pro Thr Gly Pro Ala Gly Pro Arg Gly Leu Gln Gly Leu Gln
             20                  25                  30

Gly Leu Gln Gly Glu Arg Gly Glu Gln Gly Pro Thr Gly Pro Ala
             35                  40                  45

Gly Pro Arg Gly Leu Gln Gly Glu Arg Gly Glu Gln Gly Pro Thr
             50                  55                  60

Gly Leu Ala Gly Lys Ala Gly Glu Ala Gly Ala Lys Gly Glu Thr
             65                  70                  75

Gly Pro Ala Gly Pro Gln Gly Pro Arg Gly Glu Gln Gly Pro Gln
             80                  85                  90

Gly Leu Pro Gly Lys Asp Gly Glu Ala Gly Ala Gln Gly Pro Ala
             95                 100                 105

Gly Pro Met Gly Pro Ala Gly Glu Arg Gly Glu Lys Gly Glu Pro
            110                 115                 120

Gly Thr Gln Gly Ala Lys Gly Asp Arg Gly Glu Thr Gly Pro Val
            125                 130                 135

Gly Pro Arg Gly Glu Arg Gly Glu Ala Gly Pro Ala Gly Lys Asp
            140                 145                 150

Gly Glu Arg Gly Pro Val Gly Pro Ala Gly Lys Asp Gly Gln Asn
            155                 160                 165

Gly Gln Asp Gly Leu Pro Gly Lys Asp Gly Lys Asp Gly Gln Asn
            170                 175                 180

Gly Lys Asp Gly Leu Pro Gly Lys Asp Gly Lys Asp Gly Gln Asn
            185                 190                 195

Gly Lys Asp Gly Leu Pro Gly Lys Asp Gly Lys Asp Gly Gln Asp
            200                 205                 210

Gly Lys Asp Gly Leu Pro Gly Lys Asp Gly Lys Asp Gly Leu Pro
            215                 220                 225

Gly Lys Asp Gly Lys Asp Gly Gln Pro Gly Lys Pro
            230                 235

<210> SEQ ID NO 38
<211> LENGTH: 111
<212> TYPE: PRT
<213> ORGANISM: artificial sequence
<220> FEATURE:
<223> OTHER INFORMATION: recombinant Scl2 protein

<400> SEQUENCE: 38

Gly Lys Asp Gly Glu Thr Gly Pro Ala Gly Pro Thr Gly Pro Ala
              5                  10                  15

Gly Ala Lys Gly Glu Thr Gly Pro Ala Gly Pro Val Gly Pro Arg
             20                  25                  30

-continued

Gly Asp Lys Gly Glu Lys Gly Gln Gly Pro Ala Gly Lys Asp
                35                  40                  45

Gly Leu Pro Gly Lys Asp Gly Lys Asp Gly Gln Asn Gly Lys Asp
            50                  55                  60

Gly Leu Pro Gly Lys Asp Gly Lys Asp Gly Gln Asn Gly Lys Asp
            65                  70                  75

Gly Leu Pro Gly Lys Asp Gly Lys Asp Gly Gln Asn Gly Lys Asp
            80                  85                  90

Gly Leu Pro Gly Lys Asp Gly Lys Asp Gly Lys Asp Gly Lys Asp
            95                 100                 105

Gly Gln Pro Gly Lys Pro
            110

<210> SEQ ID NO 39
<211> LENGTH: 111
<212> TYPE: PRT
<213> ORGANISM: artificial sequence
<220> FEATURE:
<223> OTHER INFORMATION: recombinant Scl2 protein

<400> SEQUENCE: 39

Gly Lys Asp Gly Glu Thr Gly Pro Ala Gly Pro Thr Gly Pro Ala
                5                  10                  15

Gly Ala Lys Gly Glu Thr Gly Pro Ala Gly Pro Val Gly Pro Arg
            20                  25                  30

Gly Asp Lys Gly Glu Lys Gly Glu Gln Gly Pro Ala Gly Lys Asp
            35                  40                  45

Gly Leu Pro Gly Lys Asp Gly Lys Asp Gly Gln Asn Gly Lys Asp
            50                  55                  60

Gly Leu Pro Gly Lys Asp Gly Lys Asp Gly Gln Asn Gly Lys Asp
            65                  70                  75

Gly Leu Pro Gly Lys Asp Gly Lys Asp Gly Gln Asn Gly Lys Asp
            80                  85                  90

Gly Leu Pro Gly Lys Asp Gly Lys Asp Gly Lys Asp Gly Lys Asp
            95                 100                 105

Gly Gln Pro Gly Lys Pro
            110

<210> SEQ ID NO 40
<211> LENGTH: 222
<212> TYPE: PRT
<213> ORGANISM: artificial sequence
<220> FEATURE:
<223> OTHER INFORMATION: recombinant Scl2 protein

<400> SEQUENCE: 40

Gly Asp Gln Gly Glu Pro Gly Glu Pro Gly Glu Pro Gly Glu Arg
                5                  10                  15

Gly Pro Arg Gly Glu Val Gly Pro Ala Gly Gln Gly Pro Val
            20                  25                  30

Gly Pro Val Gly Pro Ala Gly Lys Asp Gly Thr Gln Gly Pro Arg
            35                  40                  45

Gly Asp Lys Gly Glu Pro Gly Glu Gln Gly Gln Arg Gly Glu Thr
            50                  55                  60

Gly Pro Ala Gly Pro Gln Gly Pro Ala Gly Pro Val Gly Pro Ala
            65                  70                  75

Gly Lys Asp Gly Thr Gln Gly Pro Arg Gly Asp Lys Gly Glu Thr
            80                  85                  90

```
Gly Glu Gln Gly Gln Arg Gly Glu Val Gly Pro Ala Gly Pro Gln
                 95                 100                 105

Gly Pro Val Gly Pro Val Gly Pro Ala Gly Lys Asp Gly Ala Lys
            110                 115                 120

Gly Asp Arg Gly Glu Thr Gly Pro Ala Gly Pro Ala Gly Lys Asp
            125                 130                 135

Gly Glu Ala Gly Ala Gln Gly Pro Met Gly Pro Ala Gly Pro Gln
            140                 145                 150

Gly Pro Arg Gly Asp Lys Gly Glu Thr Gly Asp Lys Gly Glu Gln
            155                 160                 165

Gly Pro Ala Gly Lys Asp Gly Glu Arg Gly Pro Val Gly Pro Ala
            170                 175                 180

Gly Lys Asp Gly Gln Asp Gly Leu Pro Gly Lys Asp Gly Lys Asp
            185                 190                 195

Gly Gln Asp Gly Lys Asp Gly Leu Pro Gly Lys Asp Gly Lys Asp
            200                 205                 210

Gly Gln Asp Gly Lys Asp Gly Leu Pro Gly Lys Pro
            215                 220

<210> SEQ ID NO 41
<211> LENGTH: 237
<212> TYPE: PRT
<213> ORGANISM: artificial sequence
<220> FEATURE:
<223> OTHER INFORMATION: recombinant Scl2 protein

<400> SEQUENCE: 41

Gly Pro Arg Gly Asp Lys Gly Glu Thr Gly Glu Gln Gly Pro Arg
              5                  10                  15

Gly Ala Gln Gly Pro Ala Gly Pro Gln Gly Pro Val Gly Pro Ala
             20                  25                  30

Gly Lys Asp Gly Thr Gln Gly Pro Arg Gly Asp Lys Gly Glu Thr
             35                  40                  45

Gly Glu Gln Gly Pro Arg Gly Ala Gln Gly Pro Ala Gly Pro Gln
             50                  55                  60

Gly Pro Val Gly Pro Ala Gly Lys Asp Gly Thr Gln Gly Pro Arg
             65                  70                  75

Gly Asp Lys Gly Glu Thr Gly Glu Gln Gly Pro Arg Gly Ala Gln
             80                  85                  90

Gly Pro Ala Gly Pro Gln Gly Pro Met Gly Pro Ala Gly Glu Arg
             95                 100                 105

Gly Glu Lys Gly Glu Pro Gly Thr Gln Gly Ala Lys Gly Asp Arg
            110                 115                 120

Gly Glu Thr Gly Pro Ala Gly Val Gly Pro Arg Gly Asp Lys
            125                 130                 135

Gly Glu Thr Gly Ala Lys Gly Glu Gln Gly Pro Ala Gly Lys Asp
            140                 145                 150

Gly Lys Ala Gly Glu Arg Gly Pro Val Gly Pro Ala Gly Lys Asp
            155                 160                 165

Gly Gln Asn Gly Lys Asp Gly Leu Pro Gly Lys Asp Gly Lys Asp
            170                 175                 180

Gly Gln Asn Gly Lys Asp Gly Leu Pro Gly Lys Asp Gly Lys Asp
            185                 190                 195

Gly Gln Asn Gly Lys Asp Gly Leu Pro Gly Lys Asp Gly Lys Asp
            200                 205                 210
```

```
Gly Gln Asn Gly Lys Asp Gly Leu Pro Gly Lys Asp Gly Lys Asp
                215                 220                 225

Gly Lys Asp Gly Lys Asp Gly Gln Pro Gly Lys Pro
                230                 235
```

<210> SEQ ID NO 42
<211> LENGTH: 198
<212> TYPE: PRT
<213> ORGANISM: artificial sequence
<220> FEATURE:
<223> OTHER INFORMATION: recombinant Scl2 protein

<400> SEQUENCE: 42

```
Gly Ala Lys Gly Glu Ala Gly Pro Ala Gly Pro Lys Gly Pro Ala
                  5                  10                  15

Gly Glu Lys Gly Glu Arg Gly Glu Thr Gly Pro Ala Gly Pro Ala
                 20                  25                  30

Gly Lys Asp Gly Glu Ala Gly Ala Gln Gly Pro Met Gly Pro Ala
                 35                  40                  45

Gly Pro Gln Gly Pro Arg Gly Asp Lys Gly Glu Thr Gly Asp Lys
                 50                  55                  60

Gly Asp Gln Gly Pro Ala Gly Lys Asp Gly Asp Arg Gly Pro Val
                 65                  70                  75

Gly Pro Gln Gly Pro Gln Gly Glu Thr Gly Pro Ala Gly Pro Ala
                 80                  85                  90

Gly Lys Asp Gly Glu Lys Gly Glu Pro Gly Pro Arg Gly Glu Ala
                 95                 100                 105

Gly Ala Gln Gly Pro Ala Gly Pro Gln Gly Pro Arg Gly Asp Lys
                110                 115                 120

Gly Glu Thr Gly Asp Lys Gly Glu Gln Gly Pro Ala Gly Lys Asp
                125                 130                 135

Gly Glu Arg Gly Pro Val Gly Pro Ala Gly Lys Asp Gly Gln Asn
                140                 145                 150

Gly Lys Asp Gly Leu Pro Gly Lys Asp Gly Lys Asp Gly Gln Asp
                155                 160                 165

Gly Lys Asp Gly Leu Pro Gly Lys Asp Gly Lys Asp Gly Gln Asp
                170                 175                 180

Gly Lys Asp Gly Leu Pro Gly Lys Asp Gly Lys Ser Gly Gln Pro
                185                 190                 195

Gly Lys Pro
```

<210> SEQ ID NO 43
<211> LENGTH: 237
<212> TYPE: PRT
<213> ORGANISM: artificial sequence
<220> FEATURE:
<223> OTHER INFORMATION: collagen-like region of p163

<400> SEQUENCE: 43

```
Gly Gln Asp Gly Arg Asn Gly Glu Arg Gly Glu Gln Gly Pro Thr
                  5                  10                  15

Gly Pro Thr Gly Pro Ala Gly Pro Arg Gly Leu Gln Gly Leu Gln
                 20                  25                  30

Gly Leu Gln Gly Glu Arg Gly Glu Gln Gly Pro Thr Gly Pro Ala
                 35                  40                  45

Gly Pro Arg Gly Leu Gln Gly Glu Arg Gly Glu Gln Gly Pro Thr
                 50                  55                  60
```

```
Gly Leu Ala Gly Lys Ala Gly Glu Ala Gly Ala Lys Gly Thr
                65                  70                  75

Gly Pro Ala Gly Pro Gln Gly Pro Arg Gly Glu Gln Gly Pro Gln
            80                  85                  90

Gly Leu Pro Gly Lys Asp Gly Glu Ala Gly Ala Gln Gly Pro Ala
            95                  100                 105

Gly Pro Met Gly Pro Ala Gly Glu Arg Gly Glu Lys Gly Glu Pro
            110                 115                 120

Gly Thr Gln Gly Ala Lys Gly Asp Arg Gly Glu Thr Gly Pro Val
            125                 130                 135

Gly Pro Arg Gly Glu Arg Gly Glu Ala Gly Pro Ala Gly Lys Asp
            140                 145                 150

Gly Glu Arg Gly Pro Val Gly Pro Ala Gly Lys Asp Gly Gln Asn
            155                 160                 165

Gly Gln Asp Gly Leu Pro Gly Lys Asp Gly Lys Asp Gly Gln Asn
            170                 175                 180

Gly Lys Asp Gly Leu Pro Gly Lys Asp Gly Lys Asp Gly Gln Asn
            185                 190                 195

Gly Lys Asp Gly Leu Pro Gly Lys Asp Gly Lys Asp Gly Gln Asp
            200                 205                 210

Gly Lys Asp Gly Leu Pro Gly Lys Asp Gly Lys Asp Gly Leu Pro
            215                 220                 225

Gly Lys Asp Gly Lys Asp Gly Gln Pro Gly Lys Pro
            230                 235

<210> SEQ ID NO 44
<211> LENGTH: 313
<212> TYPE: PRT
<213> ORGANISM: artificial sequence
<220> FEATURE:
<223> OTHER INFORMATION: p176

<400> SEQUENCE: 44

Glu Asp Ser Glu Thr Ala Thr Ala Arg Thr Lys Leu Leu Glu Lys
                5                   10                  15

Leu Thr Glu Leu Arg Ser Gln Ser Gln Asp Arg Val Pro Gln Thr
            20                  25                  30

Ser Asp Ile Thr Gln Ala Tyr Thr Leu Trp Gly Thr Ser Tyr Asp
            35                  40                  45

Ser Val Glu Leu Tyr Lys Tyr Leu Gln Gln Ile Glu Glu Tyr Leu
            50                  55                  60

Gln Lys Gln Lys Tyr His Glu Glu Gln Trp Lys Lys Glu Ile Thr
            65                  70                  75

Asp Gly Leu Lys Ser Gly Ala Leu Arg Gly Glu Lys Gly Glu Ala
            80                  85                  90

Gly Pro Gln Gly Glu Lys Gly Leu Pro Gly Leu Thr Gly Leu Pro
            95                  100                 105

Gly Leu Pro Gly Glu Arg Gly Pro Arg Gly Pro Lys Gly Asp Arg
            110                 115                 120

Gly Glu Thr Gly Ala Gln Gly Pro Val Gly Pro Gln Gly Glu Lys
            125                 130                 135

Gly Glu Ala Gly Thr Pro Gly Lys Asp Gly Leu Arg Gly Pro Gln
            140                 145                 150

Gly Asp Pro Gly Ala Pro Gly Lys Asp Gly Ala Pro Gly Glu Lys
            155                 160                 165
```

```
-continued

Gly Asp Arg Gly Glu Thr Gly Ala Gln Gly Pro Val Gly Pro Gln
                170                 175                 180

Gly Glu Lys Gly Glu Ala Gly Thr Pro Gly Lys Asp Gly Ala Pro
                185                 190                 195

Gly Glu Lys Gly Glu Lys Gly Asp Arg Gly Glu Thr Gly Ala Thr
                200                 205                 210

Gly Ala Gln Gly Pro Gln Gly Glu Ala Gly Lys Asp Gly Ala Gln
                215                 220                 225

Gly Pro Val Gly Pro Gln Gly Glu Lys Gly Glu Thr Gly Ala Gln
                230                 235                 240

Gly Pro Ala Gly Pro Gln Gly Glu Lys Gly Glu Thr Gly Ala Gln
                245                 250                 255

Gly Pro Ala Gly Pro Gln Gly Glu Ala Gly Gln Pro Gly Glu Lys
                260                 265                 270

Ala Pro Glu Lys Ser Pro Glu Val Thr Pro Thr Pro Glu Met Pro
                275                 280                 285

Glu Gln Pro Gly Glu Gln Ala Pro Glu Lys Ser Lys Glu Val Thr
                290                 295                 300

Pro Ala Pro Glu Lys Trp Ser His Pro Gln Phe Glu Lys
                305                 310

<210> SEQ ID NO 45
<211> LENGTH: 8
<212> TYPE: PRT
<213> ORGANISM: artificial sequence
<220> FEATURE:
<223> OTHER INFORMATION: Strep-tag II

<400> SEQUENCE: 45

Trp Ser His Pro Gln Phe Glu Lys
                5

<210> SEQ ID NO 46
<211> LENGTH: 7
<212> TYPE: PRT
<213> ORGANISM: artificial sequence
<220> FEATURE:
<223> OTHER INFORMATION: peptide on gram positive bacteria
      that binds fibernectin

<400> SEQUENCE: 46

Met Ser Cys Arg Ala Met Met
                5
```

PROKARYOTIC COLLAGEN-LIKE PROTEINS AND USES THEREOF

CROSS-REFERENCE TO RELATED APPLICATION

This non-provisional application claims benefit of provisional U.S. Ser. No. 60/464,816, filed Apr. 23, 2003, now abandoned.

FEDERAL FUNDING LEGEND

This invention was produced in part using funds obtained through grants AR44415 and AI50666 from the National Institutes of Health. Consequently, the federal government has certain rights in this invention.

BACKGROUND OF THE INVENTION

1. Field of the Invention

The invention relates generally to protein molecular biology and microbiology. More specifically, the present invention relates to recombinant prokaryotic collagen-like or triple helical proteins and methods of producing collagen-like materials in prokaryotic organisms.

2. Description of the Related Art

Collagens are abundant extracellular matrix proteins that are essential structural elements of connective tissues in human and animals. The vertebrate collagens are classified into 19 types that are grouped in two major categories known as fibrillar, i.e., types I–III, V, and XI and nonfibrillar, i.e., types IV, VI–X, and XII–XIX collagens. In addition, collagens can alter cell function by interacting with specific cellular receptors (1). The repeating sequence Gly-Xaa-Yaa (GXY), in which a sterically small glycine residue occupies every third position, because only glycine is small enough to be accommodated at the center of the triple helix and in which X is often occupied by proline and Y by hydroxyproline, is a unique feature of the collagen polypeptide (2–4). Proline hydroxylation together with glycosylation of the polypeptide, are essential factors in stabilizing the collagen triple helix and the formation of collagen networks, respectively.

Long tracks of repeated GXY sequences fold into left-handed polyproline type II-like chains and three such chains cooperatively twist around a central axis to form a right-handed rope-like superhelix (2,5–7). The three chains are linked by hydrogen bonds between the backbone group, —NH (Gly) and the backbone carbonyl group of residue X of another chain, and by water-mediated interactions. In humans, mutations that affect collagen triple helix formation and fiber assembly have serious pathological consequences often leading to death.

In some collagen types, the C-terminal and N-terminal propeptides are removed during secretion from cells (7–9). The resulting mature collagen molecules are deposited in the extracellular matrix in the form of fibers, networks and beaded filaments (8). One group of mammalian proteins has collageneous subdomains, but they are not conventional collagens. This group includes several proteins that fulfill rudimentary host defense functions, including complement factor Clq (10) and some mammalian lectins (11). These proteins form characteristic lollipop-like structures with stalks made from their collagenous domains and globular heads made from the non-collagenous regions.

Collagen-like molecules also have been found in lower eukaryotes, such as mussels, worms, and sponges (12), and collagen-like sequences have been deduced from analyses of the genomes of prokaryotes (13–16). Moreover, DNA tracks encoding collagen-like sequences have been found in the genomes of bacteria and phages. However, these organisms appear to lack proline hydroxylases and since hydroxyproline in the past has been considered a critical residue for triple helix formation, it is unclear if the prokaryotic GXY repeated motifs result in proteins that can form stable collagen-like triple helices. Recent studies of model synthetic peptides demonstrate that a GXY sequence with certain so called "guest" residues other than proline and hydroxyproline in the X and Y positions are capable of forming a stable triple helix. Furthermore, type I collagen expressed in tobacco plants, although virtually unhydroxylated, does form a triple helix.

Collagens can act as cell adhesion substrates, organize the cytoskeleton and promote cellular contractility and motility by their ability to interact with integrins and cellular adhesion receptors (17–19). Integrins are large glycoproteins and are expressed as $\alpha\beta$ heterodimers on the cell surface (17, 19–21). There are 14 distinct $\alpha$ subunits and eight $\beta$ subunits in mammals that combine to form 24 known heterodimers (22–23).

There are four major subunits of integrin that act as collagen receptors, including $\alpha_1\beta_1$ and $\alpha_2\beta_1$, which are the most widely expressed, and $\alpha_{10}b_1$ and $\alpha_{11}b_1$, which are more distinctly distributed (24–26). While $\alpha_1\beta_1$ and $\alpha_2\beta_1$ favor Col IV and Col I, respectively (27–28), each of these heterodimers is known to bind to both types of collagens (30). Even though $\alpha_1\beta_1$ and $\alpha_2\beta_1$ integrins interact with several types of collagen proteins, they appear to possess distinct recognition abilities. For example, $\alpha_1\beta_1$ integrin can bind to type XIII collagen, whereas $\alpha_2b_1$ integrin cannot (30).

The extracellular domains of integrins interact with extracellular matrix (ECM) proteins in a metal ion-dependent manner (31). Recent studies demonstrate that the so called I-domains of the $\alpha$ subunits of $\alpha_1\beta_1$, $\alpha_2\beta_1$, $\alpha_{10}\beta_1$, and $\alpha_{11}\beta_1$ integrins mediate the interactions of these ECM receptors with collagens and control cell adhesion activity (32–34). The cytoplasmic segments of integrins interact with elements of the cytoskeleton and the signaling molecules, and can trigger intracellular signaling pathways. For example, integrin ligation induces tyrosine phosphorylation of FAK, PYK2, p72SYK, ILK-1, CAS, paxillin, SRC/FYN, and Shc (35–40). Furthermore, signaling events mediated by these molecules are important in an array of biological processes, including cell-migration, cell proliferation and differentiation, angiogenesis, and cancer cell metastasis (35, 38,40).

Denatured collagen, gelatin, is widely used in the cosmetic and pharmacological industries, for example, as a pill coating or as a stabilizer. Collagen is usually obtained from bovine skin or other animal products. Unfortunately, these animal protein products can be contaminated by viruses and prions, such as occurs in mad cow disease. Mammalian collagens have been shown to induce autoimmune diseases in animal models. An artificial collagen product would be a desirable alternative to animal based collagen products.

The Streptococcal collagen-like proteins, Scl1 and Scl2, also known as ScIA and ScIB, are the best-characterized members of the prokaryotic family of collagen-like proteins (41–45). The two related proteins contain long segments of repeated GXY sequences and are located on the cell surface of the human bacterial pathogen, Streptococcus pyogenes or a group A Streptococcus (GAS). The Scl1 and Scl2 proteins have a similar primary structure, which allows for the assignment of four common domains (42). The amino terminal signal sequence and carboxyl terminal cell-wall associated regions are conserved between Scl1 and Scl2, whereas the variable (V) and the collagen-like (CL) regions differ significantly in length and primary sequence. In addition, Scl1, but not Scl2, contains a linker (L) region between the collagen-like and the cell-wall regions, which is composed of highly conserved tandem repeats. This model was recently supported by an extensive genome-based sequence analysis that further established the presence of putative collagen-like domains in prokaryotic proteins (16).

Group A *Streptococcus* (GAS) are extracellular pathogens that can attach to and invade various human cell types using cellular receptors such as CD44, CD46, and integrins (46–50). Productive adherence is the first step required for pathogenic bacteria to colonize, invade, divide, and secrete virulence factors (51). Integrins are normally located on the basal side of polarized cells and, therefore, may not be immediately accessible for the interactions. It has been postulated that local trauma is required for streptococci to invade deeper anatomical sites. A few distinct routes, through which *S. pyogenes* emigrate into the underlying tissues, have been identified.

One model proposes that bacterial invasion is dependent on the presence of M1 protein on the cell surface. In this mechanism, streptococci efficiently invaded HeLa (epithelial) cells by a zipper-like mechanism mediated by host cell microvilli and the resulting endocytosis was accompanied by actin polymerization (52). In a paracellular model, the M3-serotype GAS strain producing hyaluronic acid (HA) capsule interacts with CD44 to promote the formation of lamellipodia in keratinocytes in a Rac-1-dependent manner. This event also disrupts intercellular cell-cell adhesion junctions, thereby allowing the pathogen to emigrate onto the baso-lateral surface of cultured keratinocytes (50).

More recently, a study demonstrated that human umbilical vein endothelial cells (HUVECs) directly uptake GAS strain expressing surface protein Sfb1 through "caveolae" (53). A primary component of these caveolae is a membrane bound protein caveolin-1, whose functions are dependent on sphingolipids and cholesterol (54–55). Pre-treatment of HUVECs with methyl-β-cyclodextrin and filipin, drugs that disrupt caveolae and membrane-microdomain by removing lipid moieties, abolished invasion of HUVECs by GAS (53). It was previously shown that integrins associate with caveolin-1 (56–58).

Three other streptococcal proteins have been reported to interact with various integrins. For example, a secreted cysteine protease (SpeB) variant that contains an RGD sequence motif and is expressed by the serotype M1 strains that cause invasive disease was shown to bind integrins $\alpha_v\beta_3$ and $\alpha_{11b}\beta_3$ (48,59). In addition, two FN-binding streptococcal cell surface proteins, SfbI/F1 and M1, were shown to bind to $\alpha_5\beta_1$ integrin via FN (52, 60–61).

Streptococcal cell wall structures that molecularly mimic components of the human body have long been postulated to be a factor in postinfectious autoimmune disease such as rheumatic fever and poststreptococcal glomerulonephritis. In addition, microbial infections are presumed to play a triggering role in several other autoimmune diseases. Interestingly, autoimmune diseases are often associated with elevated levels of anti-collagen antibodies present in patients' sera. Furthermore, autoimmune diseases can be induced in experimental animals treated with collagen. The discovery that Scl proteins have structural similarity to collagens and during infection could induce antibodies cross-reacting with host collagens adds another dimension to GAS-induced autoimmunity.

The inventors have recognized a need in the art for improvements in methods of producing a new source of collagen and in methods of employing prokaryotic GXY sequences in function- and structure-related studies. Specifically, the prior art is deficient in prokaryotic-like collagens and in determining their role in employing host cell-specific receptors, e.g., the collagen-binding integrins. The present invention fulfills this long-standing need and desire in the art.

SUMMARY OF THE INVENTION

The present invention is directed to a recombinant triple helical protein. This recombinant protein comprises a prokaryotic protein or one or more domains of a prokaryotic protein comprising a collagen-like peptide sequence of repeated Gly-Xaa-Yaa triplets having non-modified amino acids. This recombinant triple helical protein may further comprise one or more domains of a biologically active mammalian protein or peptide fragment therefrom.

The present invention is directed to a related recombinant collagen-like protein. The recombinant collagen-like protein comprises one or more domains having a peptide sequence of one or more of SEQ ID NOS: 1–42.

The present invention is directed also to a chimeric collagen-like protein. The collagen-like protein comprises one or more domains having a peptide sequence of one or more of SEQ ID NOS: 1–42 and one or more domains of a human collagen protein.

The present invention also is directed to an expression vector comprising a DNA encoding the recombinant triple helical protein. The present invention also is directed to a related expression vector comprising a DNA encoding the recombinant collagen-like protein.

The present invention also is directed to a host cell comprising an expression vector described herein.

The present invention is directed further to a method of producing a triple helical protein. The method comprises introducing into a prokaryotic host cell an expression vector comprising a DNA sequence encoding the triple helical protein described herein, culturing the host cell under conditions suitable to express the protein and isolating the expressed protein to produce a triple helical protein. Additionally, the method may comprise purifying the triple helical protein. Furthermore, the method may comprise heating the triple helical protein and producing a gelatin-like material therefrom. In a related method the expression vector comprises DNA encoding a triple helical protein having one or more domains having a peptide sequence of one or more of SEQ ID NOS: 1–42.

The present invention is directed further to another related method of producing a collagen-like protein having one or more domains having a peptide sequence of one or more of SEQ ID NOS: 1–42. The method comprises those steps described supra for a triple helical protein.

The present invention is directed further still to a method of producing a gelatin-like material. The method comprises introducing into a prokaryotic host cell an expression vector comprising a DNA sequence encoding a protein having one or more domains having a peptide sequence of one or more of SEQ ID NOS: 1–42, and culturing the prokaryotic host cell under conditions suitable to express the protein. The expressed protein is heated to produce the gelatin-like material.

The present invention is directed further yet to an antibody directed against a recombinant streptococcal collagen-like (rScl) protein. The rScl protein binds to $\alpha_2\beta_1$ integrin. Also, the present invention is directed to a related antibody directed against p176 which binds $\alpha_2\beta_1$ integrin. The present invention is directed further to another related antibody directed against a domain in p176 that binds an $\alpha_2$-I domain of $\alpha_2\beta_1$ integrin.

The present invention is directed further still to a method for screening for compounds that inhibit streptococcal collagen-like (Scl) protein binding to or interaction with an integrin. The method comprises measuring Scl binding to or interaction with the integrin in the presence of a test compound and measuring Scl binding to or interaction with the integrin in the absence of the test compound in a control sample. Binding of the integrin to Scl in the presence of the test compound is compared with binding in the control sample. A reduction in binding of the integrin to Scl in the presence of the test compound compared to control correlates with inhibition of integrin binding to or interaction with Scl by the test compound.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 1A shows a schematic representation of the Scl1.1 and Scl2.28 proteins and the recombinant polypeptides (not to scale). Ss, signal sequence; V, variable region; CL, collagen-like region; L, linker region; WM, cell wall/membrane region. All recombinant proteins, P144, P157, P158, and P163, contain Strep-tag II (NH$_2$-WSHPQFEK-COOH; SEQ ID NO: 45) at their carboxyl termini. FIG. 1B shows the 15% SDS-PAGE analysis of purified recombinant proteins. Duplicated samples of P144, P157, and P158 were transferred onto the nitrocellulose membrane. Immunoblots were probed with the affinity-purified antibody directed against the V region of the Scl 1.1 protein.

FIG. 1C shows a schematic representation of the recombinant P176 and P163 (not to scale) and FIG. 1D shows a Commassie stained 12% SDS-PAGE integrity analysis of purified rScls. V, variable region; CL, collagen-like region; L, linker region; tag, Strep-tag II (NH$_2$-WSHPQFEK-COOH).

FIGS. 2A–2B show oligomerization of the recombinant proteins. Heat-denatured (90° C.) or native (4° C.) P144, P157, and P163 recombinant proteins were electrophoretically separated in 10–20% gradient gels without (FIG. 2A) or with (FIG. 2B) SDS and visualized by staining. Migration of molecular mass standards is shown in SDS-PAGE. FIG. 2C demonstrates resistance to trypsin digestion. Samples of heat-denatured or native P144 were digested with trypsin at 15° C. Samples were separated in 12% SDS-PAGE, and band intensities of protein resistant to trypsin were estimated at different time points.

FIGS. 3A–3H depict circular dichroism spectra and thermal stability of recombinant rScl proteins. FIGS. 3A–3C are wavelength scans of P144, P157, and P163 before and after unfolding and refolding. Solid lines, CD spectra at 4° C. (P144 and P163) and 25° C. (P157) before unfolding; broken lines, CD spectra at 50° C. after unfolding; dotted lines, CD spectra at 4° C. (P144 and P163) and 25° C. (P157) after refolding. FIGS. 3D–3F show thermal unfolding and refolding profiles of P144, P157, and P163. CD was recorded at 220 nm with a temperature slope of 20° C./h. I, unfolding curve; II, refolding curve. A connecting line was used to show the refolding curve of P157. The concentrations of the samples were: P144, 8.1 $\mu$M; P157, 29.8 $\mu$M; and P163, 7.7 $\mu$M. FIG. 3G shows the circular dichroism spectrum of the variable region of Scl1. Wavelength scan of P158 (10 $\mu$M) at 25° C. FIG. 3H shows the circular dichroism spectra of P176 before unfolding (4° C. and 25° C.), after unfolding (50° C.) and refolding (4° C., renatured).

FIGS. 4A–4G show the organization of the Scl1 and Scl2 proteins as viewed by electron microscopy after rotary shadowing. FIG. 4A shows a field demonstrating lollipop-like structures, monomers and dimmers, adopted by P144 (Scl1.1). An example of a P144 monomer is indicated with an arrow and a dimer is identified with an arrowhead. FIG. 4B shows selected monomers with a two-domain structure shown at higher magnification. FIG. 4C shows selected dimers at higher magnification demonstrating head-to-head interactions. FIG. 4D shows a field demonstrating the formation of rod-shaped particles by P157 corresponding to the collagen-like region of Scl1.1. FIG. 4E shows identification of the globular domain of P144 using anti-V region antibody. An example of an antibody bound to the globular domain of P144 (Scl1.1) is indicated with an arrow and an unbound antibody is indicated with an arrowhead. FIG. 4F shows a lollipop-like structure of P163 (Scl2.28). FIGS. 4A and 4D–4F are shown at the same magnification. Bars: 50 nm. FIG. 4G is an electron micrograph of the rotary shadowed P176, demonstrating the formation of lollipop-like structures.

FIGS. 5A–5B are a triple-helical model of the collagenous domains of Scl1.41 (SEQ ID NO.: 15) and Scl2.28 (SEQ ID NO.: 43) and the amino acid sequence of P176. In FIG. 5A three polypeptide chains (blue, orange, and pink) were modeled based on the crystallographic determination of a collagen-like peptide Pro-Pro-Gly. The amino acid sequences (blue chains) are shown. Selected residues are depicted as follows: Pro, black; ionizable residues Lys and Arg, red; stabilizing triplets GPR, GER, GPA, GDR, GKD, and GEK are marked with green dots. In FIG. 5B the amino acid sequence of P176 (SEQ ID NO.: 44) is shown in black. Selected residues are depicted as follows: collagen-like region (CL), red; variable region (V), blue; collagen; Strep-tag II (stag), lower case.

FIGS. 6A–6D show the expression of integrins on the surface of MCR-5 cells (FIG. 6A) and WI-38 cells (FIG. 6B) and demonstrate adhesion of MRC-5 (FIG. 6C) and) WI-38 fibroblast cells (FIG. 6D) after permissive adhesion was allowed to occur for 45 or 90 min. Cells (~2×10$^6$) were incubated in suspension with control mouse IgG, mouse anti-human $\alpha_1\beta_1$(TS2/7), $\alpha_2\beta_1$ (P1E6), $\alpha_3\beta_1$(P1B5), $\alpha_\nu\beta_3$ (LM609), $\alpha_5\beta_1$ (P1D6), or $\beta_1$(4B4) integrin antibodies, as indicated. Cells then were washed and incubated with secondary goat anti-mouse conjugated to FITC (~5.0 mg/ml), fixed, and subjected to FACS analysis. 96 well microtiter plates were coated with increasing concentrations of BSA, FN, and Col I (1.25, 2.5, 5, 10 mg/ml), and Scl at 12.5, 25, 50, and 100 nM. Cell adhesion assays were performed as described in Example 1. Data are expressed as mean±SD from three replicates and are representative of four independent experiments.

FIGS. 8A–8H show the characterization of and adhesion of fibroblast cells on recombinant P181 and P182. Effects of domain swapping between P163 and P176 are demonstrated. Triple-helix formation and two-domain lollipop-like structural organization of the recombinant P181 (FIG. 8A) and P182 (FIG. 8D) were confirmed by CD spectra (FIGS. 8B and 8E) and EM analyses (FIGS. 8C and 8F), respectively. Adhesion activities of MRC-5 and WI-38 cells on wells coated with either the P176, P181, or P182 substrates was examined. 96-well microtiter plates were coated with increasing concentrations of either BSA, FN, Col I (1.25, 2.5, 5, 10 mg/ml), or Scl at 12.5, 25, 50, and 100 nM. Adhesion levels of (FIG. 8G) MRC-5 and (FIG. 8H) WI-38 cells are shown after 45 and 90 min permissive adhesion, as indicated. Data are expressed as mean±SD from three replicates and are representative of four independent experiments.

FIGS. 9A–9C demonstrate that cell adhesion onto immobilized P176 is mediated by $\alpha_2\beta_1$ integrin. In FIG. 9A approximately 1×10$^5$ MRC-5 cells were pre-incubated with 1, 5 or 10 μg/ml anti-human [IgG (c), $\alpha_1\beta_1$(TS2/7), $\alpha_2\beta_1$ (P1E6), $\alpha_3\beta_1$(P1B5), $\alpha_v\beta_3$(LM609), $\alpha_5\beta_1$(P1D6) and $\beta_1$(4B4)] integrin antibodies in PBS containing $Ca^{2+}/Mg^{2+}$ on ice for 30 min. After washing with PBS, cells were suspended in defined media and replated onto microplates pre-coated with 100 nM of P176. Untreated control cells (c) or cells treated with 1, 2 and 5 mM of EDTA were also analyzed. After 45 min, cell adhesion was determined. In FIG. 9B C2C12-$\alpha_2$+ cells were plated onto dishes coated with 0.5 μg/ml of Col I, Col IV, VN and FN. Cell adhesion assays were performed after 45 minutes. In FIG. 9C C2C12-$\alpha_2$+ cells (0.5×10$^6$) each were incubated with 10 mg/ml of adhesion blocking monoclonal human anti-integrin antibody for 30 min, as indicated. Cells were washed and resuspended in defined media and were then replated onto plates coated overnight with 100 nM of Scl P176. Cells not incubated with antibody were included as control (c) or with 5 mM EDTA and subjected to cell adhesion for 45 min in a $CO_2$ incubator. Data are expressed as mean±SD from four replicates and are representative of two to four independent assays. Values are adjusted against background readings obtained from plates incubated in absence of cells. P-values:*<0.0001; Y<0.001.

FIGS. 11A–11H demonstrate P176 induced phosphorylation of FAK, paxillin, CAS, and JNK in MRC-5 cells. Serum-starved MRC-5 cells were detached non-enzymatically, washed, and replated on dishes coated either with FN, Col IV, Col I, or P176. For the phospho-specific immunoblots, i.e. anti-phospho-FAK and anti-phospho-JNK, total cell lysates were analyzed (FIGS. 11A and 11G). To evaluate the tyrosine phosphorylation state of p130CAS and paxillin, total lysates were pre-adsorbed and subjected to immunoprecipitation with these antibodies. The resulting immune complexes were then subjected to anti-phosphotyrosine immunoblotting (FIGS. 11C and 11E). All samples were then subjected to immunoblotting with the corresponding non-phospho-specific antibodies, to confirm that equal amounts of protein were present in each sample (FIGS. 11B, 11D, 11F, and 11H). All blots shown are representative of those obtained in at least three separate experiments, with similar results.

DETAILED DESCRIPTION OF THE INVENTION

Figure 1A:
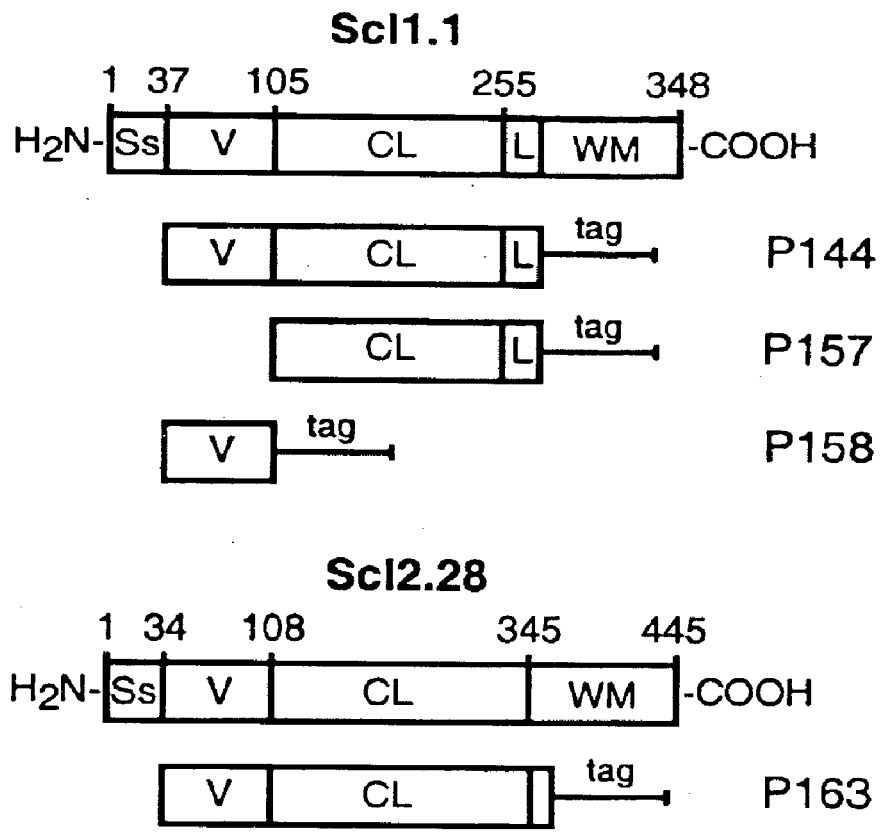
FIGS. 1A–1D are characterizations of the recombinant rScl proteins.

In one embodiment of the present invention there is provided a recombinant triple helical protein comprising a prokaryotic protein or one or more domains of a prokaryotic protein comprising a collagen-like peptide sequence of repeated Gly-Xaa-Yaa triplets having non-modified amino acids. Further to this embodiment the recombinant triple helical protein may comprise one or more biologically domains of a mammalian collagen or peptide therefrom. An example of a mammalian collagen is human collagen. In an aspect of this further embodiment, the prokaryotic collagen-like protein or one or more collagen-like domains thereof are fused to the one or more mammalian collagen domains.

In addition, in this embodiment the recombinant triple helical protein may comprise a peptide designed to add or improve a biological function of the recombinant triple-helical protein without disrupting the triple helical structure thereof. In one aspect the peptide comprises an amino acid sequence comprising at least one mutation in one or more of SEQ ID NOS: 1–42 or a peptide fragment thereof. In another aspect the peptide comprises a peptide fragment thereof or comprising an amino acid sequence generated via computer simulation.

In yet other aspects of this embodiment the collagen-like peptide sequence is from one or more streptococcal collagen-like proteins. The streptococcal collagen-like protein(s) may be from a Group A *Streptococcus*. A representative example of a Group A *Streptococcus* is *Streptococcus pyogenes*. Additionally, in this aspect the streptococcal collagen-like proteins may be a variant of *S. pyogenes* Scl1 or of *S. pyogenes* Scl2 or a combination thereof. Further to this aspect the peptide sequence comprises one or more of SEQ ID NOS: 1–42.

In a related embodiment there is provided a recombinant collagen-like protein comprising one or more domains having a peptide sequence of one or more of SEQ ID NOS: 1–42. Further to this related embodiment the recombinant triple-helical protein further may comprise one or more biologically active domains of a mammalian collagen. An example is human collagen. Additionally, in an aspect of this related embodiment, the one or more of SEQ ID NOS: 1–42 may fused to the one or more human collagen domains.

Again further to this embodiment the recombinant collagen-like protein may comprise a synthetic peptide as described supra.

In another related embodiment, there is provided a chimeric collagen-like protein comprising one or more domains having a peptide sequence of one or more of SEQ ID NOS: 1–42; and one or more biologically active domains of a mammalian collagen or peptide therefrom. The mammalian collagen may be human collagen. The collagen-like protein may be a fusion protein or a synthetic protein. Further to this embodiment the chimeric collagen-like protein may comprise a peptide as described supra.

In another embodiment of the present invention there is provided an expression vector comprising a DNA sequence encoding the recombinant triple helical protein described supra. In a related embodiment there is provided an expression vector comprising a DNA sequence encoding the collagen-like protein described supra.

In yet another embodiment of the present invention there is provided a host cell comprising and expressing an expression vector having a DNA sequence encoding the triple helical protein described supra. In a related embodiment there is provided an expression vector having a DNA sequence encoding the collagen-like protein described supra. In both these related embodiments the host cell may be a prokaryotic cell. Representative examples of useful prokaryotic cells are well known in the art and include *Escherichia coli*, *Streptococcus* and *Bacillus*.

In yet another embodiment of the present invention there is provided a method of producing a triple helical protein comprising introducing into a prokaryotic host cell an expression vector comprising a DNA sequence encoding the triple helical protein described supra; culturing the prokaryotic host cell under conditions suitable to express the protein; and isolating the expressed protein thereby producing the triple helical protein.

In an aspect of this embodiment the method may further comprise purifying the triple helical protein. In another aspect the method may further comprise heating the triple helical protein and producing a gelatin-like material therefrom. Representative examples of useful prokaryotic cells are well known in the art and include *Escherichia coli*, *Streptococcus* and *Bacillus*.

In a related embodiment there is provided a method of producing a triple helical protein comprising introducing into a prokaryotic cell an expression vector comprising a DNA sequence encoding a protein comprising one or more domains having a peptide sequence of one or more of SEQ ID NOS: 1–42; culturing the prokaryotic host cell under conditions suitable to express the protein; and isolating said expressed protein thereby producing the triple helical protein. In this embodiment the method may further comprise the purifying and heating steps as described supra. Representative examples of useful prokaryotic cells are well known in the art and include *Escherichia coli, Streptococcus* and *Bacillus*.

In another related embodiment there is provided a method of producing a collagen-like protein comprising introducing into a prokaryotic host cell an expression vector comprising a DNA sequence encoding the collagen-like protein comprising one or more domains having a peptide sequence of one or more of SEQ ID NOS: 1–42; culturing the prokaryotic host cell under conditions suitable to express the protein; and isolating the expressed protein thereby producing the collagen-like protein. In this embodiment the method may further comprise purifying and heating steps as described supra. Additionally, the collagen-like proteins and the prokaryotic host cell are as described supra.

In still another embodiment of the present invention there is provided a method of producing a gelatin-like material, comprising introducing into a prokaryotic host cell an expression vector comprising a DNA sequence encoding a protein comprising one or more domains having a peptide sequence of one or more of SEQ ID NOS: 1–42; culturing the prokaryotic host cell under conditions suitable to express the protein; and heating the expressed protein thereby producing the gelatin-like material. Representative examples of useful prokaryotic cells are well known in the art and include *Escherichia coli*, *Streptococcus* and *Bacillus*.

In still another embodiment of the present invention there is provided an antibody directed against a recombinant streptococcal collagen-like (rScl) protein. In an aspect of this embodiment the rScl protein may bind to $\alpha_2\beta_1$ integrin. More specifically, in this aspect the rScl protein binds to an $\alpha_2$-I domain of the $\alpha_2\beta_1$ integrin. An example of such an $\alpha_2$-I domain binding rScl is p176. Thus, in a related aspect of this embodiment there is provided an antibody directed against p 176. Furthermore, in another related aspect the antibody may be directed against a domain in p176 that binds an $\alpha_2$-I domain of $\alpha_2\beta_1$ integrin.

In still another embodiment of the present invention there is provided a method of screening for therapeutic compounds that inhibit a Streptococcal collagen-like protein (Scl) binding to or interacting with an integrin. This method generally comprises measuring Scl binding to or interaction with the integrin in the presence of a test compound; measuring Scl binding to or interaction with the integrin in the absence of the test compound in a control sample; comparing binding of the integrin to Scl in the presence of the test compound with binding in the control sample; and correlating a reduction in binding of the integrin to Scl in the presence of the test compound compared to control with inhibition of integrin binding to or interacting with Scl by the test compound, thereby screening for the therapeutic compound.

In an aspect of this embodiment the streptococcal collagen-like protein may be P176. In another aspect the Scl protein may bind to or interact with an $\alpha_2\beta_1$ integrin. Further to this aspect the Scl protein may bind to or interact with an $\alpha_2$-I domain of said $\alpha_2\beta_1$ integrin.

The following abbreviations are used herein: (r)Scl, (recombinant)streptococcal collagen-like; GAS, group A *Streptococcus*; FAK, focal adhesion kinase; CAS, crk associated substrate; JNK, c-Jun N-terminal kinase; FN, fibronectin; Col I, type I collagen; Col IV, type IV collagen.

Provided herein are prokaryotic triple helical proteins, prokaryotic collagen-like proteins and gelatin-like materials comprising these proteins. Generally, these proteins are recombinant proteins and may comprise a prokaryotic protein or one or more domains of a prokaryotic protein comprising a collagen-like peptide sequence of non-modified evolutionarily conserved Gly-Xaa-Yaa (GXY) sequence repeats that can form structurally conserved collagen-like triple helices, despite the lack of hydroxyprolines. As such, the GXY triplets may comprise a non-modified proline in the X or Y position.

More particularly, the present invention provides recombinant streptococcal collagen-like (Scl) proteins, derived from variants of Scl1 and Scl2, i.e., Scl1.41 and Scl2.28 comprising such non-modified conserved GXY triplet sequences. One of skill in the art will appreciate that several sequence characteristics of Scl1 and Scl2 can promote and stabilize the triple helix folding of the CL regions of the two proteins. For example, the number of continuous GXY repeats is high and often exceeds the number found in collagenous domains of mammalian proteins. Secondly, 30% and 37% of GXY repeats in Scl1.41 and Scl2.28, respectively, contain prolines, primarily at the X position.

In collagens, the cyclic ring of prolines stabilizes each collagen chain by steric repulsion. Without being bound by theory, the proline residues in Scls likely have the same effect. Also, Scl proteins have a high content of charged amino acids, i.e., 32% and 29.5% in Scl1.41 and Scl2.28, respectively, especially lysine and arginine with long ionizable side chains that can directly interact with residues of a neighboring polypeptide chain. Further, Scls contain triplets GPR, GER, GPA, GDR, GKD, and GEK, which stabilize a triple helix. None of the GXY triplets which destabilize the triple helix structure of model synthetic peptides are present in the CL region of the rScl proteins.

Scls also contain triplets that stabilize the triple helix by formation of alternative hydrogen bonding and hydration patterns. For example, the GEK triplet, which was proposed to stabilize the triple helix through formation of indirect water-mediated bridges, is the most frequent triplet in Scl 1.41CL. In addition, threonines in the Y position of GET and GKT, found in both Scl1 and Scl2, may substitute for hydroxyprolines in the formation of hydrogen bonds.

Additionally, the lollipop-like structure of the recombinant Scl proteins resembles the observed structural organization of mammalian cell surface proteins with collagenous domains. Scl proteins likely form lollipop-like structures on the surface of streptococcal cells as do the recombinant polypeptides of the present invention. Scl proteins likely interact with molecules in the environment of the streptococci.

The structural organization of the Scl proteins is particularly suited for a ligand binding where the stalk-forming CL region projects the globular V region away from the bacterial surface, facilitating possible interactions between the V regions and their potential targets. The CL regions may themselves interact with various molecules as found with mammalian collagens and proteins with collagenous domains. Furthermore, interactions between the CL and V regions may be required in the efficient assembly of the triple helix.

A list of sequences of collagen-like domains from Scl1 and Scl2 proteins are presented in Table 1. These sequences contain the repeating amino acid sequence Gly-Xaa-Yaa (GXY) in which glycine occupies every third position which is critical to allow the encoded proteins to form a homotrimer. The recombinant collagen-like proteins may comprise one or more domains having a peptide sequence from SEQ ID NOS: 1–42.

TABLE 1

| Strain No | M type | Amino Acid Sequence in the collagen-like region of Scl1 protein | |
|---|---|---|---|
| 6708 | M1 | GKSGIKGDRGETGPAGPAGPQGKTGERGAQGPKG | (SEQ ID NO: 1) |
| | | DRGEQGIQGKAGEKGERGEKGDKGETGERGEKGE | |
| | | AGIQGPQGEAGKDGAPGKDGAPGEKGEKGDRGE | |
| | | TGAQGPVGPQGEKGETGAQGPAGPQGEAGKPGE | |
| | | QGPAGPQGEAGQPGEK | |
| 3803 | M2 | GEKGEAGIQGPQGKAGKDGAPGKDGAVGAQGP | (SEQ ID NO: 2) |
| | | KGDKGDTGEKGETGATGAQGPQGEAGKDGAPG | |
| | | EKGEKGDRGETGAQGPVGPQGEKGETGAQGPA | |
| | | GPQGEKGETGAQGPAGPQGEAGKPGEQGPAGP | |
| | | QGEAGKPGEK | |
| 315 | M3 | GDKGETGLAGPVGPAGKAGARGAQGPAGPRG | (SEQ ID NO: 3) |
| 321 | M4 | GEKGDAGPRGERGPQGPVGPAGKAGEKGEAGI | (SEQ ID NO: 4) |
| | | QGPQGEAGKDGAPGKDGAPGEKGEKGDRGETG | |
| | | AQGPVGPQGEKGETGAQGPAGPQGEAGKPGEQ | |
| | | GPAGPQGEAGKPGEQGGKPGEK | |
| 6169 | M6 | GEKGDPGAQGPKGEKGEKGDRGDTGAQGPVGP | (SEQ ID NO: 5) |
| | | QGEAGQPGEK | |
| 6159 | M9 | GEKGDAGPVGPAGPRGERGPQGEKGAQGLKGE | (SEQ ID NO: 6) |
| | | KGDTGAVGAQGPKGDKGDTGERGEKGDTGATG | |
| | | AQGPQGEAGKDGAPGKDGAPGEKGEKGDRGET | |
| | | GAQGPVGQQGEAGKPGEQGEAGKPGEQ | |

TABLE 1-continued

| | | | |
|---|---|---|---|
| 6276 | M12 | GPAGPKGETGPAGPAGPEGKPGKAGEKGDRGE KGEAGIQGPQGEKGDTGAQGPQGEAGAPGEKG EKGDRGETGAQGPVGPQGEKGETGAQGPQGEA GKPGEQGPQGEAGKPGEK | (SEQ ID NO: 7) |
| 6259 | M12 | GPAGPKGETGPAGPAGPEGKPGKAGEKGDRGE KGEAGIQGPQGEKGDTGAQGPQGEAGAPGEKG EKGDRGETGAQGPVGPQGEKGETGAQGPQGEA GKPGEK | (SEQ ID NO: 8) |
| 6144 | M12 | GPAGPKGETGPAGPAGPEGKPGKAGEKGDRGE KGEAGIQGPQGEKGDTGAQGPQGEAGKPGEKA PEKSPEGEAGQPGEK | (SEQ ID NO: 9) |
| 156 | M18 | GKSGIKGDRGETGPAGPAGPQGKTGERGAQGP KGDRGEQGIQGKAGEKGERGEKGDKGETGERG EKGEAGIQGPQGEAGKDGAPGKDGAPGEKGEK GDRGETGAQGPVGPQGEKGETGAQGPAGPQGE AGKPGEQGPAGPQGEAGQPGEK | (SEQ ID NO: 10) |
| 6269 | M22 | GPAGPEGKPGPKGDKGETGARGPRGERGETGL QGPKGEAGKDGAQGEKGEKGDRGEKGEAGIQG PKGEAGKDGAPGEKGEKGDRGETGAQGPVGPQ GEKGETGAQGPAGPQGEAGKPGEQGPAGPQGE AGKPGEK | (SEQ ID NO: 11) |
| 6141 | M28 | GDKGDAGPKGERGPAGPQGPVGPKGEAGKVGA QGPKGDPGAPGKDGAKGEKGDKGDTGERGEKG DIGATGAQGPAGPQGEAGKPGEQGPAGPQGEA GKPGEKAPEKSPEGEAGQPGEK | (SEQ ID NO: 12) |
| 6143 | M28 | GDKGDAGPKGERGPAGPQGPVGPKGEAGKVGA QGPKGDPGAPGKDGAKGEKGDKGDTGERGEKG DIGATGAQGPQGEAGKDGAPGEKGDKGDRGET GAQGPVGPQGEKGETGAQGPAGPQGEAGKPGE QGPAGPQGEAGKPGEK | (SEQ ID NO: 13) |
| 6274 | M28 | GDKGDAGPKGERGPAGPQGPVGPKGEAGKVGA QGPKGDPGAPGKDGAKGEKGDKGDTGERGEKG DIGATGAQGPQGEKGETGAQGPAGPQGEAGKP GEQGPAGPQGEAGKPGEK | (SEQ ID NO: 14) |
| 6183 | M41 | GEKGEAGPQGEKGLPGLTGLPGLPGERGPRGP KGDRGETGAQGPVGPQGEKGEAGTPGKDGLRG PQGDPGAPGKDGAPGEKGDRGETGAQGPVGPQ GEKGEAGTPGKDGAPGEKGEKGDRGETGATGA QGPQGEAGKDGAQGPVGPQGEKGETGAQGPAG PQGEKGETGAQGPAGPQGEAGQPGEK | (SEQ ID NO: 15) |

TABLE 1-continued

| 4569 | M49 | GPKGDPGPVGPRGPEGKPGKDGAKGDTGPRGE RGEQGIQGEQGKAGEKGEKGDKGDTGERGEKG DTGATGAQGPQGEAGKDGAPGEKGEKGDTGAQ GPVGPQGEKGETGAQGPQGEAGKPGEQGPAGP QGEAGKPGEK | (SEQ IF NO: 16) |
| --- | --- | --- | --- |
| 6186 | M52 | GPKGDPGPAGPRGPVGPEGPAGKPGKDGAQGE RGKQGDPGPKGDKGEDGKVGPRGPKGDRGETG AQGPVGPQGETGKDGAPGEKGEKGDRGETGAQ GPVGPQGETGKDGAPGEKGEKGDRGETGAQGP VGPQGETGKDGAPGEKGEKGDRGETGAQGPVG PQGEKGETGAQGPAGEK | (SEQ ID NO: 17) |
| 6177 | M52 | GPKGDPGPAGPRGPVGPVGPVGPAGKPGKDGA QGERGKQGDPGPKGDKGEDGKVGPRGPKGDRG ETGAQGPVGPQGETGKDGAPGEKGEKGDRGET GAQGPVGPQGETGKDGAPGEKGEKGDRGETGA QGPVGPQGETGKDGAPGEKGEKGDRGETGAQG PVGPQGEKGETGAQGPAGEK | (SEQ ID NO: 18) |
| 1863 | M55 | GEKGDPGAPGKDGAVGAQGPKGEKGEKGDRGD TGAQGPVGPQGEKGEKGEKGETGEQGPAG PQGEAGKPGEK | (SEQ ID NO: 19) |
| 4487 | M56 | GIKGDRGETGPAGPAGPVGPVGPRGPEGPEGKQGK PGKRGAQGIQGPKGDKGETGERGEQGLQGEKGDT GAAGAPGKDGVQGPKGDKGETGERGEKGEAGIQG PQGEKGDTGATGAQGPQGEAGKDGAPGEKGEKGD RGETGAQGPVGPQGEKGETGAQGPAGEK | (SEQ ID NO: 20) |
| 6146 | M56 | GIKGDRGETGPAGPAGPVGPVGPRGPEGPEGK QGKPGKRGAQGIQGPKGDKGETGERGEQGLQG EKGDTGAAGAPGKDGVQGPKGDKGETGAQGPV GPQGEKGETGAQGPAGEK | (SEQ ID NO: 21) |
| 1864 | M57 | GDKGDAGPKGERGPAGPQGPVGPKGEAGKPGA QGPKGDKGETGERGETGAQGPVGPQGEKGETG EQGPAGPQGEAGKPGEQGPAGQPGEK | (SEQ ID NO: 22) |
| 4673 | M75 | GDKGDTGPAGPQGKTGERGAQGPKGDRGEQGI QGKAGEKGERGEKGDKGETGERGEKGEAGIQG PQGEKGDTGAQGPQGEAGKDGAPGEKGEKGDR GDTGAQGPVGPQGEKGETGAQGPAGPQGEAGQ PGEK | (SEQ ID NO: 23) |

TABLE 1-continued

| Strain No | M type | Amino Acid Sequence in the collagen-like region of Scl2 protein | |
|---|---|---|---|
| 6133 | M76 | GKSGIKGDRGETGPAGPAGPRGPVGPAGEAGK QGDRGEQGIQGPKGEAGAPGKDGAKGEKGDKG DTGERGEKGDTGAQGPQGEAGKDGAPGKDGAP GEKGEKGDRGETGAQGPVGPQGEKGETGAQGP AGPQGEAGKPGEQGPAGPQGEAGKPGEK | (SEQ ID NO: 24) |
| 6191 | M77 | GPAGPAGPRGPKGEDGKAGAPGKDGAPGKDGA PGKDGAPGKDGAQGPKGDKGETGERGEKGETG ATGAQGPQGEAGKDGAPGEKGEKGDRGETGAQ GPVGPQGEKGETGAQGPAGPQGEAGQPGEQGP AGPQGEAGQPGEK | (SEQ ID NO: 25) |
| 6250 | M77 | GPAGPAGPRGPKGEDGKAGAPGKDGAPGKDGA PGKDGAQGPKGDKGETGERGEKGETGATGAQG PQGEAGKDGAPGKDGAPGKDGAQGPKGDKGET GERGEKGETGATGAQGPQGEAGKDGAPGEKGE KGETGAQGPAGPQGEAGQPGEQGPAGPQGEAG QPGEK | (SEQ ID NO: 26) |
| 1880 | ST2035 | GEKGEAGIQGPQGKAGKDGAPGKDGAPGKDGA VGAQGPKGDKGDTGEKGETGATGAQGPQGEAG KDGAPGEKGEKGDRGETGAQGPVGPQGEKGET GAQGPAGPQGEAGKPGEQGPAGPQGEAGKPGE K | (SEQ ID NO: 27) |
| 6155 | ST2967 | GKSGIKGDRGEAGPAGPAGPRGERGPAGEAGK QGERGEQGIQGPKGETGAVGAQGPKGDKGDTG ERGEKGDTGATGAQGPQGEAGKDGAPGEKGEK GDRGETGLQGPVGPQGEKGEIGAQGPAGPQGE AGIPGEK | (SEQ ID NO: 28) |

| Strain No | M type | Amino Acid Sequence in the collagen-like region of Scl2 protein | |
|---|---|---|---|
| 6708 | M1 | GPKGPAGEKGEQGPTGKQGERGETGPAGPRGD KGETGDKGAQGPVGPAGKDGQDGKDGLPGKDG KDGQDGKDGLPGKDGK | (SEQ ID NO: 29) |
| 3803 | M2 | GDQGERGEAGPQGPAGQDGKAGDRGETGPAGP VGPAGPQGPRGDKGETGERGEQGPAGQDGKAG DRGETGPAGPVGPAGPQGPRGDKGETGERGEQ GPAGQDGKDGDRGETGPAGPVGPAGKDGQDGK DGLPGKDGKDGQDGKDGLPGKDGKDGQPGKP | (SEQ ID NO: 30) |
| 315 | M3 | GQDGDRGEAGPAGPRGEAGPAGPRGEAGKDGAKG DRGEAGPAGPRGEAGKDGAKGDRGEAGPAGPRG EAGKDGAKGDRGEAGPAGPRGEAGKDGAKGDRG EAGPAGPRGEAGPAGPRGEAGPAGPRGEAGPAGPR | (SEQ ID NO: 31) |

TABLE 1-continued

| | | |
|---|---|---|
| | | GEAGKDGAKGDRGEAGPAGPRGEAGKDGAKGDR |
| | | GEAGPAGPRGEAGKDGAKGDRGEAGPAGPRGEAG |
| | | PAGPRGEAGKDGAKGDRGEAGPAGPRGEAGKDGA |
| | | KGDRGEAGPAGPRGEAGKDGAKGDRGEAGPAGPR |
| | | GEAGKDGAKGDRGEAGPAGPRGEAGKDGAKGDR |
| | | GEAGPAGPRGEAGKDGAKGDRGEAGPAGPRGEAG |
| | | PAGKDGQPGKP |
| 321 | M4 | GDKGEPGAQGPAGPRGETGPAGERGEKGEPGT (SEQ ID NO: 32) |
| | | QGAKGDRGETGPAGPRGDKGEKGEQGPAGKDG |
| | | ERGPIGPAGKDGQDGKDGLPGKDGKDGQDGKD |
| | | GLPGKDGKDGQDGKDGLPGKP |
| 6159 | M9 | GDQGDPGERGETGPAGPAGPVGPVGPRGERGE (SEQ ID NO: 33) |
| | | AGPAGQDGKAGDRGETGPAGPVGPRGDKGEKG |
| | | EQGPAGKDGLPGKDGKDGQDGKDGLPGKDGKD |
| | | GQDGKDGLPGKDGKDGQDGKDGLPGKDGKDGQ |
| | | DGKDGLPGKDGKDGQDGKDGLPGKDGKDGQDG |
| | | KDGLPGKDGQPGKP |
| 6139 | M12 | GEKGERGPVGPAGPQGLQGTKGDRGETGEQGQ (SEQ ID NO: 34) |
| | | RGETGPAGPQGPAGPVGPAGKDGEAGAQGPVG |
| | | PAGKDGQDGKDGLPGKDGQDGKDGLPGKDGKD |
| | | GQDGKDGLPGKDGKDGLPGKDGKDGQDGKDGQ |
| | | DGKDGLPGKDGQDGKDGLPGKDGQDGKDGKDG |
| | | LPGKDGKDGLPGKDGKDGQPGKP |
| 6276 | M12 | GEKGERGPVGPAGPQGLQGTKGDRGETGEQGQRGE (SEQ ID NO: 35) |
| | | TGPAGPQGPAGPVGPAGKDGQDGKDGLPGKDGQD |
| | | GKDGLPGKDGQDGKDGLPGKDGKDGQDGKDGLP |
| | | GKDGKDGLPGKDGPDGKDGLPGKDGKDGQDGKD |
| | | GLPGKDGKDGLPGKDGKDGQDGKDGQDGKDGLP |
| | | GKDGQDGKDGLPGKDGKDGQDGKDGLPGKDGK |
| | | DGLPGKDGKDGQPGKP |
| 6143 | M28 | GQDGRDGERGEQGPTGPTGPAGPRGLQGLQGE (SEQ ID NO: 36) |
| | | RGEQGPTGPAGPRGLQGERGEQGPTGLAGKAG |
| | | EAGAKGETGPAGPQGPRGEQGPQGLPGKDGEA |
| | | GAQGPAGPMGPAGERGEKGEPGTQGAKGDRGE |
| | | TGPVGPRGERGEAGPAGKDGERGPVGPAGKDG |
| | | QDGQDGLPGKDGKDGQDGKDGLPGKDGKDGQ |
| | | DGKDGLPGKDGKDGQDGKDGLPGKDGKDGLPG |
| | | KDGKDGQPGKP |

TABLE 1-continued

| | | | |
|---|---|---|---|
| 6274 | M28 | GQDGRDGERGEQGPTGPTGPAGPRGLQGLQGL | (SEQ ID NO: 37) |
| | | QGERGEQGPTGPAGPRGLQGERGEQGPTGLAG | |
| | | KAGEAGAKGETGPAGPQGPRGEQGPQGLPGKD | |
| | | GEAGAQGPAGPMGPAGERGEKGEPGTQGAKGD | |
| | | RGETGPVGPRGERGEAGPAGKDGERGPVGPAG | |
| | | KDGQDGQDGLPGKDGKDGQDGKDGLPGKDGKD | |
| | | GQDGKDGLPGKDGKDGQDGKDGLPGKDGKDGL | |
| | | PGKDGKDGQPGKP | |
| 6146 | M56 | GKDGETGPAGPTGPAGAKGETGPAGPVGPRGD | (SEQ ID NO: 38) |
| | | KGEKGEQGPAGKDGLPGKDGKDGQDGKDGLPG | |
| | | KDGKDGQDGKDGLPGKDGKDGQDGKDGLPGKD | |
| | | GKDGKDGDGQPGKP | |
| 4487 | M56 | GKDGETGPAGPTGPAGAKGETGPAGPVGPRGD | (SEQ ID NO: 39) |
| | | KGEKGEQGPAGKDGLPGKDGKDGQDGKDGLPG | |
| | | KDGKDGQDGKDGLPGKDGKDGQDGKDGLPGKD | |
| | | GKDGKDGDGQPGKP | |
| 4673 | M75 | GDQGEPGEPGEPGERGPRGEVGPAGPQGPVGPVGPA | (SEQ ID NO: 40) |
| | | GKDGTQGPRGDKGEPGEQGQRGETGPAGPQGPAG | |
| | | PVGPAGKDGTQGPRGDKGETGEQGQRGEVGPAGP | |
| | | QGPVGPVGPAGKDGAKGDRGETGPAGPAGKDGEA | |
| | | GAQGPGPAGPQGPRGDKGETGDKGEQGPAGKDGE | |
| | | RGPVGPAGKDGQDGLPGKDGKDGQDGKDGLPGK | |
| | | DGKDGQDGKDGLPGKP | |
| 6191 | M77 | GPRGDKGETGEQGPRGAQGPAGPQGPVGPAGK | (SEQ ID NO: 41) |
| | | DGTQGPRGDKGETGEQGPRGAQGPAGPQGPVG | |
| | | PAGKDGTQGPRGDKGETGEQGPRGAQGPAGPQ | |
| | | GPMGPAGERGEKGEPGTQGAKGDRGETGPAGP | |
| | | VGPRGDKGETGAKGEQGPAGKDGKAGERGPVG | |
| | | PAGKDGQDGKDGLPGKDGKDGQDGKDGLPGKD | |
| | | GKDGQDGKDGLPGKDGKDGQDGKDGLPGKDGK | |
| | | DGKDGKDGQPGKP | |
| 6155 | St2967 | GAKGEAGPAGPKGPAGEKGERGETGPAGPAGK | (SEQ ID NO: 42) |
| | | DGEAGAQGPMGPAGPQGPRGDKGETGDKGDQG | |
| | | PAGKDGDRGPVGPQGPQGETGPAGPAGKDGEK | |
| | | GEPGPRGEAGAQGPAGPQGPRGDKGETGDKGE | |
| | | QGPAGKDGERGPVGPAGKDGQDGKDGLPGKDG | |
| | | KDGQDGKDGLPGKDGKDGQDGKDGLPGKDGKS | |
| | | GQPGKP | |

The present invention also provides chimeric triple helical proteins or chimeric collagen-like protein. The recombinant triple helical proteins or recombinant collagen-like proteins described herein may additionally comprise at least one biologically active domain from a mammalian collagen, such as, but not limited to human collagens. For example, the protein may comprise one or more of SEQ ID NOS.: 1–42 and one or more domains from a mammalian, e.g., human, collagen protein.

The chimeric protein may be a fusion protein. Methods of constructing vectors suitable to transfect and express DNA encoding a fusion protein are standard in the art and well known to those of ordinary skill in the art. Alternatively, the protein may be a synthetic protein.

It is further contemplated that a peptide may be added to the triple helical recombinant proteins, the recombinant collagen-like proteins or the chimeric collagen-like proteins described herein. Addition of these peptides may alter structure and thereby function of the chimeric protein in a specifically selected manner. For example a new function may be added or an existing function improved. However the triple helical structure inherent in all the proteins described herein is not disrupted by the presence of the this peptide. The peptides may comprise at least one amino acid mutation in at least one of SEQ ID NOS.: 1–42 or in a peptide fragment thereof. Alternatively, the sequence of the peptide may be determined via computer simulation.

As such, the present invention further provides methods of producing a triple helical protein or a collagen-like protein. The methods may utilize expression vectors comprising a DNA that encodes the triple helical or collagen-like proteins of the present invention. Additionally, the present invention provides a host cell, such as a prokaryotic cell, for example, although not limited to, *Escherichia coli*, a *Streptococcus* or a *Bacillus*. It is standard in the art to construct such expression vectors and to transform a host cell to express the product of the DNA contained therein.

Generally, an expression vector as described herein is introduced into the prokaryotic host cell. The prokaryotic cell is cultured under conditions suitable to induce expression of the protein. The expressed protein is isolated and may further be purified. Also provided is a method of producing a gelatin-like material from the recombinant proteins presented herein. The triple helical and/or the collagen-like proteins may be heated to produce the gelatin-like material.

Furthermore, the present invention contemplates that designer collagens or gelatin-like substances may be produced for the specific needs of the user using the recombinant triple helical proteins, collagen-like proteins or chimeric proteins described herein. For example a collagen or gelatin may be designed to effectively function in any biological system. The problems associated with mammalian collagens, such as bovine collagens, can be avoided. This effectively would change and improve the commercial use of collagens.

The present invention further demonstrates that a member of the prokaryotic collagen-like proteins, the Scl1.41 variant of *S. pyogenes*, interacts with the I-domain of $\alpha_2\beta_1$ integrin, but not $\alpha_1\beta_1$ integrin. This interaction induces cell adhesion and signaling activities through FAK and CAS in human lung fibroblast MRC-5 cells. Thus, the Scl1.41 recombinant protein P176 (SEQ ID NO.: 44) can interact with an integrin in a productive manner, preferably via a binding site in the CL domain shown in SEQ ID NO.: 15.

Furthermore it is contemplated that cell adhesion to P176 is predominantly mediated by integrins. First, removal of $Ca^{2+}$ and $Mg^{2+}$ metal ions, which are required for collagen-integrin binding, inhibited cell adhesion activity. Second, the addition of an anti-$\beta_1$ integrin antibody completely inhibited adhesion of these cells onto P176. Third, cell adhesion to P176 was specifically mediated by the $\alpha_2\beta_1$ integrin, a known type I collagen receptor, because an anti-$\alpha_2\beta_1$ integrin monoclonal antibody blocked cell adhesion, whereas an anti-$\alpha_1\beta_1$ antibody did not. Fourth, the specificity of the $\alpha_2\beta_1$-P176 interaction was further supported by the fact that C2C12-$\alpha_2$+ cells adhered to P176 and an anti-$\alpha_2\beta_1$ integrin antibody or EDTA inhibited this adhesion. Finally, SPR analysis showed that P176 interacts with the I-domain of $\alpha_2$ integrin, which is an important characteristic of a collagen-integrin binding (34).

However, integrin ligation is not a general property of Scl proteins and several other recombinant proteins based on different Scl sequences did not support cell adhesion, such as the Scl2.28 recombinant protein P163, for example. This suggests that specific sequences present in some but not other Scl proteins are recognized by the integrins. It has been demonstrated that the $\alpha_1\beta_1$, and $\alpha_2\beta_1$ integrins interact with specific sequences in mammalian collagens. The substrate specificity of the two integrins appears to be similar, but not identical. Thus, $\alpha_1\beta_1$ but not $\alpha_2\beta_1$, integrin requires a hydroxyproline residue in the binding site for full activity. Consistent with this observation $\alpha_2\beta_1$, but not $\alpha_1\beta_1$, mediates cell adhesion to the P176 protein that does not contain hydroxy-proline residues.

Given that integrins are involved in streptococci host cell invasion and that fibronectin binding a MSCRAMM peptide (SEQ ID NO.: 46) on gram-positive bacteria can recruit soluble fibronectin which is then recognized by $\alpha_5\beta_1$ integrin thereby initiating cellular invasion, it could be contemplated that integrin interaction through a Scl protein would play a role in the infections process of *S. pyogenes*. Additionally, the $\alpha_2\beta_1$ integrin is also a prominent collagen receptor on platelets and it is possible that Scl proteins may induce a platelet signaling through interacting with the platelet integrin. The Scl protein-integrin interaction described herein suggest that these bacterial proteins are mimicking and being recognized as collagens when it comes to $\alpha_2\beta_1$ integrin. It is further contemplated that Scl proteins could also behave as collagens in other systems and that this molecular mimicry allows the bacteria to manipulate host biology at a number of different levels.

Thus the present invention provides antibodies directed against integrin-binding or integrin-interacting rScl proteins described herein. Preferably, cell adhesion is mediated by $\alpha_2\beta_1$ integrin. Most preferably, the rScl proteins bind to the I-domains of the integrins, such as to the $\alpha_2$-I domain of $\alpha_2\beta_1$ integrin. The antibody may be directed against P176 or to the domain in P176 that binds $\alpha_2\beta_1$ integrin or, more specifically, binds the $\alpha_2$-I domain of $\alpha_2\beta_1$ integrin. It is contemplated that antibodies may be directed against rScls comprising a P176 $\alpha_2$-I domain binding site or a P176-like CL domain or P176-like $\alpha_2$-I domain binding site.

The present invention further provides means to screen for therapeutic compounds or drugs, including proteins or peptides, that inhibit P176 from binding or interacting with integrin I-domains. Generally, a potential therapeutic compound may be screened by comparing the binding of $\alpha_2$-I to P176 in the presence and absence, as control, of the potential therapeutic compound. Inhibition of $\alpha_2$-I binding in the presence of the test compound would screen for potential therapeutic efficacy.

The following examples are given for the purpose of illustrating various embodiments of the invention and are not meant to limit the present invention in any fashion.

EXAMPLE 1

Materials and Methods

Recombinant Proteins

Recombinant proteins were obtained using the Strep-tag II expression and purification system (IBA-GmbH). Fragments encoding sequences of the scl1.1 allele were amplified from the serotype M1 strain MGAS6708 identical to SF370 used for genome sequencing. The scl2.28 sequence was amplified from the serotype M28 strain MGAS6274. DNA fragments were ligated to the *Escherichia coli* vector pASK-IBA2, and clones were confirmed by sequencing. Recombinant proteins were expressed in *E. coli* and purified by affinity chromatography on a Strep-Tactin-Sepharose. Thus, pSL163 was constructed which encodes a P163 polypeptide. The identity of each purified protein was confirmed by amino-terminal sequencing, and mass determinations were done by electrospray ionization mass spectrometry measurements.

Western immunoblot analysis was performed with proteins separated on SDS-PAGE, transferred onto a nitrocellulose membrane (Amersham Biosciences) and probed with specific, affinity-purified polyclonal rabbit antibodies raised against a synthetic peptide derived from the V region of Scl1.1. Horseradish peroxidase-conjugated goat anti-rabbit affinity-purified immunoglobulin G, heavy and light chains, (Bio-Rad) was used as the secondary antibody, and Super-Signal chemiluminescent substrate (Pierce) was used in signal detection. Prestained broad-range marker proteins (Bio-Rad) were used as molecular mass standards.

To obtain recombinant P176, the DNA sequence of the scl1.M41 allele (accession number AY452037) was amplified and cloned into an *E. coli* vector pASK-IBA2, resulting in plasmid pSL176. In a domain swapping experiment, plasmid pSL163 was used as a core sequence. First, a DNA fragment encoding the variable V region of P176 was amplified and substituted for the corresponding region of pSL163, resulting in the pSL181/P181 construct. Next, the pSL182 plasmid was obtained by replacing the DNA sequence of the collagen-like region in pSL181, originally from pSL163, with a corresponding DNA sequence of pSL176, which lacked a linker region. These plasmid constructs were verified by DNA sequencing. As above, recombinant proteins were purified by affinity chromatography on Strep-Tactin-Sepharose and their identity was confirmed by amino-terminal sequencing.

Gel Migration Analyses

The ability of the Scl proteins to form oligomers was examined by gel electrophoresis. Protein samples were heat-denatured at 90° C. for 5 min and then placed on ice for 2 min before loading, whereas native protein samples were not heated and were kept at 4° C. Denatured or native P144 and P163 proteins were electrophoretically separated in 10–20% gradient polyacrylamide gels with or without 0.1% SDS and visualized by staining.

The resistance of triple helix collagen to trypsin digestion was used as an indicator of macromolecular structure. Native and heat-denatured samples of recombinant P144 dissolved in 25 mM HEPES, pH 8.0, were digested with 10 μg/ml trypsin using an enzyme:protein molar ratio of 1:10 at 15° C. Aliquots were removed after 15, 30, and 60 min, and the reaction was stopped with phenylmethylsulfonyl fluoride. Samples were analyzed by SDS-PAGE using undigested P144 and P157 as size markers. Resistance of the triple-helical domain to trypsin was measured from band intensities and compared with an undigested sample.

Circular Dichroism (CD) Spectroscopy

The triple helical conformation of recombinant rScls was analyzed by circular dichroism, as described (62). Spectra were recorded on a Jasco J720 spectropolarimeter equipped with a variable temperature unit. Samples were dissolved in 1% phosphate-buffered saline, pH 7.4. Thermal transition profiles were recorded at 220 nm, as described above, with a temperature slope of 20° C./h or of 10° C./h. Measurements were taken with a 0.5-cm path length and data were integrated for 1 sec at 0.2-nm intervals with a bandwidth of 1 nm. A wavelength scan was performed for each protein before unfolding (4° C., 25° C.) and after unfolding (50° C.), or after subsequent refolding (4° C., renatured). The melting temperatures ($t_m$) were given as mean±S.D. of $t_m$ values from several measurements. Secondary structure compositions were estimated using three deconvolution programs, CD Estima, CONTIN, and SELCON, and the results were averaged.

Electron Microscopy

The structural organization of the recombinant proteins was viewed by electron microscopy of the rotary shadowed rScls, as previously (63). Protein samples (100 μg/ml) were dialyzed against 0.1 M ammonium bicarbonate and then mixed with glycerol to a final glycerol concentration of 70% v:v. Samples were sprayed onto freshly cleaved mica sheets and rotary shadowed with carbon/platinum at an angle of 6 degrees. The replicas were backed with carbon at 90 degrees and placed on copper grids. Photomicrographs were taken with a Philips 410 electron microscope operated at 80 KV with a 30-μm objective aperture.

The microscope was calibrated using a carbon grating replica. The height of the goniometer stage was adjusted for each grid square before taking pictures and the lenses were saturated before taking each photo. Molecule contours were traced on a digitizing tablet at a final magnification of ×181,500 and measurements were generated with Bioquant software.

Reagents and Antibodies

Cell culture media, human fibronectin, type I and type IV collagen, control mouse IgG, and anti-$\alpha_1\beta_1$ (TS2/7), anti-$\alpha_2\beta_1$ (P1E6), anti-$\alpha_3\beta_1$ (P1B5), anti-$\alpha_5\beta_5\beta_1$ (P1D6) integrin antibodies were purchased from Gibco-BRL/Invitrogen (Carlsbad, Calif.). Anti-FAK (2A7), anti-paxillin and anti-phospho-tyrosine (4G10) mouse monoclonal antibodies (mAbs) were purchased from Upstate Biotechnology Inc. (Lake Placid, N.Y.). Anti-phospho-JNK and anti-phospho-FAK (Y397) antibodies were purchased from Cell Signaling Technology (Beverly, Mass.). The anti-$\alpha_v\beta_3$ (LM609) was obtained from Chemicon (Temecula, Calif.). Anti-$\beta_1$ (4B4) integrin antibody was procured from BD Biosciences (San Jose, Calif.).

Cells and Cell Culture

Human lung fibroblast cell lines MRC-5 and WI-38 were obtained from ATCC(CCl-171; CCL-75) and cultured in DMEM supplemented with 10% FBS, 2.4 mM L-glutamine and antibiotics. Parental mouse myoblast C2C12 (control cells) and C2C12 cells stably transfected with the human $\alpha_2$-integrin subunit (C2C12-$\alpha_2$+), provided by D. Gullberg (Uppsala, Sweden), were maintained in 10% FBS in DMEM in the absence or presence of 10 mg/ml puromycin, respectively. Methods for growth and maintenance of adherent cells have been described (56,64).

Fluorescent Activated Cell Sorting (FACS)

Cells were washed in PBS, pH 7.4, then non-enzymatically dissociated with 2 mM EDTA in PBS and washed twice in PBS containing $Ca^{2+}$ and $Mg^{2+}$. Cells were passed through a cell strainer and enumerated. $2 \times 10^6$ cells were then incubated with saturating amounts of control mouse IgG or anti-human integrin monoclonal antibodies, e.g., anti-$\alpha_1\beta_1$ (TS2/7), anti-$\alpha_2\beta_1$ (P1E6), anti-$\alpha_3\beta_1$ (P1B5), anti-$\alpha_v\beta_3$ (LM609), anti-$\alpha_5\beta_1$ (P1D6) and anti-$\beta_1$ (4B4) for 30 minutes at 4° C. Secondary labeling was performed for 1 hour at 4° C. with a goat-anti mouse IgG conjugated to fluorescein isothiocyanate (FITC) (Molecular Probes, OR). Cells were washed twice with PBS, fixed with 0.5% p-formaldehyde (PFA) and analyzed with the FACS Calibur flow cytometer (Becton Dickinson, San Jose, Calif.).

Cell Adhesion and Spreading Assays

Cell adhesion to 24-well plates coated with specified substrates has been described (64). Briefly, the test substrates, i.e., Scl recombinant proteins, were prepared at a concentration of 12.5, 25, 50 and 100 nM in TBS (20 mM Tris, pH.7.4, 150 mM NaCl, 0.02% sodium azide) and coated onto sterile microplates overnight at 4° C. Human fibronectin, type IV collagen, type I collagen and BSA (1.25, 2.5, 5 and 10 μg/ml) were included as controls. BSA was subjected to 0.22 μm filtration and heat inactivation. After washing with PBS, plates were saturated with 0.5% BSA for 60 min in a 37° C. $CO_2$ incubator.

Human lung fibroblast MRC-5 and WI-38 or C2C12 cells starved overnight in serum-free media were detached in PBS containing 2 mM EDTA and 0.0025% trypsin. Cells were collected and resuspended in M199 defined media containing appropriate antibiotics, 0.2% BSA and 1×ITS (insulin, transferrin and selenium-A), supplemented with 2 mM $Mg^{2+}$ and 1 mM each of $Ca^{2+}/Mn^{2+}$. Saturated plates were washed once with PBS and 100 μl of cell suspension (0.15×10$^6$ cells/ml) were added and allowed to adhere.

After 45 or 90 min, unattached cells were gently removed and washed with PBS before fixing in 3% PFA for 10 min. The cells were then washed with cold TBS, refixed in 20% methanol for 10 min, and stained in 0.5% crystal violet for 5 min. Plates were thoroughly washed with water and air-dried. The dye was then eluted in 100 μl of 100 mM sodium citrate and absorbance was measured at 590 nm.

To visualize cell spreading, PFA-fixed cells were stained with standard eosin and hematoxylin and pictures were captured in an inverted light microscope under 20×magnification. Alternatively, cells grown on coverslips under similar conditions were stained with phalloidin-TRITC (Sigma, P-1951) and 4,6-diamidino-2-phenylindole dihydrochloride (DAPI; Molecular Probes, D-1306) to identify stress fibers and nuclei, respectively. A Zeiss Axiovert-125 fluoroscope was used for this purpose.

Cell Adhesion Blocking Assay

The cell adhesion blocking assay has been described (64). In brief, 70% confluent human lung fibroblast (MRC-5), parental C2C12 and C2C12-$_2$+ cells were washed in PBS, detached non-enzymatically in 2 mM EDTA, and washed. Cells were passed through a cell strainer and enumerated. Approximately 0.1×10$^6$ cells were incubated with 1, 5 and 10 mg/ml of anti-$a_1b_1$, anti-$a_2b_1$, anti-$a_3b_1$, anti-$a_5b_1$, anti-$a_5b_1$, anti-$a_vb_3$ and anti-$b_1$ integrin monoclonal antibodies on ice for 30 min. Cells were washed, resuspended in defined media, and seeded onto dishes pre-coated with 100 nM P176 and subjected to cell adhesion assays. The use of single dose (10 mg/ml) anti-integrin monoclonal antibody for C2C12-$a_2$+cell adhesion blocking assay was considered optimal. Cold (4° C.) PBS, pH 7.4 containing 1 mM of $Ca^{2+}$ and $Mg^{2+}$ was used for washing cells. Statistical analyses were performed as described (64).

Recombinant I-domain of $\alpha_2$ Integrin Subunit

Cloning, expression, and purification of the I-domain of $\alpha_2$ integrin have been described previously (65). In brief, a DNA fragment encoding the I-domain of $\alpha_2$ integrin subunit was amplified by PCR from a human hepatoma cDNA library and subcloned into the expression vector pQE30 (Qiagen Inc., Chatsworth, Calif.). The accuracy of the DNA sequence was verified by dideoxy DNA sequencing (Lonestar Lab). Large-scale expression and purification of the recombinant $\alpha_2$-I were carried out using $Ni^{+2}$-chelating affinity chromatography, as described (62).

Surface Plasmon Resonance (SPR) Analysis

Measurements were performed at room temperature in a BIACORE 3000 instrument (BIAcore, Uppsala, Sweden) as described previously (65). Briefly, 990 response units (RU) of P176Scl and 717 RU of P181Scl proteins were immobilized onto the flow cells on a CM5 chip. Different concentrations of $\alpha_2$-I proteins in HBS (25 mM HEPES, 150 mM NaCl, pH 7.4) buffer containing 5 mM β-mercaptoethanol, 1 mM $MgCl_2$ and 0.05% octyl-D-glucopyranoside were passed over these surfaces at 20 μl/min for 6 min. Regeneration of the Scl protein surface was achieved by running 10 μl of a solution of 0.01% SDS. Binding of $\alpha_2$-I to a reference flow cell, which had been activated and deactivated without the coupling of proteins, was also measured and was subtracted from the binding to Scl protein-coated chips.

SPR sensorgrams from different injections were overlaid using the BIAevaluation software (BIAcore AB). Data from the equilibrium portion of these sensorgrams were used for Scatchard analysis. Based on the correlation between the SPR response and change in soluble I-domain protein binding to the immobilized Scl proteins, values for the binding ratio, $n_{bound}$, and the concentration of free protein, [P]free, were calculated using the equations described previously (65). Scatchard analysis was performed by plotting $n_{bound}/[P]_{free}$ against $n_{bound}$, in which the negative reciprocal of the slope is the dissociation constant, $K_D$ and the X-intercept is the number of binding interactions, n.

Biochemical Methods

Cells were serum-starved overnight, detached and maintained in suspension (Sus) for 45 minutes at room temperature. Cells were then replated onto dishes coated with indicated substrates. After 30 or 60 min cells were washed with cold PBS, pH 7.4, and solubilized in cell extraction buffer (50 mM HEPES, pH 7.5, 150 mM NaCl, 1% Triton X-100, 10 mM sodium fluoride, 1 mM sodium pyrophosphate, 2 mM sodium orthovanadate and with various protease inhibitors freshly added) for 30 minutes on ice. Extracts were centrifuged at 21,000×g for 30 minutes at 4° C. to remove insoluble material.

Protein concentrations of the resulting lysates were determined by the Bio-Rad DC protein assay. For immunoprecipitation analyses, cell lysates were pre-adsorbed with mouse IgG-agarose beads at 4° C. for 1 hour. Immunoprecipitation, immunoblotting, and detection protocols were performed as described previously (64,66). For immunoprecipitation, 2–3 mg of antibodies were used for each sample. For immunoblotting analyses, antibodies were prepared at a concentration of 0.5–2 mg/ml in 1×TBS, pH 7.4, with 3% BSA.

EXAMPLE 2

Characterization of Recombinant Scl Proteins

Previous studies demonstrated that recombinant proteins expressed in eukaryotic systems could successfully be used to study the structure and organization of mammalian proteins with collagenous domains. A series of recombinant polypeptides generated in a prokaryotic (E. coli) expression system derived from either the Scl1.1, i.e., a Scl1 protein from a serotype M1 GAS, or the Scl2.28, i.e., a Scl2 protein from a M28-type GAS, protein that contain collagen-like regions composed of continuous GXY repeats was examined (FIG. 1A).

These two related proteins were selected for structural studies because they were both expressed by the parental GAS isolates and they differed significantly in their primary amino acid sequence. The collagen-like region (CL) is composed of 50 and 79 GXY repeats in Scl1.1 and Scl2.28, respectively. The amino-terminal segment of each protein, called the variable (V) region, is composed of noncollagenous sequence and consists of 67 amino acids in Scl1.1 and 73 amino residues in Scl2.28.

Figure 1B:
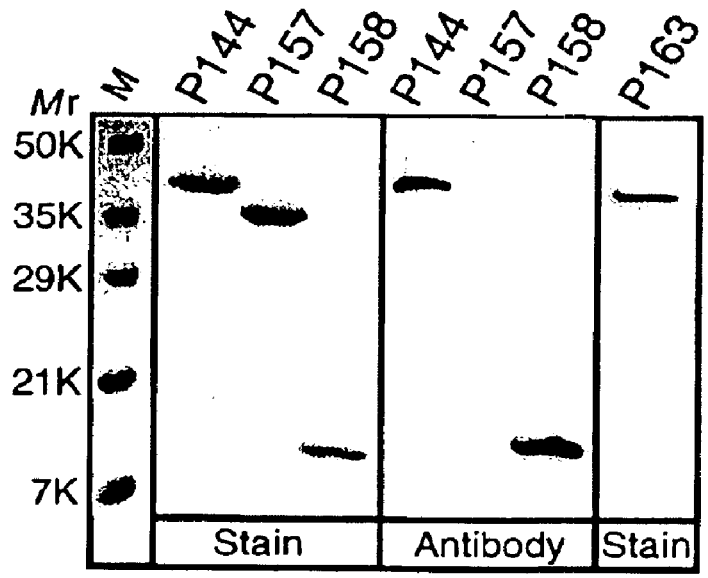

To examine the structural organization of Scl1, three recombinant proteins, P144, P157, and P158, were constructed representing the combined VCL regions, the CL region, and the V region, respectively (FIG. 1A). Wild type streptococcal Scl1.1 migrates aberrantly in denaturing SDS-PAGE. Similarly, the recombinant P144 and P157 also migrates aberrantly whereas P158 did not (FIG. 1B, left). Therefore, the recombinant protein identities were confirmed by amino-terminal sequencing and their masses of 26.8, 18.5, and 9.4 kDa, respectively, were verified by mass spectrometry analyses.

Furthermore, both P144 and P158 reacted with the V region-specific antibodies, whereas P157 did not (FIG. 1B, right). A recombinant protein P163 containing the combined VCL regions of the Scl2.28 was generated and purified. Recombinant P163 contains 79 GXY repeats in the collagen-like region and 72 amino acids in the V region. P163 ($M_r$=33.8) also migrated aberrantly in SDS-PAGE and its identity was confirmed by amino-terminal sequencing.

Figure 1D:
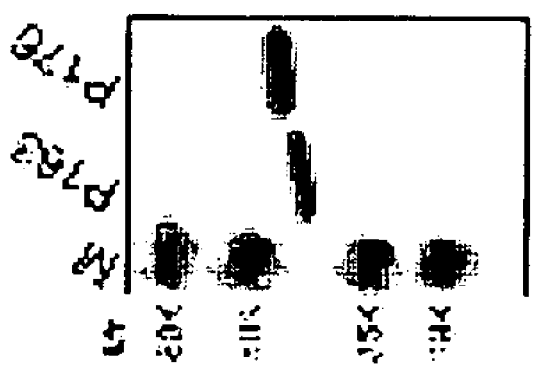
Figure 1C:
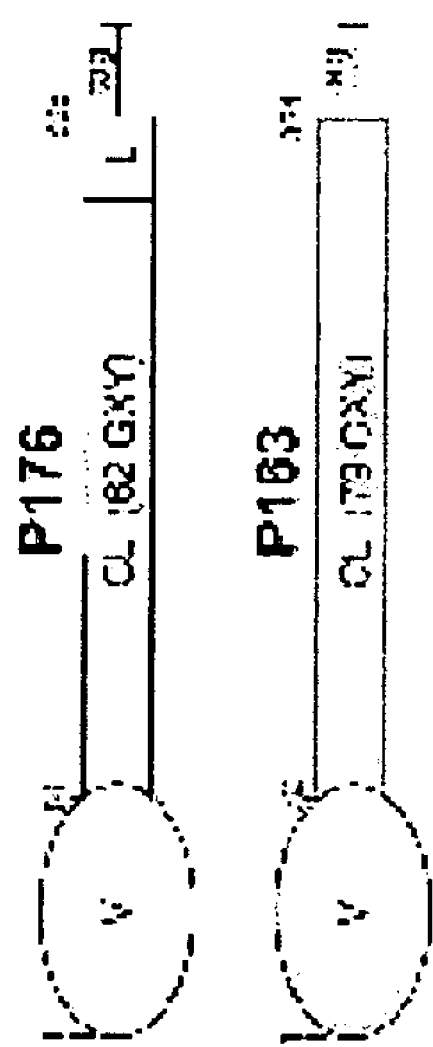

The recombinant P176 protein has an 84 amino-acid long V region followed by a CL region that includes 62 GXY triplets. It adopted a triple-helical conformation and formed lollipop-like structures when viewed by EM (FIG. 1C). Both P163 and P176 were affinity purified to apparent homogeneity, as seen by the presence of single bands on SDS-PAGE (FIG. 1D). The integrity of each protein sample was further verified by western immunoblotting with specific polyclonal antibodies (data not shown).

EXAMPLE 3
Multimolecular Organization of Scl Proteins

Figure 2A:
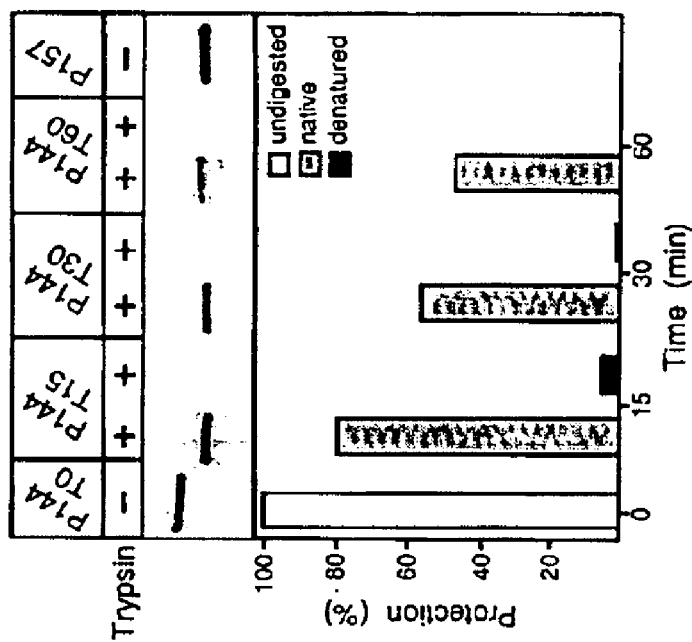
FIGS. 2A–2C demonstrate the triple helix formation by Scl1 and Scl2.

To assess the ability of Scl1 and Scl2 to assemble into polymeric structures, the electrophoretic mobilities of P144, P157, and P163 in polyacrylamide gel run in the absence of SDS before and after heat denaturation were compared (FIG. 2A). In each case the native samples produced uniform higher molecular mass bands compared with their corresponding samples that were heat-denatured before loading on a gel, results suggesting that all three proteins tested formed oligomers under nondenaturing conditions. The presence of multiple bands in denatured P144 and P163 suggested that these proteins partially renatured while running on a gel.

Figure 2B:
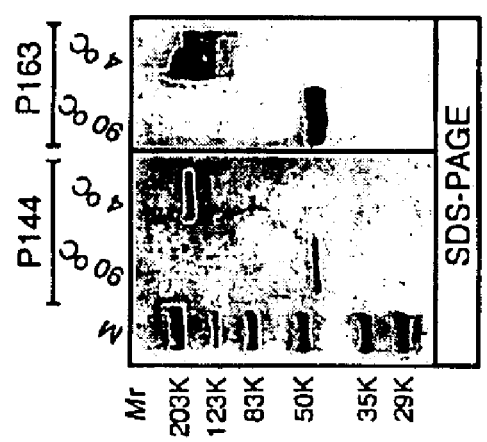

In subsequent experiments, the mobility of native and heat-denatured samples of P144 and P163 were compared in SDS-PAGE using molecular mass standards (FIG. 2B). A heat-denatured P144 ($M_r$=26.8) migrated as a 45-kDa band, whereas the nondenatured sample appeared as a single band with an apparent $M_r$ of 140–160 kDa. Similarly, the heat-denatured P163 migrated as a single band of ~43 kDa, whereas nondenatured P163 appeared heterogeneous with a predominant band that migrated in the range of 130–140 kDa. Hence, native Scl proteins form higher ordered structures and gel mobility data suggested that P144 form a stable trimer under the SDS-PAGE conditions used. Also P163 appears to form a trimer, but this putative trimer may partly dissociate in SDS-PAGE.

Figure 2C:
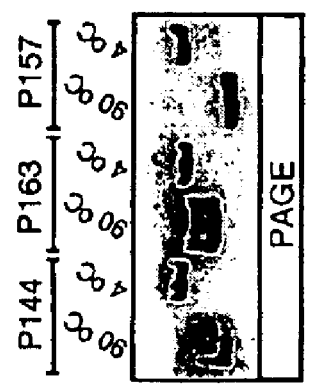

To test the formation of triple helix by Scl proteins, the susceptibility of recombinant P144 to trypsin was examined (FIG. 2C). Because triple helix is resistant to trypsin, the collagen-like domain of P144 should be protected against digestion. Native P144 was quickly trimmed to the size of the collagen-like domain corresponding to P157 and then remained relatively resistant to proteolysis. In contrast, the denatured P144 was nearly completely degraded within 15 min of the experiment. These results strongly suggested that CL region in Scl proteins is triple helical.

EXAMPLE 4
Circular Dichroism (CD) Spectroscopy of Recombinant Scl Proteins

Collagen triple helices have characteristic CD spectra with a positive ellipticity maximum at 220 nm. To examine the secondary structure composition of Scl1 and Scl2, recombinant proteins were analyzed by CD spectroscopy (FIGS. 3A–3C, solid lines). The CD spectrum of P157 at 25° C. resembled that of a collagen triple helix, with an ellipticity maximum at 220 nm in the order of $1\times10^3$ (degree $cm^2$ $dmol^1$) (FIG. 3B). Similarly, the CD spectrum of P144 corresponding to the combined VCL regions also included the characteristic shoulder at 220 nm (FIG. 3A).

The peak of the shoulder, however, was of a negative value probably due to the contribution of the secondary structure of the noncollagenous V domain. Similarly small amplitudes were previously reported for some mammalian proteins with collagenous domains including surfactant proteins and complement component C1q. The CD spectrum of the Scl2.28, recombinant P163, also had the characteristics of a collagen triple helix with ellipticity maximum at 220 nm ($\sim 2\times10^3$ degree $cm^2$ $dmol^1$) (FIG. 3C).

Figure 3G:
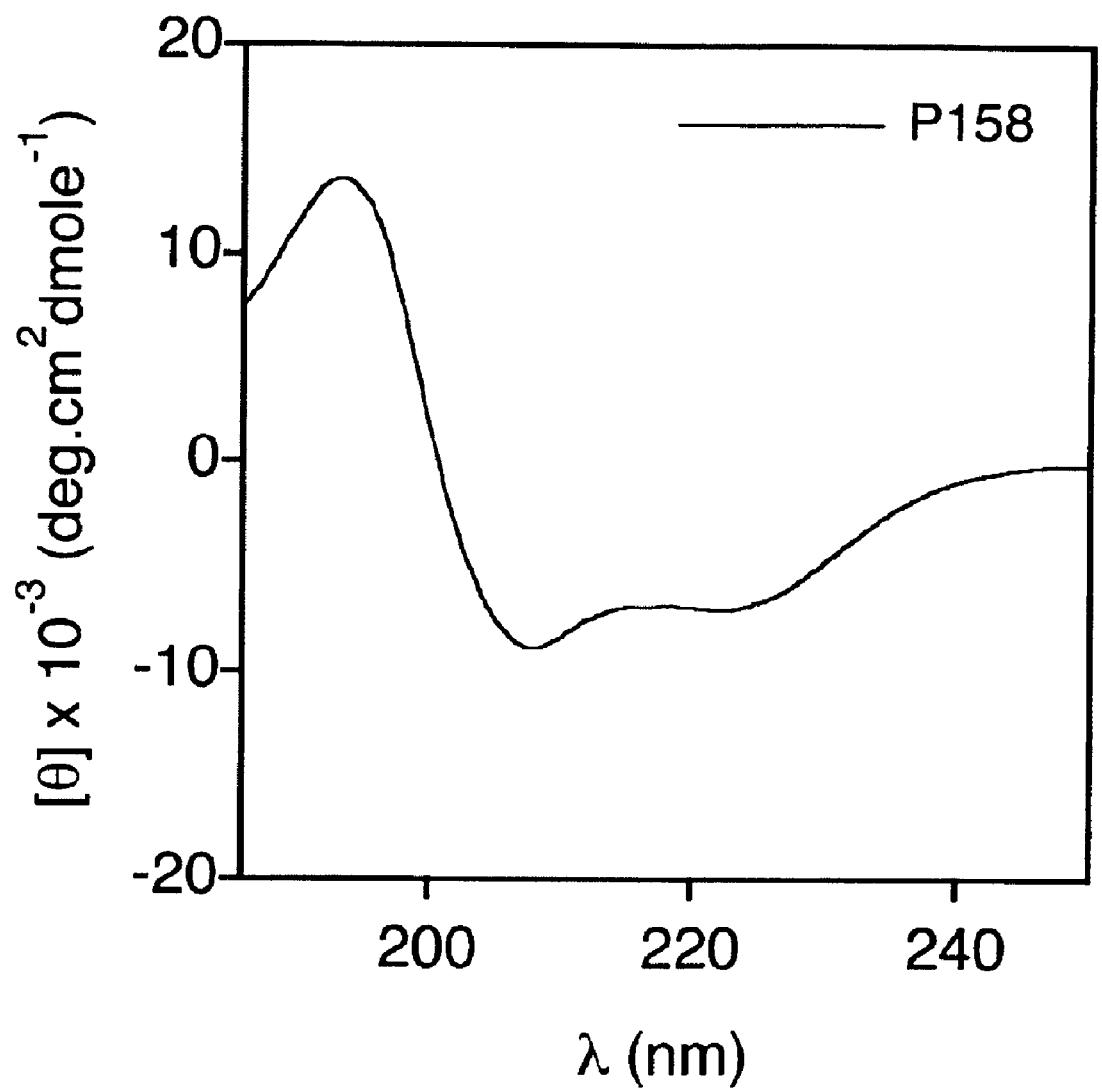

The CD spectrum of P158 (10 $\mu$M) did not include the characteristics of a collagen triple helix (FIG. 3G). Deconvolution of the spectrum indicated that the recombinant V domain consisted of 25.7% (±4.3%) a-helices, 43.6 (±10.5%) b-sheets, and 30.7% (±11.3%) other secondary structure elements.

When samples of P144 (8.1 $\mu$M), P157 (29.8 $\mu$M) and P163 (7.7 $\mu$M) were heated to 50° C., the CD spectra recorded at this temperature (FIGS. 3A–3C, broken lines) did not show the characteristic features of a collagen triple helix, e.g., the 220 nm maximum, but rather indicated a random coil structure, suggesting that the triple helix had unfolded. By monitoring the CD at 220 nm as a function of increasing temperature, the thermal unfolding of the Scl proteins were followed. The triple-helical structure in all three proteins unfolded within a very narrow temperature range (t<=6° C.), with the midpoint temperatures of $t_m$=36.4±0.4° C. for P144 (FIG. 3D), $t_m$=37.7±0.2° C. for P157 (FIG. 3E), and $t_m$=37.6±0.8° C. for P163 (FIG. 3F). The sharp transition and the $t_m$ values of these proteins are reminiscent of the transition from triple helix to random coil seen for a type I collagen, i.e. $t_m$=38° C. and t=3° C.

The thermal unfolding of the collagen-like triple helix of P144 and P163 appears to be readily reversible. When the protein samples were cooled, the ellipticity at 220 nm gradually increased (FIGS. 3D–3F), and the CD spectra of samples cooled to 4° C. again showed the characteristics of a collagen-like triple helix (FIGS. 3A and 3C, dotted lines). The signal intensities at 207 and 220 nm of the refolded proteins were lower than those recorded for the original proteins before melting, suggesting that the refolding was not complete. The attempts to refold P157 were unsuccessful, suggesting that the amino-terminal V regions present in P144 and P163 but absent in P157 might facilitate triple helix assembly. The above experiments were also performed with a slower temperature slope (10° C./h), and no obvious differences were found.

Figure 3H:
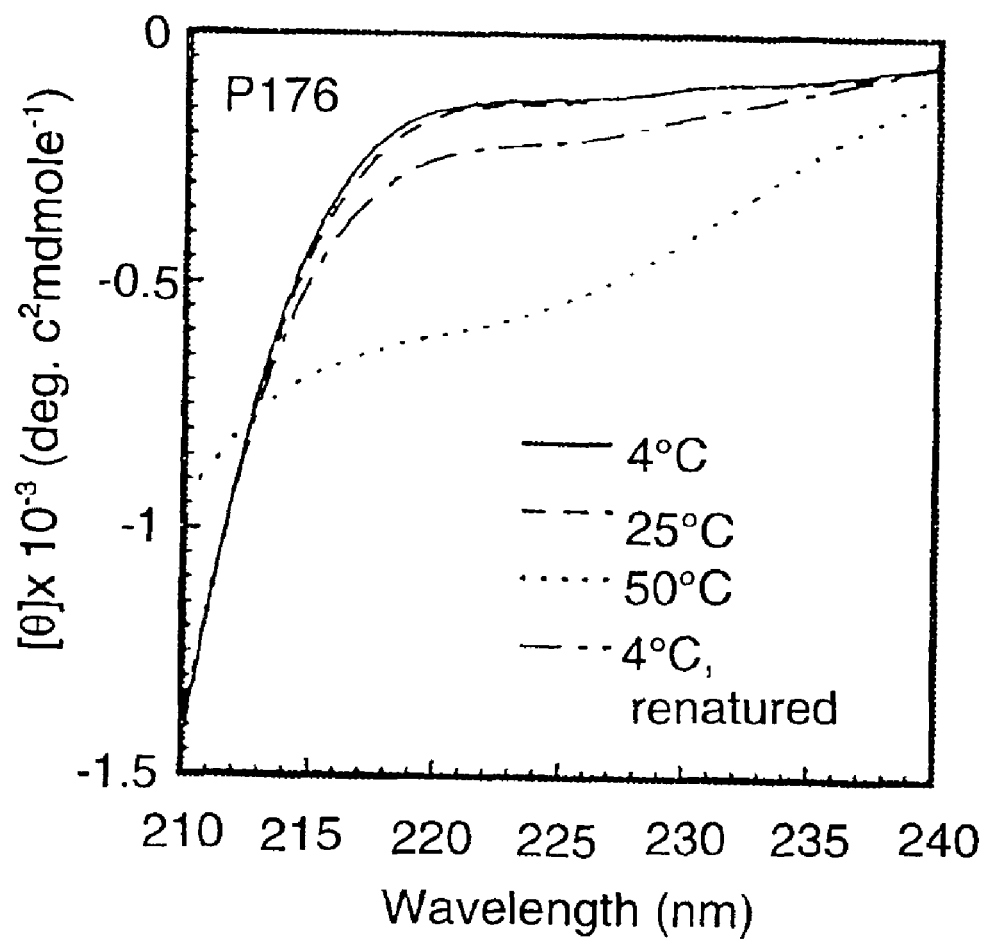

The CD spectra of P176 at 4° C. and 25° C. showed ellipticity maxima at 220 nm, which is consistent with a collagen triple helix-like structure (FIG. 3H). When the P176 sample was heated to 50° C., the CD spectrum no longer exhibited the characteristics of a triple helix, but rather indicated a random coil structure, suggesting that the triple helix had unfolded. Upon cooling to 4° C. again, the signal intensities at 220 nm had increased, indicating that the triple helix could reassemble.

EXAMPLE 5
Electron Microscopy of Scl Proteins

Figures 4D, 4E, 4F:
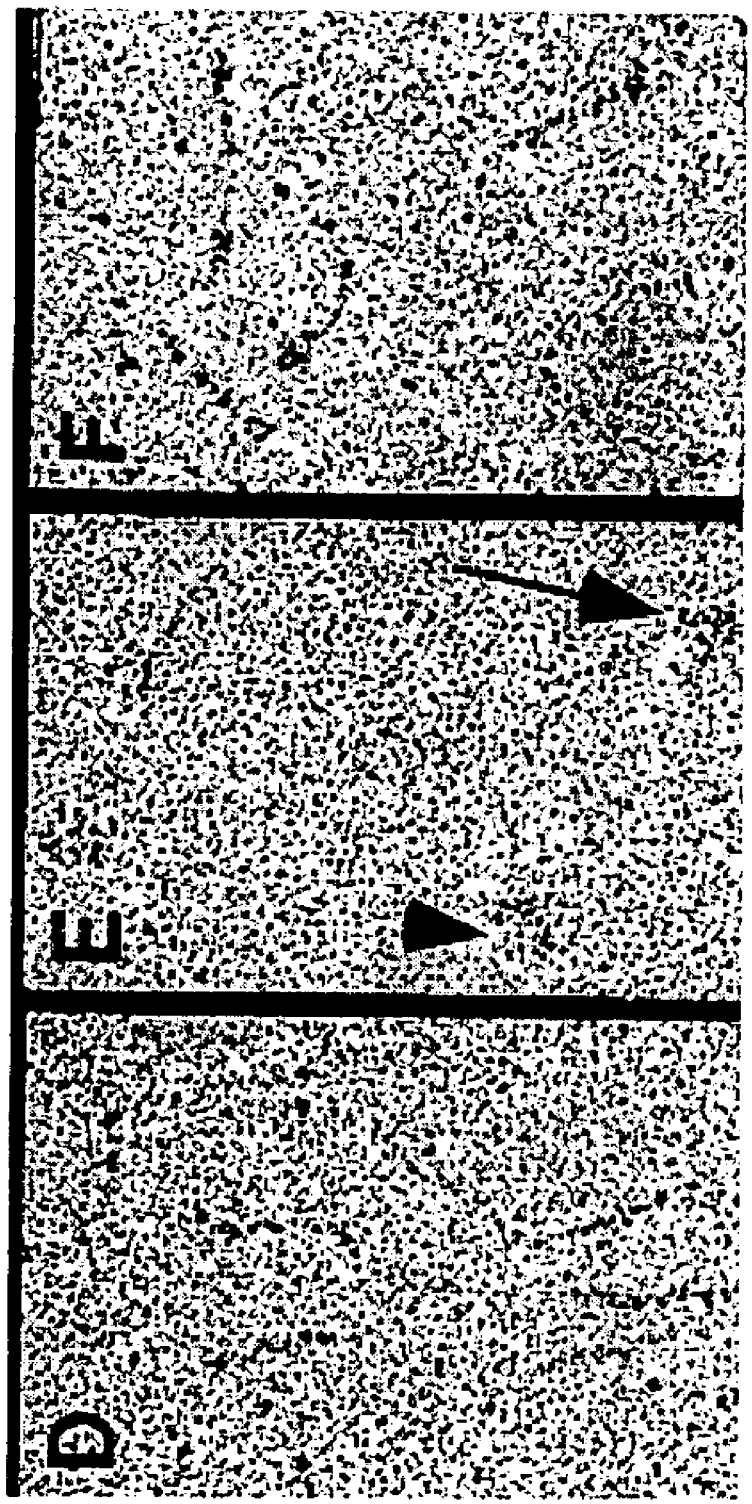

Electron microscopy of rotary shadowed samples has been used for studying the structural organization of collagens and collagen-like mammalian proteins. Examination of a rotary shadowed preparation of Scl1, e.g., recombinant P144, revealed a two-domain lollipop-like structure (FIGS. 4A–4B) and ~25% of the molecules appeared to form dimers via head-to-head interactions (FIGS. 4A and 4C). It is contemplated that the collagen-like region of Scl1 formed the lollipop stalk, whereas the globular head was made of the V region. Two lines of evidence support this hypothesis. First, the recombinant P157 protein corresponded to the CL region formed rod-shaped particles (FIG. 4D) and, secondly, the anti-V specific antibody appeared to bind to the globular heads of Scl1 (FIG. 4E). Scl2, e.g., recombinant P163, also had a two-domain lollipop-like structure (FIG. 4F); however, in contrast to Scl1 preparation, Scl2 did not appear to form head-to-head dimers.

The measured contour length, i.e., 279 particles measured, of the collagenous tail in P144 is 45.5±4.3 nm. Based on a translation of 0.286 nm per residue observed in a collagen triple helix, the 150-residue stretch encompassing 50 GXY repeats in the CL region was calculated to be 43 nm long, which correlated well with the measured length. Rod-shaped particles (n=190) of similar length 45.6±4.4 nm were seen in the P157 preparation, further confirming that the CL region of Scl1 alone formed a triple helix.

The shape of the globular domain in P144 was more heterogenous with some molecules appearing spherical and others elongated extending along the axis of the collagenous tail. The diameter of the globular domain (n=279) measured in the middle of the head perpendicularly to the axis of the tail was 8.9±2.2 nm. Considering size overestimation by 2.5 to 5 nm due to metal decoration, a diameter of 3.9–6.4 nm appeared more realistic. The latter estimate was close to the theoretical value of 3.8 nm calculated for a spherically shaped protein with a molecular mass of a trimeric V region using the equation: $d=2(3vM_r/4\pi N_A)^{1/3}$, where $M_r=25,072$, $N_A$ is Avogadro's number, and $v=0.73$ cm$^3$/g is the assumed partial specific volume.

Figure 4G:
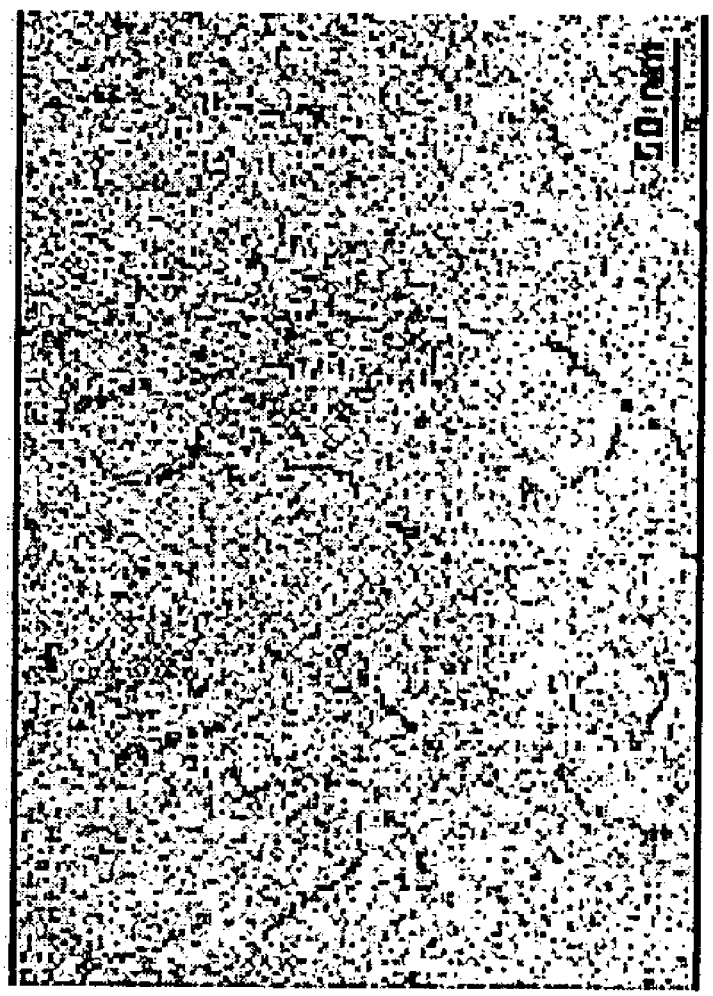

The dimensions of P163 also agreed with theoretical predictions calculated for the Scl2.28 protein. Specifically, the measured length of the collagenous domain (n=253) of 66.2±8.9 nm correlated well with the calculated value of 67.8 nm. Similarly, a diameter of the globular domain (n=124) of 7.4±0.9 nm agreed with the calculated value of 3.9 nm, considering a metal decoration component. Examination of a rotary shadowed preparation of P176 (FIG. 4G) revealed a characteristic two-domain lollipop-like structure, consistent with what has been previously reported for other Scl variants, such P163.

EXAMPLE 6
Computer Modeling

The trimeric structure of the collagen-like region of Scl1.41 and Scl2.28 was homology-modeled using SwissModel, based on the coordinates of a (Pro-Pro-Gly)$_{10}$ collagen-like peptide. The target-template alignment was guided by superposition of Gly residues. Energy minimization in vacuo was carried out using GROMOS96 to relieve short contacts and improve local stereochemistry. Interactions involving the side chains have not been modeled explicitly.

Figure 5A:
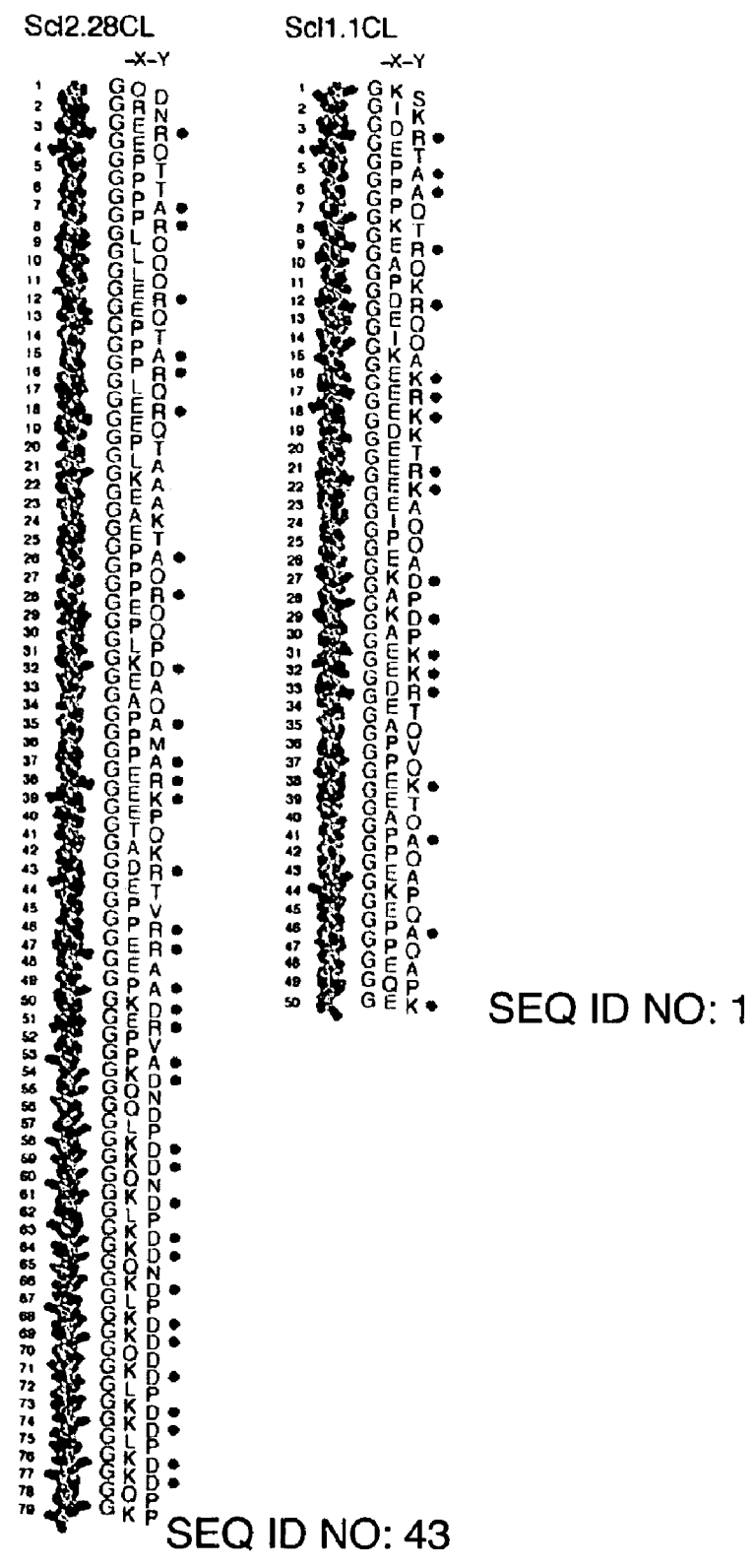

The amino acid sequence of the collagenous domains of Scl1.41 and Scl2.28 was fitted onto the structure of a regular polyGPP triple helix (FIG. 5A). All steric clashes between the polypeptide backbone and the newly introduced side chains were relieved by energy minimization without significant alteration of the main chain torsion angles. Moreover, the lengths of the Scl1.1CL and Scl2.28CL models, 42.3 nm and 67.1 nm, respectively, agreed well with the experimentally determined lengths of these regions, as determined in Example 5, providing further evidence supporting the validity of the models.

Although the CL regions in Scl1.41 and Scl2.28 are both composed of continuous GXY repeats, they show remarkable primary sequence differences. The five most frequent triplets in Scl1.1 GEK, GPQ, GEA, GET, and GPA, account for 48% of all triplets in this protein but represent only 10% of the triplets in Scl2.28. Similarly, the GKD, GAQ, GPA, GER, and GLP triplets make up 55.9% of the collagen-like segment in Scl2.28 but account for only 16% of the triplets in Scl1.1. Fifty GXY motifs of Scl1.1CL contain 21 distinct triplets, seven of which are not found in Scl2.28. Conversely, 12 out of 26 distinct triplets are specific to Scl2.28CL.

In addition, those GXY motifs that are common to both Scl proteins are arranged in different orders in Scl1.1CL and Scl2.28CL. Despite the significant sequence variation in the CL region of the two proteins, these could both successfully be modeled on a polyGPP structure. Thus the ability to form a collagen-like triple helix structure is not unique to a particular Scl sequence but may be the property of other prokaryotic proteins containing repeated GXY motifs.

EXAMPLE 7
Collagen-Like Protein Promotes Cell Adhesion and Spreading

Figure 6A:
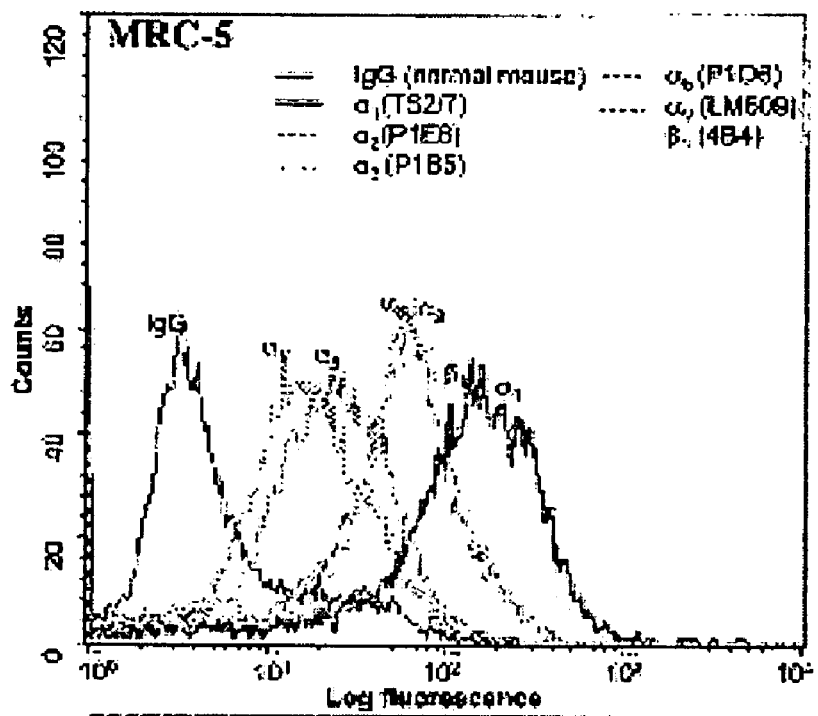
Figure 6B:
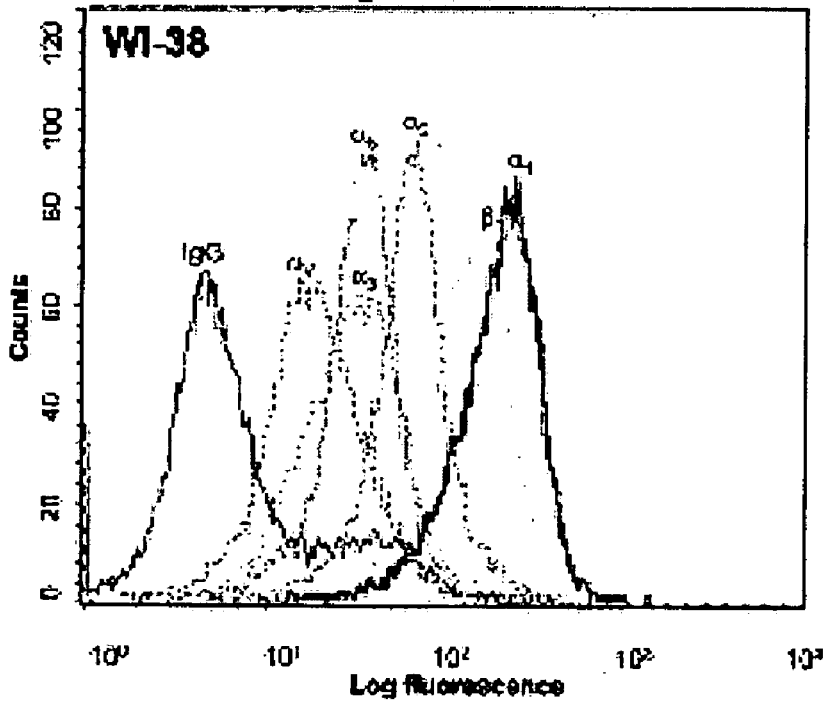

The expression levels of various integrin chains on MRC-5 and WI-38 cells were determined using fluorescence activated cell sorting (FACS). Both cell types expressed collagen binding $\alpha_1\beta_1$ and $\alpha_2\beta_1$ integrins at comparable levels, as well as $\alpha_3\beta_1$, $\alpha_5\beta_1$ and $\alpha_{v1}$ which presumably partners with $\beta_5$ (FIGS. 6A–6B).

Next, cell adhesion assays were performed on immobilized recombinant P163 and P176 proteins or known adhesive extracellular matrix (ECM) proteins. P176 served as a substrate for the attachment of both MRC-5 and WI-38 cells, similar to fibronectin (FN), type IV collagen (Col IV), and type I collagen (Col I). The extent of cell attachment to these substrates depended on the amount of protein used to coat the wells and the incubation time of the cells (FIGS. 6C–6D). In contrast, P163 did not support cell adhesion under the same experimental conditions.

Figure 7A:
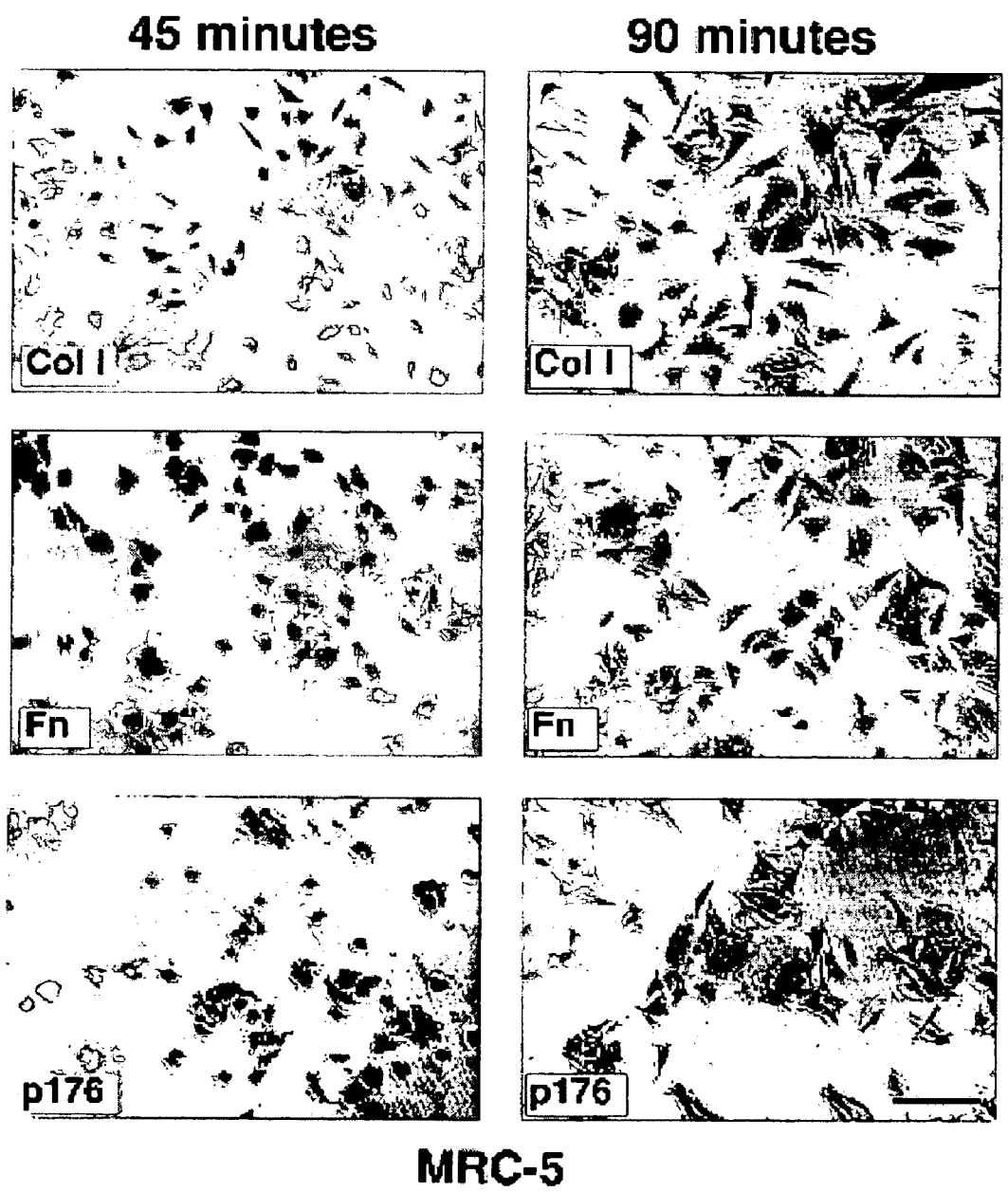
FIGS. 7A–7C demonstrate adhesion and spreading of MRC-5 and WI-38 cells on recombinant Scl protein. Cells detached and suspended in defined media were plated on microtiter plates coated with 100 nM of P176 or 1 mg/ml of either Col I or FN. After the indicated time points, plates were washed, fixed and stained. Representative photomicrographs of cells stained with eosin and hematoxylin are shown following 45 and 90 minutes of adhesion in MRC-5 cells (FIG. 7A) and WI-38 cells (FIG. 7B) at 20× magnification; Bar 200 μm. Cells were grown on coverslips coated with these substrates (FIG. 7C). After 90 min of permissive adhesion and spreading, cells were fixed and stained with TRITC-phalloidin (i, ii, and iii) and DAPI (iv, v, and vi) to visualize F-actin organization and nucleus. Magnification 100×; Bar 10 μm.
Figure 7B:
Figure 7B:
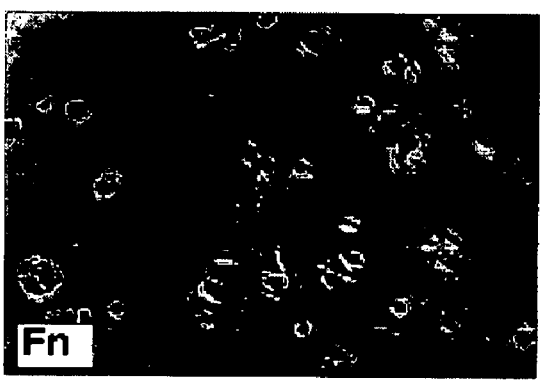
Figure 7B:
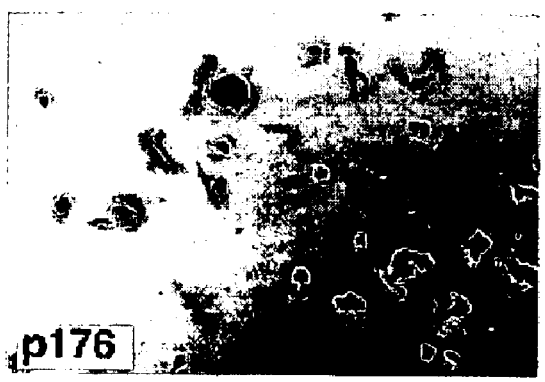
Figure 7B:
Figure 7B:
Figure 7B:
Figure 7C:
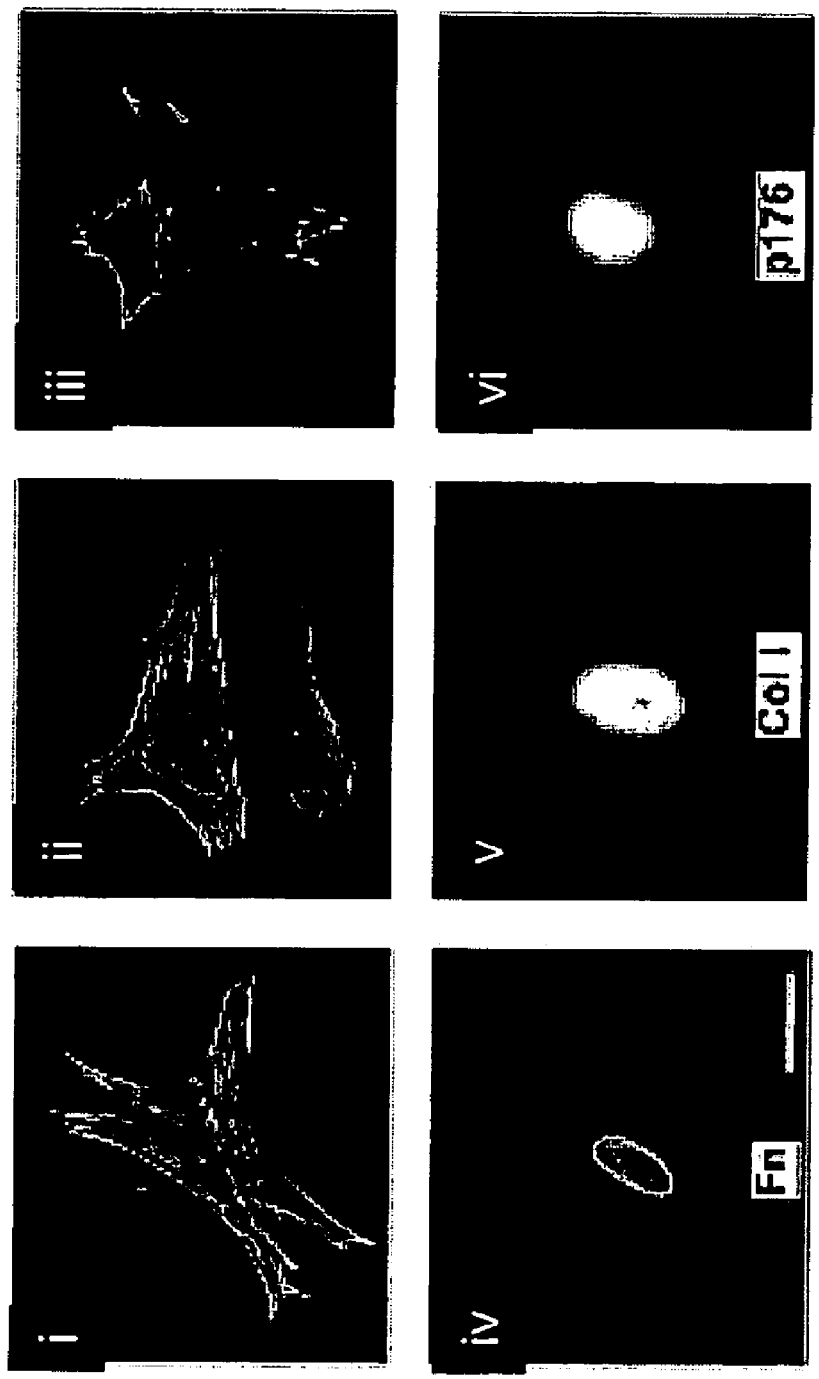

The cell attachment results were complemented with cell spreading assays. Detached WI-38 and MRC-5 cells were allowed to reattach onto dishes coated with FN, Col I and P176 substrates for 45 or 90 minutes. P176 induced considerable cell spreading, as did the positive control adhesion substrates (FIGS. 7A–7B). Under the same conditions, cell attachment to P163 was negligible and the few cells that did attach did not undergo cell spreading, but were removed by gentle washing (data not shown).

Cell spreading was further examined by evaluating cell morphology in fluorescent-stained MRC-5 cells (FIG. 3C). Cells incubated on substrates of P176, Fn or Col I adopted a morphology characteristics of fully spread fibroblasts with a defined nucleus (DAPI stained) surrounded by an extended cytoplasm. The assembly of actin filaments into stress fibers was demonstrated in cells stained with tetramethyl-rhodamine B isothiocyanate (TRITC)-phalloidin. Furthermore, when MRC-5 cells were incubated on P176 substrates for a prolonged period (~2–3 hours), they exhibited an elongated and contractile appearance, similar to these cells incubated on Col I (data not shown). These results show that Scl protein interacts with integrin(s) to induce cell attachment and promote cell spreading.

EXAMPLE 8
Cell Adhesion Activity of P176 is Mediated via its Collagen-like Region To delineate the regions of the P176 protein responsible for it ability to support cell adhesion and spreading activity, two chimeric recombinant proteins, P181 and P182, were generated by exchanging domains between the putative integrin-binding variant P176 and the non-interacting variant P163 (FIGS. 8A and 8D). The V region of P163 was replaced with the corresponding P176-V region to create P181. The P176-CL region was then substituted for the corresponding CL region of P181, originally a P163-CL sequence, resulting in P182. Neither of the chimeric proteins contained the repeats of the linker region found in P176. Analyses of purified recombinant P181 and P182 proteins by electron microscopy and far UV CD spectroscopy suggest that both chimeric proteins behaved as Scl proteins (41).

Both P181 and P182 were able to form collagen-like triple helices, as determined by CD (FIGS. 8B and 8E) and electron microscopy (FIGS. 8C and 8F). Cell adhesion assays showed that only P182 which contains the P176-CL region, but not P181 which contains P176-V and P163-CL domains, supported cell adhesion activity in a time- and dose-dependent manner in both the MRC-5 and WI-38 cell lines (FIGS. 8G-8H). This data demonstrates that the collagenous CL region, but not the globular V, region of P176 supports cell adhesion, possibly through interacting with one or more of the collagen-binding integrins.

EXAMPLE 9
P176 Interacts Specifically with the $\alpha_2\beta_1$ Collagen-binding Integrin To determine which collagen-binding integrin(s) recognizes P176, we tried to inhibit cell attachment using a panel of monoclonal antibodies directed against the extracellular segments of human integrins. The ability of MRC-5 cells to attach onto plates coated with P176 was measured in the presence of increasing concentrations of anti-$\alpha_1\beta_1$, -$\alpha_2\beta_1$, -$\alpha_3\beta_1$, -$\alpha_v\beta_3$, -$\alpha_5\beta_1$, or -$\beta_1$ integrins adhesion-blocking monoclonal antibodies, or in the presence of EDTA, a metal ion chelating agent (FIG. 9A). Interestingly, only anti-$\alpha_2\beta_1$ and -$\beta_1$ integrin antibodies inhibited cell adhesion activities in a dose dependent manner. In contrast, antibodies against other integrins, including those against the integrins $\alpha_1\beta_1$, $\alpha_3\beta_1$, $\alpha_5\beta_1$ and $\alpha_v\beta_3$ did not block cell attachment. As expected, EDTA also inhibited cell attachment in a dose-dependent manner. These data show that $\alpha_2\beta_1$ integrin is a cellular receptor for the P176 protein.

To further examine the role of the $\alpha_2\beta_1$ integrin in cell adhesion to P176, collagen receptor deficient C2C12 myoblast cells, and C2C12 cells stably expressing the human wild-type $\alpha_2$ integrin subunit (designated C2C12-$\alpha_2$+) were used. Upon expression in C2C12 cells, wild-type 2 polypeptide combines with the endogenous $\beta_1$ subunit, to form a functional $\alpha_2\beta_1$ integrin (24). Col I, Col IV, FN, and VN were included as positive controls in cell adhesion assays. As expected, Col I and Col IV failed to promote adhesion of parental C2C12 cells, in contrast, both ECM proteins supported adhesion of C2C12-$\alpha_2$+ cells (FIG. 9B). Consistent with previous report, FN and VN supported attachment of both C2C12 parental and C2C12-$\alpha_2$+ cells (FIG. 9B).

If C2C12-$\alpha_2$+ adheres to P176 through integrins(s), does adhesion blocking anti-integrin antibodies inhibit their interactions? The attachment of both parental and C2C12-$\alpha_2$+ cells to BSA (negative control) and P163 were insignificant (FIG. 9C). Similarly, adhesion of parental C2C12 cells to P176 was also negligible (FIG. 9C). In contrast, C2C12-$\alpha_2$+ cells attached to P176 protein productively and this interaction was blocked effectively by anti-$\alpha_2\beta_1$ and anti-, integrin monoclonal antibodies (FIG. 9C). Clearly, these data indicate that adhesion of cells to P176 is mediated specifically by $\alpha_2 b_1$ integrin.

These findings further support the hypothesis that cell adhesion is mediated through $\alpha_2\beta_1$. Furthermore, because P176 interacts directly with $\alpha_2\beta_1$ integrin, the data may support a caveolae-mediated entry route for certain *S. pyogenes* strains. Both the paracellular and the caveolar mechanisms may be advantageous for the propagation of GAS and for its pathogenicity.

EXAMPLE 10
The I-Domain of $\alpha_2$ Integrin ($\alpha_2$-I) Interacts with P176 but not P181

The I-domain of the $\alpha$ components of collagen binding integrins have been demonstrated to directly bind to specific site in triple helix collagens (62). To study if the I-domain of $a_2$ integrin subunit binds to P176, $\alpha_2$-I was expressed as a recombinant protein and its binding to P176 and P181 examined by surface plasmon resonance (SPR) spectroscopy. Different concentrations of $\alpha_2$-I were passed over Bia-core chips to which the recombinant Scl proteins had been coupled.

Figures 10A, 10B, 10C:
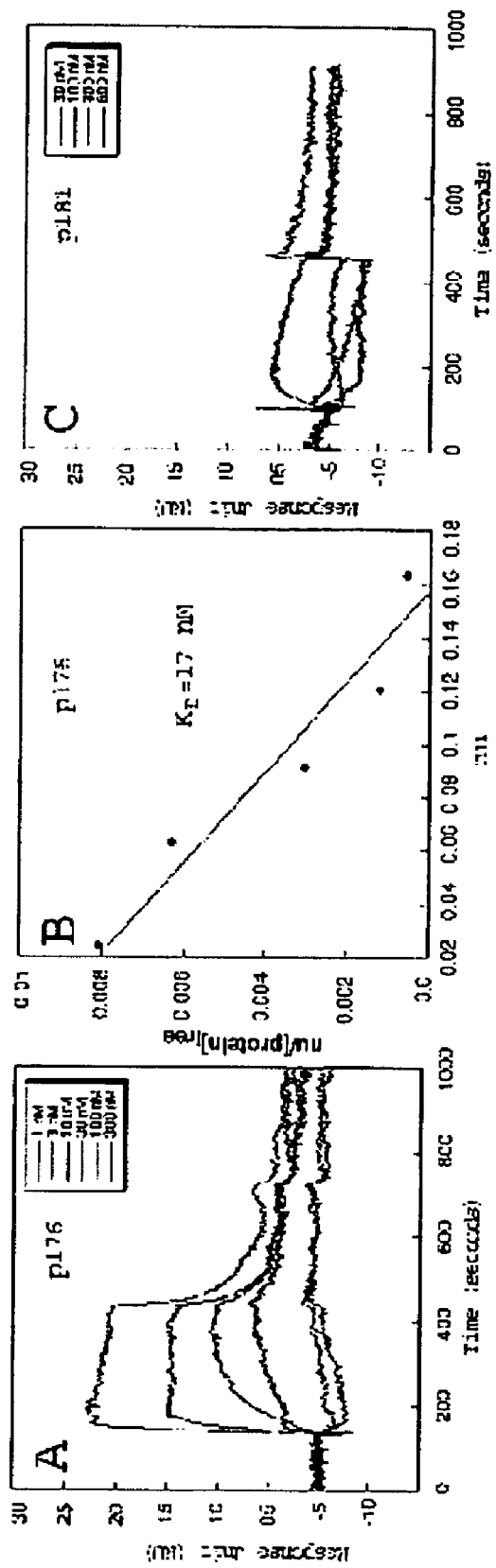
FIGS. 10A–10C show surface plasmon resonance (SPR) analyses of $\alpha_2$ integrin subunit I-domain ($\alpha_2$-I) binding to recombinant Scl proteins. Different concentrations of $\alpha_2$-I were injected at a flow rate of 20 ml/minute for 6 minutes in the presence of 1 mM $MgCl_2$. Representative sensorgrams of the relative SPR responses of $\alpha_2$-I over immobilized P176 (FIG. 10A) and P181 (FIG. 10B) are shown. The responses of $\alpha_2$-I over a blank cell were subtracted. Scatchard plot analysis was performed using the responses at the steady state portion of the sensorgrams, as previously described (65). $n_{bound}$, binding ratio; $[P]_{free}$, free protein concentration. The dissociation constants ($K_D$) for $\alpha_2$-I over P176 (FIG. 10C) in absence of 3 mM EDTA is ~17 nM. Similar results were obtained from SPR measurements when P176 was passed over immobilized $\alpha_2$-I domain protein (data not shown). Data are representative of those obtained from at least two to three separate experiments, with similar results.

A concentration dependent binding of $\alpha_2$-I to P176 was noted with rapid on and off rates and defined equilibrium (FIG. 10A). A $K_D$ of 17 nM was calculated from a Scatchard-plot of the equilibrium data (FIG. 10B). No significant binding was observed when increasing concentrations (up to 300 nM) of $a_2$-I were run over P181 (FIG. 10C). These results demonstrate that P176 contains a site to which $\alpha_2$-I domain binds with high affinity.

EXAMPLE 11
P176 Induces Tyrosine Phosphorylation of p125FAK, p130CAS, Paxillin, and JNK Cell adhesion-induced tyrosine phosphorylation of p125FAK, p130CAS, paxillin proteins and JNK are considered to be integrin-mediated signaling events (36). The phosphorylation state of these proteins was evaluated to determine whether P176 induces $\alpha_2\beta_1$ integrin signaling in this manner. Cells kept in suspension were used as a negative control and cells adhering to Col I and FN substrates were used as positive controls.

Cells were incubated with the various substrates for 30 min, a time required for FAK activation, and the lysates were analysed as shown in FIGS. 11A–11H. FIG. 11A shows that the phosphorylation of p125FAK at tyrosine-397 is markedly increased in response to adhesion onto P176, FN, and Col I. Since paxillin and p130CAS proteins are key focal adhesion-related molecules that undergo phosphorylation in response to activation of p125FAK, the tyrosine phosphorylation states of these proteins also was examined.

Immune complexes were analyzed by immunoblotting with an anti-phospho-tyrosine antibody. Like p125FAK, both p130CAS and paxillin were phosphorylated in response to adhesion onto P176, FN, and Col I (FIGS. 11C and 11E). In contrast, these proteins did not exhibit any change in tyrosine phosphorylation state in the cells that remained in suspension, mimicking the unattached cells on P163.

Similarly, phospho-JNK immunoblotting analysis of total lysates showed that JNK was phosphorylated in response to adhesion onto P176, FN and Col I (FIG. 11G), but not under control conditions (cells in suspension). All blots were stripped and reprobed with antibodies directed against the corresponding proteins, or a non-phospho-specific antibody in the case of FAK and JNK, to verify that equivalent amounts of proteins were loaded in all the samples (FIGS. 11B, 11D, 11F, and 11H). The data indicate that $a_2b_1$ integrin dependent adhesion to P176 induces phosphorylation of FAK, CAS, Paxillin and JNK proteins.

The data indicate that fibroblast cells attach and spread on P176 and that these events are associated with the formation of focal adhesion contacts where vinculin and talin localize. P176-mediated integrin clustering and signaling is consistent with the time-dependent activiation of FAK and JNK protein kinases observed in fibroblasts plated on P176. In fibroblast and endothelial cells, p38 MAP kinase and ATF-2 are activated in response to $\alpha_2\beta_1$ integrin ligation (67–68). Thus P176 promotes tyrosine phosphorylation of integrin signaling molecules in fibroblasts. This is consistent with the hypothesis that Scl1.41 is a bacterial collagen that induces signaling through the cell adhesion receptor $\alpha_2\beta_1$ integrin.

The following references are cited herein:
1. Prockop, D. J. 1998. *Matrix Biol.* 16:519–528.
2. Ramachandran, G. N. 1988. *Int. J. Pept. Protein. Res.* 31:1–16.
3. Brodsky, B., and N. K. Shah. 1995. *FASEB J.* 9:1537–1546.
4. Brodsky, B., and J. A. Ramshaw. 1997. *Biol.* 15: 545–554.
5. Uitto, et al., 1973. *Biochem. Biophys. Res. Comm.* 55: 904–911.
6. Uitto, J., and D. J. Prockop, 1974. *Biochemistry.* 22:4586–4591.
7. Pihlajaniemi et al., 1981. *Biochemistry.* 20:7409–7415.
8. Leblond, C. P. 1989. *Anat. Rec.* 224:123–138.
9. Berisio, et al., 2002. *Protein Sci.* 11:262–270.
10. Sellar, et al., 1991. *Biochem. J.* 274:481–490.
11. Reid, K. B. M. 1993. *Biochem. Soc. Trans.* 21:464–468.
12. Engel, J. 1997. *Science.* 277:1785–1786.
13. Charalambous, et al., 1988. *EMBO J.* 7:2903–2909.
14. Smith, et al., 1998. *Science.* 279:834.
15. Ferretti, et al., 2001. *Proc. Natl. Acad. Sci. USA.* 98:4658–4663.
16. Rasmussen, et al., 2003. *J. Biol. Chem.* 278:32313–32316.
17. Hynes, R. O. 1987. *Cell.* 27:549–554.
18. Santoro, et al., 1995. *Thromb. Haemost.* 74:813–821.
19. Ruoslahti, E. 1991. *Integrins. J. Clin. Invest.* 87:1–5.
20. Albelda, S. M., and C. A. Buck. 1990. *FASEB J.* 11: 2868–2880.
21 Cheresh, D. A. 1992. *Clin. Lab. Med.* 12:217–236.
22. Larson, et al., 1990. *Immunol. Rev.* 114:181–217.
23. Newham, et al., 1996. *Mol. Med. Today.* 2:304–313.
24. Tiger, et al., 2001. *Dev. Biol.* 237:116–129.
25. Veiling, et al., 1999. *J. Biol. Chem.* 274:25735–25742.
26. Camper, et al., 2001. *Cell Tissue Res.* 306:107–116.
27. Kern, et al., 1993. *Eur. J. Biochem.* 215:151–159.
28. Kern, et al., 1994. *J. Biol. Chem.* 269:22811–22816.
29. Kern, et al., 1998. *J. Cell Physiol.* 176:634–641.
30. Nykvist, et al., 2000. *J. Biol. Chem.* 275:8255–8261.
31. Xiong, et al., 2003. *J. Thromb. Haemost.* 1:1642–1654.
32. Liddington, et al., 1998. *Structure.* 6:937–938.
33. Heino, J. 2000. *Matrix Biol.* 19:319–323.
34. Gullberg, et al., 2002. *Prog. Histochem. Cytochem.* 37:3–54.
35. Yamada, K. M. 1997. *Matrix Biol.* 16:137–141.
36. Giancotti, et al., 1999. *Science.* 285:1028–1032.
37. Stupack, et al., 2002. *J. Cell. Sci.* 115:3729–3738.
38. Martin, et al., 2002. *Science.* 296:1652–1653.
39. Miranti, C. K., and J. S. Brugge. 2002. *Nat. Cell Biol.* 4:E83–90.
40. Alahari, et al., 2002. *Int. Rev. Cytol.* 220:145–184.
41. Lukomski, et al., 2000. *Infect. Immun.* 68:6542–6553.
42. Lukomski, et al., 2001. *Infect. Immun.* 69:1729–1738.
43. Rasmussen, et al., 2000. *Infect. Immun.* 68:6370–6377.
44. Rasmussen, et al., 2001. *Infect. Immun.* 40:1427–1438.
45. Whatmore, A. M. 2001. *Microbiology.* 147:419–429.
46. Okada, et al., 1995. *Proc. Natl. Acad. Sci. USA.* 92:2489–2493.
47. Schrager, et al., 1998. *J. Clin. Invest.* 101: 1708–1716.
48. Stockbauer et al., 1999. *Proc. Natl. Acad. Sci. USA.* 96:242–247.
49. Cue, et al., 1998. *Infect. Immun.* 66:4593–4601.
50. Cywes, et al., 2001. *Nature.* 414:648–652.
51. Patti, et al., 1994. *Curr. Opin. Cell Biol.* 6:752–758.
52. Ozeri, et al., 1998. *Mol. Microbiol.* 30:625–637.
53. Rohde, et al., 2003. *Cell. Microbiol.* 5:323–342.
54. Glenney et al., 1992, *Proc. Natl. Acad. Sci. USA.* 89:10517–10521.
55. Rothberg, et al., 1992. *Cell.* 68:673–682.
56. Wary, et al., 1998. *Cell.* 94:625–634.
57. Wary, et al., 1996. *Cell.* 87:733–743.
58. Wei, et al., 1996. *Science.* 273:1551–1555.
59. Kagawa, et al., 2000. *Proc. Natl. Acad. Sci. USA.* 97:2235–2240.
60. Molinari, et al., 1997. *Infect. Immun.* 65:1357–1363.
61. Cue, et al., 2000. *Proc. Natl. Acad. Sci. USA.* 97: 2858–2863.
62. Xu, et al., 2000. *J. Biol. Chem.* 275:38981–38989.
63. Sakai, et al., 1994. *Methods Enzymol.* 245:29–52.
64. Humtsoe, et al., 2003. *EMBO J.* 22:1539–1554.
65. Rich, et al., 1999. *J. Biol. Chem.* 274:24906–24913.
66. Wary, et al., 1999. *Methods Mol. Biol.* 129:35–49.
67. Xu. et al., 2001. *Biochem. J.* 355:437–447.
68. Ivaska, 1999. *J. Cell Biol.* 147:401–416.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A recombinant triple helical protein, comprising: one or more domains comprising one or more amino acid sequences shown in SEQ ID Nos: 2–9, 15, 37, and/or consisting of SEQ ID Nos: 1 and 10, thereby forming a triple helical structure.

2. The recombinant triple-helical protein of claim 1, further comprising one or more triple helical domains of a mammalian collagen.

3. The recombinant triple-helical protein of claim 2, wherein said mammalian collagen is human collagen.

4. The recombinant triple-helical protein of claim 2, wherein said triple helical protein is a fusion protein.

5. A recombinant collagen-like protein, comprising: one or more domains having an amino acid sequence of shown in SEQ ID NO: 15.

6. The recombinant collagen-like protein of claim 5, further comprising one or more triple helical domains of a human collagen.

7. The recombinant collagen-like protein of claim 6, wherein said collagen-like protein is a fusion protein.

8. A chimeric collagen-like protein, comprising: one or more domains comprising an amino acid sequence of one or more of SEQ ID Nos: 2–9, 15, 37; and/or consisting of SEQ ID Nos: 1 and 10; and one or more triple helical domains of a human collagen or a peptide from within the triple helical domain having a triple helical structure.

9. The chimeric collagen-like protein of claim 8, wherein said protein is a synthetic protein or a fusion protein.

* * * * *